US 10,959,989 B2

(12) United States Patent
Huang et al.

(10) Patent No.: US 10,959,989 B2
(45) Date of Patent: Mar. 30, 2021

(54) ESTROGEN RECEPTOR MODULATORS

(71) Applicant: Recurium IP Holdings, LLC, San Diego, CA (US)

(72) Inventors: Peter Qinhua Huang, San Diego, CA (US); Deborah Helen Slee, Encinitas, CA (US); Sayee Gajanan Hegde, San Diego, CA (US); Chad Daniel Hopkins, San Diego, CA (US); Kevin Duane Bunker, Escondido, CA (US); Joseph Robert Pinchman, San Diego, CA (US); Rakesh Kumar Sit, San Diego, CA (US)

(73) Assignee: Recurium IP Holdings, LLC, San Diego, CA (US)

( * ) Notice: Subject to any disclaimer, the term of this patent is extended or adjusted under 35 U.S.C. 154(b) by 0 days.

(21) Appl. No.: 16/866,995

(22) Filed: May 5, 2020

(65) Prior Publication Data
US 2020/0261429 A1    Aug. 20, 2020

Related U.S. Application Data

(62) Division of application No. 16/086,434, filed as application No. PCT/US2017/024809 on Mar. 29, 2017, now abandoned.

(60) Provisional application No. 62/317,254, filed on Apr. 1, 2016.

(51) Int. Cl.
| C07D 209/10 | (2006.01) |
| A61K 31/438 | (2006.01) |
| C07C 69/738 | (2006.01) |
| C07C 69/732 | (2006.01) |
| C07D 471/04 | (2006.01) |
| C07B 59/00  | (2006.01) |
| C07C 69/757 | (2006.01) |
| A61P 5/30   | (2006.01) |
| A61P 35/00  | (2006.01) |
| A61K 31/437 | (2006.01) |

(52) U.S. Cl.
CPC .......... *A61K 31/438* (2013.01); *A61K 31/437* (2013.01); *A61P 5/30* (2018.01); *A61P 35/00* (2018.01); *C07B 59/002* (2013.01); *C07C 69/732* (2013.01); *C07C 69/738* (2013.01); *C07C 69/757* (2013.01); *C07D 209/10* (2013.01); *C07D 471/04* (2013.01); *C07C 2603/62* (2017.05)

(58) Field of Classification Search
CPC .................................................. C07D 209/10
See application file for complete search history.

(56) References Cited

U.S. PATENT DOCUMENTS

| 2014/0018433 A1 | 1/2014  | Dalton et al.    |
| 2014/0235660 A1 | 8/2014  | Burks et al.     |
| 2015/0315198 A1 | 11/2015 | Li et al.        |
| 2017/0368003 A1 | 12/2017 | Narayanan et al. |
| 2018/0273487 A1 | 9/2018  | Narayanan et al. |

FOREIGN PATENT DOCUMENTS

| CN | 102432608      | 5/2012  |
| CN | 108329311 A    | 7/2018  |
| EA | 16160          | 2/2012  |
| EP | 3378861        | 9/2018  |
| RU | 2472782        | 1/2013  |
| WO | WO 95/24200    | 9/1995  |
| WO | WO 9732860     | 9/1997  |
| WO | WO 2003/033496 | 4/2003  |
| WO | WO 2006/015035 | 2/2006  |
| WO | WO 2007/002051 | 1/2007  |
| WO | WO 2008/002490 | 1/2008  |
| WO | WO 2008/127714 | 10/2008 |
| WO | WO 2008/127715 | 10/2008 |
| WO | WO 2010/083136 | 7/2010  |

(Continued)

OTHER PUBLICATIONS

Office Action issued in Israeli Application No. 261654 dated Aug. 31, 2020.

(Continued)

*Primary Examiner* — Brian E McDowell
(74) *Attorney, Agent, or Firm* — Knobbe Martens Olson & Bear LLP

(57) ABSTRACT

Compounds of Formula (I) are estrogen receptor alpha modulators, where the variables in Formula (I) are described in the disclosure. Such compounds, as well as pharmaceutically acceptable salts and compositions thereof, are useful for treating diseases or conditions that are estrogen receptor alpha dependent and/or estrogen receptor alpha mediated, including conditions characterized by excessive cellular proliferation, such as breast cancer.

Formula (I)

3 Claims, 2 Drawing Sheets

(56) References Cited

FOREIGN PATENT DOCUMENTS

| WO | WO 2010/107485 | 9/2010 |
|---|---|---|
| WO | WO 2011/088025 | 7/2011 |
| WO | WO 2011/103487 | 8/2011 |
| WO | WO 2011/156518 | 12/2011 |
| WO | WO 2013/090829 | 6/2013 |
| WO | WO 2013/090836 | 6/2013 |
| WO | WO 2013/142266 | 9/2013 |
| WO | WO 2014/151899 | 9/2014 |
| WO | WO 2014/191726 | 12/2014 |
| WO | WO 2015/082990 | 6/2015 |
| WO | WO 2015/197861 | 12/2015 |
| WO | WO 2016/172358 | 10/2016 |
| WO | WO 2017/080338 | 5/2017 |
| WO | WO 2017/136688 | 8/2017 |
| WO | WO 2017/172957 | 10/2017 |
| WO | WO 2017214634 | 12/2017 |
| WO | WO 2018/001232 | 1/2018 |
| WO | WO 2018/065501 | 4/2018 |
| WO | WO 2018/130124 | 7/2018 |

OTHER PUBLICATIONS

Bragg, et al, "The synthesis of tritium, carbon-14 and stable isotope labelled selective estrogen receptor degraders", Journal of Labelled Compounds and Radiopharmaceuticals, vol. 59, No. 11, Sep. 1, 2016, pp. 454-461.

De Savi, C. et al., "Optimization of a Novel Binding Motif to (E) 3-(3,5-Difluoro-4-((1R,3R)2-(2-fluoro-2-methylpropyl)-3-methyl-2,3,4,9-tetrahydro-1Hpyrido[3,4b]indol-1-yl)phenyl)acrylic Acid (AZD9496), a Potent and Orally Bioavailable Selective Estrogen Receptor Downregulator and Antagonist", J. Med. Chem. 58, 8128-8140 (2015).

De Savi, Chris, "Discovery of AZD9496: an oral, selective estrogen receptor down-regulator (SERD)" (2015).

Garner, F. et al., "RAD1901: a novel, orally bioavailable selective estrogen receptor degrader that demonstrates antitumor activity in breast cancer xenograft models" Anti-Cancer Drugs 26(9), 948-956 (2015).

Gobe, V., et al., "Self-Relay Gold(I)-Catalyzed Pictet-Spengler/Cyclization Cascade Reaction for the Rapid Elaboration of Pentacyclic Indole Derivatives", Chemistry—A European Journal (2015), 21(49), 17587-17590.

Journal of Labelled Compounds and Radiopharmaceuticals, 2016, 59, 454-461—CAPLUS database with Registry No. 1998721-67-7 info shown only.

Lai, A. et al., "Identification of GDC-0810 (ARN-810), an Orally Bioavailable Selective Estrogen Receptor Degrader (SERD) that Demonstrates Robust Activity in Tamoxifen-Resistant Breast Cancer Xenografts", J. Med. Chem. 58, 4888-4904 (2015).

McDonnell, D., et al., "Oral Selective Estrogen Receptor Downregulators (SERDs), a Breakthrough Endocrine Therapy for Breast Cancer", Journal of Medicinal Chemistry 2015, 58, 12, 4883-4887, Jun. 3, 2015.

Walji, Abbas M., et al., "Discovery of MK-8970: An Acetal Carbonate Prodrug of Raltegravir with Enhanced Colonic Absorption," ChemMedChem (2015), 10, 245-252.

Weir, H. M. et al., "AZD9496: An Oral Estrogen Receptor Inhibitor That Blocks the Growth of ER-Positive and ESR1-Mutant Breast Tumors in Preclinical Models" Cancer Res. 2016;76:3307-3318.

International Search Report and Written Opinion dated Jun. 20, 2017 for PCT Application No. PCT/US2017/024809, filed Mar. 29, 2017.

International Preliminary Report on Patentability dated Oct. 2, 2018 for PCT Application No. PCT/US2017/024809, filed Mar. 29, 2017.

Extended European Search Report issued in Application No. 17776574.0 dated Dec. 3, 2019.

Written Opinion issued in Singapore Application No. 11201807708S dated Jan. 13, 2020.

Examination Report in Indian Patent Application No. 201817038848 dated Sep. 25, 2020.

Samatar, Ahmed A. et al. "Discovery of ZN-c5 a Novel Potent and Oral Selective Estrogen Receptor Degrader", Poster #4373, AACR Virtual Annual Meeting (Jun. 22, 2020).

Office Action issued in Russian Application No. 2018132037 dated May 15, 2020.

ESTROGEN RECEPTOR MODULATORS

INCORPORATION BY REFERENCE TO ANY PRIORITY APPLICATIONS

This application is a divisional of U.S. application Ser. No. 16/086,434, filed Sep. 19, 2018, which is a national stage filing under § 371 of PCT Application No. PCT/US2017/024809, filed Mar. 29, 2017, which claims priority to U.S. Provisional Application Ser. No. 62/317,254, filed September Apr. 1, 2016. All of the foregoing are hereby incorporated herein by references in their entireties.

FIELD

The present application relates to compounds that are estrogen receptor alpha modulators and methods of using them to treat conditions characterized by excessive cellular proliferation, such as cancer.

DESCRIPTION

Many cancer cells express estrogen receptors (ERs) and have growth characteristics that are modulated by estrogen. A number of breast cancer drug therapies have been developed that target ERs. In many cases the drugs are selective estrogen receptor modulators (SERMs) that have agonistic and/or antagonistic effects on ERs. For example, fulvestrant is a drug that is used for the treatment of metastatic breast cancer. It has antagonistic effects on ER-alpha and is considered a selective estrogen receptor alpha degrader (SERD). Fulvestrant has the following chemical structure:

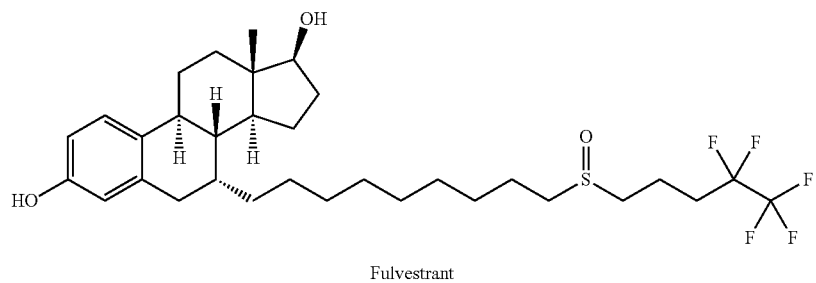

Fulvestrant

A compound known as RAD1901 has also been reported to be a SERD. See Garner, F. et al., "RAD1901: a novel, orally bioavailable selective estrogen receptor degrader that demonstrates antitumor activity in breast cancer xenograft models" Anti-Cancer Drugs 26(9), 948-956 (2015). RAD1901 has the following chemical structure:

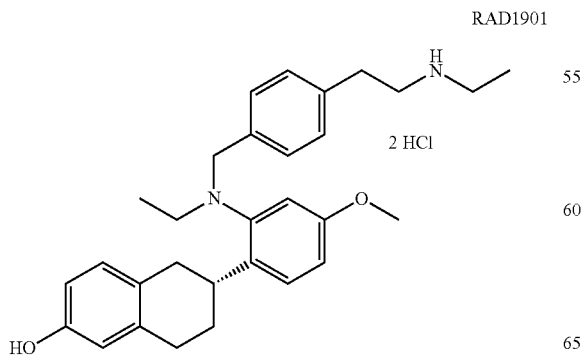

RAD1901

Other reported SERDs include the compounds known as AZD9496 and GDC-0810. See De Savi, C. et al., "Optimization of a Novel Binding Motif to (E)-3-(3,5-Difluoro-4-((1R,3R)2-(2-fluoro-2-methylpropyl)-3-methyl-2,3,4,9-tetrahydro-1H-pyrido[3,4b]indol-1-yl)phenyl)acrylic Acid (AZD9496), a Potent and Orally Bioavailable Selective Estrogen Receptor Downregulator and Antagonist", J. Med. Chem. 58, 8128-8140 (2015) ("De Savi") and Lai, A. et al., "Identification of GDC-0810 (ARN-810), an Orally Bioavailable Selective Estrogen Receptor Degrader (SERD) that Demonstrates Robust Activity in Tamoxifen-Resistant Breast Cancer Xenografts", J. Med. Chem. 58, 4888-4904 (2015). AZD9496 and GDC-0810 have the following chemical structures:

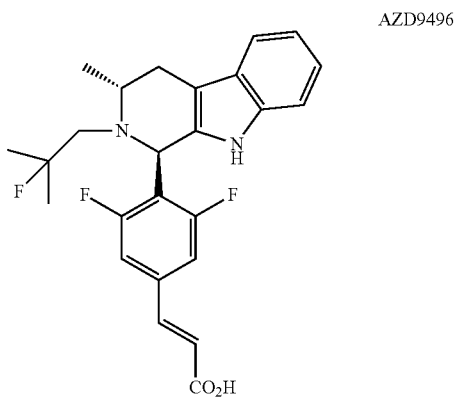

AZD9496

-continued

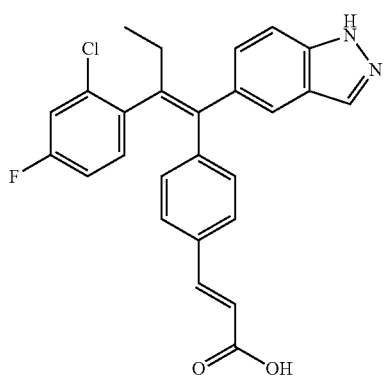

GDC-0810

Other reported SERDs include those disclosed in WO 2008/002490; WO 2011/156518; WO 2013/090829; WO 2013/090836; WO 2013/142266; WO 2014/151899; WO 2014/191726; WO 2015/082990; and US 2014/00235660.

At this time the only SERD approved for the treatment of breast cancer in the United States is fulvestrant. However, the clinical efficacy of fulvestrant is limited and fulvestrant has to be dosed via intramuscular injection. A number of orally dosed SERDs are currently in clinical development (e.g. ARN-810 (GDC-0810), AZD9496, SRN-927, RAD1901, LSZ102), but at this time no oral SERD has been approved for the treatment of breast cancer in the United States (see De Savi, C. et al. publication referenced above). Thus, there remains a long-felt need for well tolerated orally dosed SERDs or SERMs that are useful in the study and the treatment of proliferative disorders, such as breast cancer, that have growth characteristics that are modulated by estrogen.

SUMMARY

An embodiment provides a compound of Formula (I), or a pharmaceutically acceptable salt thereof, having the structure below.

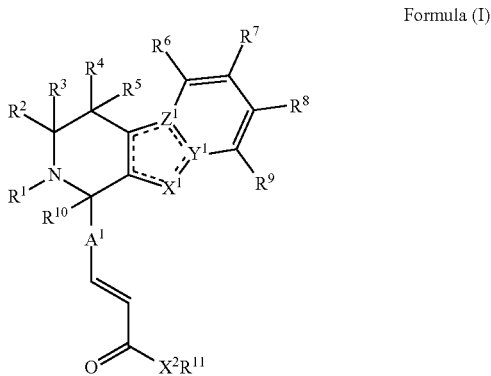

Formula (I)

In an embodiment, $X^1$, $Y^1$ and $Z^1$ are each independently C or N, with the first proviso that at least one of $X^1$, $Y^1$ and $Z^1$ is N; with the second proviso that each of $X^1$, $Y^1$ and $Z^1$ is uncharged; with third proviso that two of the dotted lines indicate double bonds; and with the fourth proviso that the valencies of $X^1$, $Y^1$ and $Z^1$ can be each independently satisfied by attachment to a substituent selected from H and $R^{12}$.

In an embodiment, $A^1$ is selected from the group consisting of an optionally substituted cycloalkyl, an optionally substituted aryl, an optionally substituted heteroaryl and an optionally substituted heterocyclyl. In an embodiment, $X^2$ is O, NH or S.

In an embodiment, $R^1$ is selected from the group consisting of an optionally substituted $C_{1-6}$ alkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-6}$ alkyl), an optionally substituted cycloalkenyl($C_{1-6}$ alkyl), an optionally substituted aryl ($C_{1-6}$ alkyl), an optionally substituted heteroaryl($C_{1-6}$ alkyl) and an optionally substituted heterocyclyl($C_{1-6}$ alkyl).

In an embodiment, $R^2$ and $R^3$ are each independently selected from the group consisting of hydrogen, halogen, an optionally substituted $C_{1-6}$ alkyl and an optionally substituted $C_{1-6}$ haloalkyl; or $R^2$ and $R^3$ together with the carbon to which $R^2$ and $R^3$ are attached form an optionally substituted cycloalkyl, an optionally substituted cycloalkenyl or an optionally substituted heterocyclyl.

In an embodiment, $R^4$ and $R^5$ are each independently selected from the group consisting of hydrogen, halogen, an optionally substituted $C_{1-6}$ alkyl and an optionally substituted $C_{1-6}$ haloalkyl; or $R^4$ and $R^5$ together with the carbon to which $R^4$ and $R^5$ are attached form an optionally substituted cycloalkyl, an optionally substituted cycloalkenyl or an optionally substituted heterocyclyl.

In an embodiment, $R^6$, $R^7$, $R^8$ and $R^9$ are each independently selected from the group consisting of hydrogen, halogen, hydroxy, an optionally substituted alkyl, an optionally substituted alkoxy, an optionally substituted haloalkyl, an optionally substituted mono-substituted amine, and an optionally substituted di-substituted amine.

In an embodiment, $R^{10}$ is hydrogen, halogen, an optionally substituted alkyl, or an optionally substituted cycloalkyl.

In an embodiment, $R^{11}$ is hydrogen or an optionally substituted $C_{1-6}$ alkyl.

In an embodiment, $R^{12}$ is hydrogen, halogen, an optionally substituted $C_{1-3}$ alkyl, an optionally substituted $C_{1-3}$ haloalkyl or an optionally substituted $C_{1-3}$ alkoxy.

In an embodiment, provided that when $R^{11}$ is hydrogen or methyl, $X^1$ is NH, $Y^1$ and $Z^1$ are each C, $X^2$ is O, $A^1$ is a phenyl, 2-fluorophenyl, or 2,6-difluorophenyl, both $R^2$ and $R^3$ are methyl or one of $R^2$ and $R^3$ is hydrogen and the other of $R^2$ and $R^3$ is methyl, and $R^4$, $R^5$, $R^6$, $R^7$, $R^8$, $R^9$ and $R^{10}$ are each hydrogen, then $R^1$ cannot be 2-hydroxyethyl, 2-methylpropyl, 2-fluoro-2-methylpropyl, 3-fluoro-2-methylpropyl, 3-hydroxy-2-methylpropyl or 2-fluoro-3-hydroxy-2-methylpropyl.

In an embodiment, any one or more of each of $R^2$, $R^3$, $R^4$, $R^5$, $R^6$, $R^7$, $R^8$, $R^9$ and $R^{10}$ is hydrogen.

An embodiment provides a pharmaceutical composition comprising an effective amount of the compound of Formula (I), or a pharmaceutically acceptable salt thereof, and a pharmaceutically acceptable carrier, diluent, excipient or combination thereof.

An embodiment provides a method of treatment, comprising identifying a subject that is in need of treatment for a disease or condition that is estrogen receptor alpha dependent and/or estrogen receptor alpha mediated; and administering to said subject an effective amount of a compound of Formula (I), or a pharmaceutically acceptable salt thereof, or a pharmaceutical composition comprising a compound of Formula (I). In an embodiment, the disease or condition is selected from the group consisting of a breast cancer and a gynecological cancer. In an embodiment, the disease or condition is selected from the group consisting of breast cancer, endometrial cancer, ovarian cancer, and cervical cancer.

An embodiment provides a compound of Formula (I), or a pharmaceutically acceptable salt thereof, or a pharmaceutical composition comprising a compound of Formula (I), for use in the treatment of a disease or condition that is estrogen receptor alpha dependent and/or estrogen receptor alpha mediated.

These and other embodiments are described in greater detail below.

DRAWINGS

DETAILED DESCRIPTION

Definitions

Figure 1:
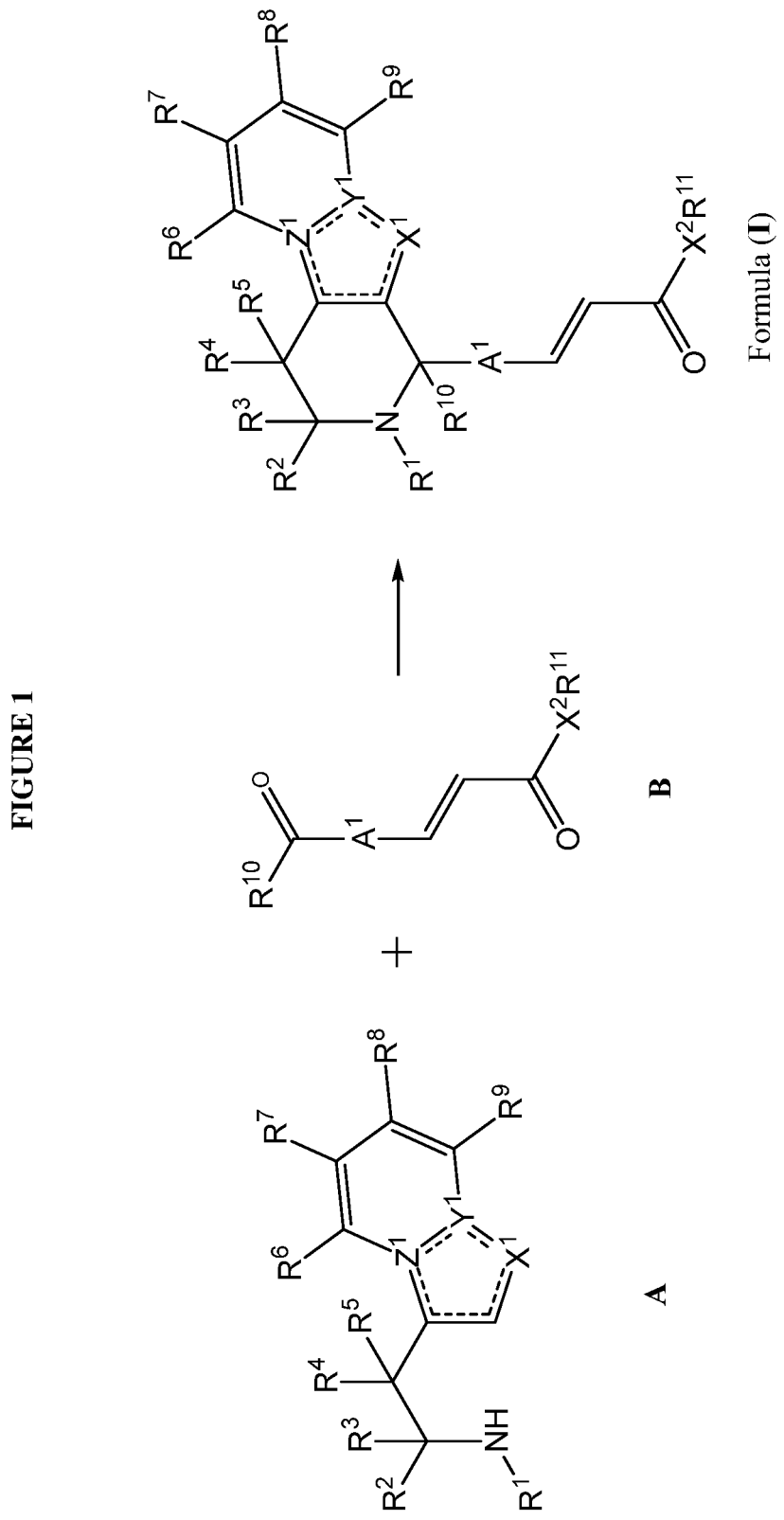
FIG. 1 illustrates General Scheme 1 for preparing compounds of the Formula (I).

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more the indicated substituents. If no substituents are indicated, it is meant that the indicated "optionally substituted" or "substituted" group may be substituted with one or more group(s) individually and independently selected from alkyl, alkenyl, alkynyl, cycloalkyl, cycloalkenyl, cycloalkynyl, aryl, heteroaryl, heterocyclyl, aryl(alkyl), cycloalkyl(alkyl), heteroaryl(alkyl), heterocyclyl(alkyl), hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, nitro, sulfenyl, sulfinyl, sulfonyl, haloalkyl, haloalkoxy, an amino, a mono-substituted amino group and a di-substituted amino group.

As used herein, "$C_a$ to $C_b$" in which "a" and "b" are integers refer to the number of carbon atoms in a group. The indicated group can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated, the broadest range described in these definitions is to be assumed.

If two "R" groups are described as being "taken together" the R groups and the atoms they are attached to can form a cycloalkyl, cycloalkenyl, aryl, heteroaryl or heterocycle. For example, without limitation, if $R^a$ and $R^b$ of an $NR^a R^b$ group are indicated to be "taken together," it means that they are covalently bonded to one another to form a ring:

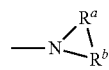

As used herein, the term "alkyl" refers to a fully saturated aliphatic hydrocarbon group. The alkyl moiety may be branched or straight chain. Examples of branched alkyl groups include, but are not limited to, iso-propyl, sec-butyl, t-butyl and the like. Examples of straight chain alkyl groups include, but are not limited to, methyl, ethyl, n-propyl, n-butyl, n-pentyl, n-hexyl, n-heptyl and the like. The alkyl group may have 1 to 30 carbon atoms (whenever it appears herein, a numerical range such as "1 to 30" refers to each integer in the given range; e.g., "1 to 30 carbon atoms" means that the alkyl group may consist of 1 carbon atom, 2 carbon atoms, 3 carbon atoms, etc., up to and including 30 carbon atoms, although the present definition also covers the occurrence of the term "alkyl" where no numerical range is designated). The alkyl group may also be a medium size alkyl having 1 to 12 carbon atoms. The alkyl group could also be a lower alkyl having 1 to 6 carbon atoms. An alkyl group may be substituted or unsubstituted.

The term "alkenyl" used herein refers to a monovalent straight or branched chain radical of from two to twenty carbon atoms containing a carbon double bond(s) including, but not limited to, 1-propenyl, 2-propenyl, 2-methyl-1-propenyl, 1-butenyl, 2-butenyl and the like. An alkenyl group may be unsubstituted or substituted.

The term "alkynyl" used herein refers to a monovalent straight or branched chain radical of from two to twenty carbon atoms containing a carbon triple bond(s) including, but not limited to, 1-propynyl, 1-butynyl, 2-butynyl and the like. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused, bridged or spiro fashion. As used herein, the term "fused" refers to two rings which have two atoms and one bond in common. As used herein, the term "bridged cycloalkyl" refers to compounds wherein the cycloalkyl contains a linkage of one or more atoms connecting non-adjacent atoms. As used herein, the term "spiro" refers to two rings which have one atom in common and the two rings are not linked by a bridge. Cycloalkyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). A cycloalkyl group may be unsubstituted or substituted. Typical mono-cycloalkyl groups include, but are in no way limited to, cyclopropyl, cyclobutyl, cyclopentyl, cyclohexyl, cycloheptyl, and cyclooctyl. Examples of fused cycloalkyl groups are decahydronaphthalenyl, dodecahydro-1H-phenalenyl and tetradecahydroanthracenyl; examples of bridged cycloalkyl groups are bicyclo[1.1.1]pentyl, adamantanyl, and norbornanyl; and examples of spiro cycloalkyl groups include spiro[3.3]heptane and spiro[4.5]decane.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). Cycloalkenyl groups can contain 3 to 10 atoms in the ring(s) or 3 to 8 atoms in the ring(s). When composed of two or more rings, the rings may be connected together in a fused, bridged or spiro fashion. A cycloalkenyl group may be unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. Cycloalkynyl groups can contain 6 to 10 atoms in the ring(s) or 6 to 8 atoms in the ring(s). When composed of two or more rings, the rings may be joined together in a fused, bridged or spiro fashion. A cycloalkynyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic or multicyclic aromatic ring system (a ring system with fully delocalized pi-electron system) that contain(s) one or more heteroatoms (for example, 1, 2 or 3 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" or "heteroalicyclyl" refers to three-, four-, five-, six-, seven-, eight-, nine-, ten-, up to 18-membered monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused, bridged or spiro fashion. As used herein, the term "fused" refers to two rings which have two atoms and one bond in common. As used herein, the term "bridged heterocyclyl" or "bridged heteroalicyclyl" refers to compounds wherein the heterocyclyl or heteroalicyclyl contains a linkage of one or more atoms connecting non-adjacent atoms. As used herein, the term "spiro" refers to two rings which have one atom in common and the two rings are not linked by a bridge. Heterocyclyl and heteroalicyclyl groups can contain 3 to 30 atoms in the ring(s), 3 to 20 atoms in the ring(s), 3 to 10 atoms in the ring(s), 3 to 8 atoms in the ring(s) or 3 to 6 atoms in the ring(s). Additionally, any nitrogens in a heteroalicyclic may be quaternized. Heterocyclyl or heteroalicyclic groups may be unsubstituted or substituted. Examples of such "heterocyclyl" or "heteroalicyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, azepane, pyrrolidinone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and/or 3,4-methylenedioxyphenyl). Examples of spiro heterocyclyl groups include 2-azaspiro[3.3]heptane, 2-oxaspiro[3.3]heptane, 2-oxa-6-azaspiro[3.3]heptane, 2,6-diazaspiro[3.3]heptane, 2-oxaspiro[3.4]octane and 2-azaspiro[3.4]octane.

As used herein, "aralkyl" and "aryl(alkyl)" refer to an aryl group connected, as a substituent, via a lower alkylene group. The lower alkylene and aryl group of an aralkyl may be substituted or unsubstituted. Examples include but are not limited to benzyl, 2-phenylalkyl, 3-phenylalkyl and naphthylalkyl.

As used herein, "heteroaralkyl" and "heteroaryl(alkyl)" refer to a heteroaryl group connected, as a substituent, via a lower alkylene group. The lower alkylene and heteroaryl group of heteroaralkyl may be substituted or unsubstituted. Examples include but are not limited to 2-thienylalkyl, 3-thienylalkyl, furylalkyl, thienylalkyl, pyrrolylalkyl, pyridylalkyl, isoxazolylalkyl and imidazolylalkyl and their benzo-fused analogs.

A "heteroalicyclyl(alkyl)" and "heterocyclyl(alkyl)" refer to a heterocyclic or a heteroalicyclylic group connected, as a substituent, via a lower alkylene group. The lower alkylene and heterocyclyl of a (heteroalicyclyl)alkyl may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl (methyl) and 1,3-thiazinan-4-yl(methyl).

As used herein, "lower alkylene groups" are straight-chained —$CH_2$-tethering groups, forming bonds to connect molecular fragments via their terminal carbon atoms. Examples include but are not limited to methylene (—$CH_2$—), ethylene (—$CH_2CH_2$—), propylene (—$CH_2CH_2CH_2$—) and butylene (—$CH_2CH_2CH_2CH_2$—). A lower alkylene group can be substituted by replacing one or more hydrogen of the lower alkylene group and/or by substituting both hydrogens on the same carbon with a cycloalkyl group (e.g.,

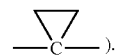

).

As used herein, the term "hydroxy" refers to a —OH group.

As used herein, "alkoxy" refers to the Formula —OR wherein R is an alkyl, an alkenyl, an alkynyl, a cycloalkyl, a cycloalkenyl, aryl, heteroaryl, heterocyclyl, cycloalkyl (alkyl), aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen, alkyl, alkenyl, alkynyl, aryl, heteroaryl, heterocyclyl, aryl(alkyl), heteroaryl(alkyl) and heterocyclyl(alkyl) connected, as substituents, via a carbonyl group. Examples include formyl, acetyl, propanoyl, benzoyl and acryl. An acyl may be substituted or unsubstituted.

A "cyano" group refers to a "—CN" group.

The term "halogen atom" or "halogen" as used herein, means any one of the radio-stable atoms of column 7 of the Periodic Table of the Elements, such as, fluorine, chlorine, bromine and iodine.

A "thiocarbonyl" group refers to a "—C(=S)R" group in which R can be the same as defined with respect to O-carboxy. A thiocarbonyl may be substituted or unsubstituted.

An "O-carbamyl" group refers to a "—OC(=O)N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-carbamyl may be substituted or unsubstituted.

An "N-carbamyl" group refers to an "ROC(=O)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-carbamyl may be substituted or unsubstituted.

An "O-thiocarbamyl" group refers to a "—OC(=S)—N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An O-thiocarbamyl may be substituted or unsubstituted.

An "N-thiocarbamyl" group refers to an "ROC(=S)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-thiocarbamyl may be substituted or unsubstituted.

A "C-amido" group refers to a "—C(=O)N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A C-amido may be substituted or unsubstituted.

An "N-amido" group refers to a "RC(=O)N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-amido may be substituted or unsubstituted.

An "S-sulfonamido" group refers to a "—SO$_2$N(R$_A$R$_B$)" group in which R$_A$ and R$_B$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An S-sulfonamido may be substituted or unsubstituted.

An "N-sulfonamido" group refers to a "RSO$_2$N(R$_A$)—" group in which R and R$_A$ can be independently hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). An N-sulfonamido may be substituted or unsubstituted.

An "O-carboxy" group refers to a "RC(=O)O—" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. An O-carboxy may be substituted or unsubstituted.

The terms "ester" and "C-carboxy" refer to a "—C(=O)OR" group in which R can be the same as defined with respect to O-carboxy. An ester and C-carboxy may be substituted or unsubstituted.

A "nitro" group refers to an "—NO$_2$" group.

A "sulfenyl" group refers to an "—SR" group in which R can be hydrogen, an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl). A sulfenyl may be substituted or unsubstituted.

A "sulfinyl" group refers to an "—S(=O)—R" group in which R can be the same as defined with respect to sulfenyl. A sulfinyl may be substituted or unsubstituted.

A "sulfonyl" group refers to an "SO$_2$R" group in which R can be the same as defined with respect to sulfenyl. A sulfonyl may be substituted or unsubstituted.

As used herein, "haloalkyl" refers to an alkyl group in which one or more of the hydrogen atoms are replaced by a halogen (e.g., mono-haloalkyl, di-haloalkyl and trio-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

The term "amino" as used herein refers to a —NH$_2$ group.

A "mono-substituted amino" group refers to a "—NHR" group in which R can be an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. A mono-substituted amino may be substituted or unsubstituted. Examples of mono-substituted amino groups include, but are not limited to, —NH(methyl), —NH(phenyl) and the like.

A "di-substituted amino" group refers to a "—NR$_A$R$_B$" group in which R$_A$ and R$_B$ can be independently an alkyl, an alkenyl, an alkynyl, a cycloalkyl, a cycloalkenyl, aryl, heteroaryl, heterocyclyl, cycloalkyl(alkyl), aryl(alkyl), heteroaryl(alkyl) or heterocyclyl(alkyl), as defined herein. A di-substituted amino may be substituted or unsubstituted. Examples of di-substituted amino groups include, but are not limited to, —N(methyl)$_2$, —N(phenyl)(methyl), —N(ethyl)(methyl) and the like.

Where the numbers of substituents is not specified (e.g. haloalkyl), there may be one or more substituents present. For example "haloalkyl" may include one or more of the same or different halogens. As another example, "C$_1$-C$_3$ alkoxyphenyl" may include one or more of the same or different alkoxy groups containing one, two or three atoms.

As used herein, a radical indicates species with a single, unpaired electron such that the species containing the radical can be covalently bonded to another species. Hence, in this context, a radical is not necessarily a free radical. Rather, a radical indicates a specific portion of a larger molecule. The term "radical" can be used interchangeably with the term "group."

As used herein, when a chemical group or unit includes an asterisk (*), that asterisk indicates a point of attachment of the group or unit to another structure.

As used herein, "linking groups" are chemical groups that are indicated as having multiple open valencies for connecting to two or more other groups. For example, lower alkylene groups of the general formula —(CH$_2$)$_n$— where n is in the range of 1 to 10, are examples of linking groups that are described elsewhere herein as connecting molecular fragments via their terminal carbon atoms. Other examples of linking groups include —(CH$_2$)$_n$O—, —(CH$_2$)$_n$NH—, —(CH$_2$)$_n$N(C$_1$-C$_6$alkyl)-, and —(CH$_2$)$_n$S—, wherein each n is 0, 1, 2, 3, 4, 5, 6, 7, 8, 9, or 10. Those skilled in the art will recognize that n can be zero for some linking groups such as —(CH$_2$)$_n$O—, in which case the linking group is simply —O—. Those skilled in the art will also recognize that reference herein to an asymmetrical linking group will be understood as a reference to all orientations of that group (unless stated otherwise). For example, reference herein to —(CH$_2$)$_n$O— will be understood as a reference to both —(CH$_2$)$_n$O— and —O—(CH$_2$)$_n$—.

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), a sulfuric acid, a nitric acid and a phosphoric acid (such as 2,3-dihydroxypropyl dihydrogen phosphate). Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluensulfonic, trifluoroacetic, benzoic, salicylic, 2-oxopentanedioic, or naphthalenesulfonic acid. Pharmaceutical salts can also be obtained by reacting a compound with a base to form a salt such as an ammonium salt, an alkali metal salt, such as a sodium, a potassium or a lithium salt, an alkaline earth metal salt, such as a calcium or a magnesium salt, a salt of a carbonate, a salt of a bicarbonate, a salt of organic bases such as dicyclohexylamine, N-methyl-D-glucamine, tris(hydroxymethyl)methylamine, C$_1$-C$_7$ alkylamine, cyclohexylamine, triethanolamine, ethylenediamine, and salts with amino acids such as arginine and lysine. For compounds of Formula (I), those skilled in the art understand that when a salt is formed by protonation of a nitrogen-based group (for example, NH$_2$), the nitrogen-based group can be associated with a positive charge (for example, NH$_2$ can become NH$_3^+$) and the positive charge can be balanced by a negatively charged counterion (such as Cl$^-$).

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, racemic mixture, diastereomerically pure, diastereomerically enriched, or a stereoisomeric mixture. In addition, it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

It is understood that the methods and combinations described herein include crystalline forms (also known as polymorphs, which include the different crystal packing arrangements of the same elemental composition of a compound), amorphous phases, salts, solvates, and hydrates. In some embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; and use of terms like 'preferably,' 'preferred,' 'desired,' or 'desirable,' and words of similar meaning should not be understood as implying that certain features are critical, essential, or even important to the structure or function, but instead as merely intended to highlight alternative or additional features that may or may not be utilized in a particular embodiment. In addition, the term "comprising" is to be interpreted synonymously with the phrases "having at least" or "including at least". When used in the context of a process, the term "comprising" means that the process includes at least the recited steps, but may include additional steps. When used in the context of a compound, composition or device, the term "comprising" means that the compound, composition or device includes at least the recited features or components, but may also include additional features or components. Likewise, a group of items linked with the conjunction 'and' should not be read as requiring that each and every one of those items be present in the grouping, but rather should be read as 'and/or' unless the context indicates otherwise. Similarly, a group of items linked with the conjunction 'or' should not be read as requiring mutual exclusivity among that group, but rather should be read as 'and/or' unless the context indicates otherwise.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

Compounds

Some embodiments disclosed herein relate to compounds of the Formula (I), or pharmaceutically acceptable salts thereof.

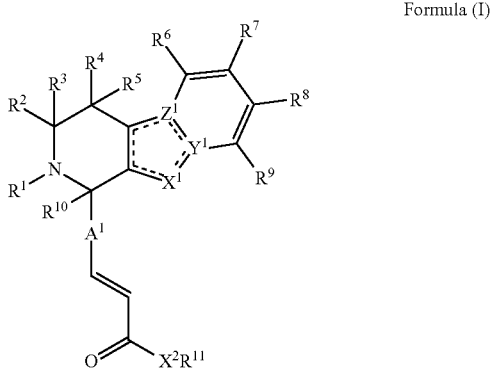

Formula (I)

In various embodiments, compounds of Formula (I) are useful for ameliorating, treating and/or diagnosing a disease or condition that is estrogen receptor dependent and/or estrogen receptor mediated. In an embodiment, the disease is cancer. In an embodiment, the cancer is breast cancer. In an embodiment, compounds of Formula (I) are selective estrogen receptor modulators (SERMs). In an embodiment, compounds of Formula (I) are selective estrogen receptor degraders (SERDs). Additional details regarding various uses and methods of treatment are described elsewhere herein.

In various embodiments the variables $X^1$, $Y^1$ and $Z^1$ in Formula (I) are each independently C or N, with the first proviso that at least one of $X^1$, $Y^1$ and $Z^1$ is N; with the second proviso that each of $X^1$, $Y^1$ and $Z^1$ is uncharged; with third proviso that two of the dotted lines indicate double bonds; and with the fourth proviso that the valencies of $X^1$, $Y^1$ and $Z^1$ can be each independently satisfied by attachment to a substituent selected from H and $R^{12}$. In an embodiment, the variable $X^2$ in Formula (I) is O, NH or S. For example, in an embodiment, $X^2$ is O. In various embodiments, $R^{12}$ is selected from the group consisting of hydrogen, halogen, an optionally substituted $C_{1-3}$ alkyl, an optionally substituted $C_{1-3}$ haloalkyl and an optionally substituted $C_{1-3}$ alkoxy. In an embodiment, $R^{12}$ is hydrogen. In another embodiment, $R^{12}$ is not hydrogen.

In an embodiment the variable $A^1$ in Formula (I) is selected from the group consisting of an optionally substituted cycloalkyl, an optionally substituted aryl, an optionally substituted heteroaryl and an optionally substituted heterocyclyl. In an embodiment $A^1$ is an optionally substituted aryl. For example, in an embodiment $A^1$ is an optionally substituted phenyl. Thus, in various embodiments $A^1$ is a substituted phenyl or an unsubstituted phenyl. In another embodiment $A^1$ is an optionally substituted cycloalkyl. For example, in an embodiment $A^1$ is an optionally substituted bicyclopentyl. Thus, in various embodiments $A^1$ is a substituted bicyclopentyl or an unsubstituted bicyclopentyl.

In various embodiments the variable $R^1$ in Formula (I) is selected from the group consisting of an optionally substituted $C_{1-6}$ alkyl, an optionally substituted cycloalkyl, an optionally substituted cycloalkenyl, an optionally substituted aryl, an optionally substituted heteroaryl, an optionally substituted heterocyclyl, an optionally substituted cycloalkyl($C_{1-6}$ alkyl), an optionally substituted cycloalkenyl($C_{1-6}$ alkyl), an optionally substituted aryl($C_{1-6}$ alkyl), an optionally substituted heteroaryl($C_{1-6}$ alkyl) and an optionally substituted heterocyclyl($C_{1-6}$ alkyl). In an embodiment, $R^1$ is selected from the group consisting of an optionally substituted $C_{1-6}$ alkyl, an optionally substituted cycloalkyl, an optionally substituted cycloalkyl($C_{1-6}$ alkyl), an optionally substituted heterocyclyl and an optionally substituted heterocyclyl($C_{1-6}$ alkyl).

In an embodiment, $R^1$ in Formula (I) is a substituted cycloalkyl. In an embodiment, $R^1$ is substituted cycloalkyl that is substituted with one or more substituents selected from the group consisting of halogen, hydroxy, haloalkyl, an optionally substituted alkyl, an optionally substituted cycloalkyl, a substituted alkoxy, a substituted mono-substituted amine and a substituted di-substituted amine. In an embodiment, $R^1$ is an optionally substituted cycloalkyl selected from the group consisting of unsubstituted cyclobutyl, unsubstituted difluorocyclobutyl, unsubstituted cyclopentyl and unsubstituted bicyclopentyl. In an embodiment, $R^1$ is an optionally substituted cycloalkyl($C_{1-6}$ alkyl) selected from the group consisting of unsubstituted cyclopropylmethyl, unsubstituted bicyclopentylmethyl, unsubstituted fluorocyclopropylmethyl, unsubstituted fluorocyclobutylmethyl, unsubstituted methoxycyclopropylmethyl, and unsubstituted trifluoromethylcyclopropylmethyl. In an embodiment, $R^1$ is an optionally substituted heterocyclyl selected from the group consisting of unsubstituted tetrahydropyranyl, unsubstituted tetrahydrofuranyl, and unsubstituted oxetanyl. In an embodiment, $R^1$ is an optionally substituted heterocyclyl($C_{1-6}$ alkyl) is selected from the group consisting of unsubstituted oxetanylmethyl and unsubstituted fluorooxetanylmethyl In an embodiment, $R^1$ in Formula (I) is a substituted alkyl. In an embodiment, $R^1$ is a substituted alkyl that is substituted with one or more substituents selected from the group consisting of halogen, hydroxy, haloalkyl, an optionally substituted cycloalkyl, a substituted alkoxy, a substituted mono-substituted amine and a substituted di-substituted amine. For example, in an embodiment, $R^1$ is a substituted alkyl that is a haloalkyl. In another embodiment, $R^1$ is an optionally substituted $C_{1-6}$ alkyl selected from the group consisting of $C_4$ alkyl, fluoro($C_4$ alkyl), and trifluoro($C_2$ alkyl).

In various embodiments the variables $R^2$ and $R^3$ in Formula (I) are each independently selected from the group consisting of hydrogen, halogen, an optionally substituted $C_{1-6}$ alkyl and an optionally substituted $C_{1-6}$ haloalkyl. In other embodiments $R^2$ and $R^3$ together with the carbon to which $R^2$ and $R^3$ are attached form an optionally substituted cycloalkyl, an optionally substituted cycloalkenyl or an optionally substituted heterocyclyl. In an embodiment, $R^2$ is selected from the group consisting of hydrogen, methyl, fluoromethyl and difluoromethyl.

In various embodiments the variables $R^4$ and $R^5$ in Formula (I) are each independently selected from the group consisting of hydrogen, halogen, an optionally substituted $C_{1-6}$ alkyl and an optionally substituted $C_{1-6}$ haloalkyl. In other embodiments $R^4$ and $R^5$ together with the carbon to which $R^4$ and $R^5$ are attached form an optionally substituted cycloalkyl, an optionally substituted cycloalkenyl or an optionally substituted heterocyclyl.

In various embodiments the variables $R^6$, $R^7$, $R^8$ and $R^9$ in Formula (I) are each independently selected from the group consisting of hydrogen, halogen, hydroxy, an optionally substituted alkyl, an optionally substituted alkoxy, an optionally substituted haloalkyl, an optionally substituted mono-substituted amine, and an optionally substituted di-substituted amine. In an embodiment, $R^7$ is selected from the group consisting of halogen, hydroxy, and unsubstituted alkoxy. For example, in an embodiment, $R^7$ is selected from the group consisting of fluoro and methoxy.

In various embodiments the variable $R^{10}$ in Formula (I) is hydrogen, halogen, an optionally substituted alkyl, or an optionally substituted cycloalkyl.

In various embodiments the variable $R^{11}$ in Formula (I) is hydrogen or an optionally substituted $C_{1-6}$ alkyl. In an embodiment, $R^{11}$ is an unsubstituted $C_{1-6}$ alkyl. For example, in an embodiment, $R^{11}$ is methyl, ethyl or propyl (e.g., isopropyl or n-propyl).

In an embodiment, provided that when $R^{11}$ is hydrogen or methyl, $X^1$ is NH, $Y^1$ and $Z^1$ are each C, $X^2$ is O, $A^1$ is a phenyl, 2-fluorophenyl, or 2,6-difluorophenyl, both $R^2$ and $R^3$ are methyl or one of $R^2$ and $R^3$ is hydrogen and the other of $R^2$ and $R^3$ is methyl, and $R^4$, $R^5$, $R^6$, $R^7$, $R^8$, $R^9$ and $R^{10}$ are each hydrogen, then $R^1$ cannot be 2-hydroxyethyl, 2-methylpropyl, 2-fluoro-2-methylpropyl, 3-fluoro-2-methylpropyl, 3-hydroxy-2-methylpropyl or 2-fluoro-3-hydroxy-2-methylpropyl.

In another embodiment, provided that when $R^{10}$ is hydrogen, $R^{11}$ is hydrogen or methyl, $X^1$ is NH, $Y^1$ and $Z^1$ are each C, $X^2$ is O, $A^1$ is an optionally substituted phenyl, one of $R^2$ and $R^3$ is hydrogen or an optionally substituted $C_{1-6}$ alkyl and the other of $R^2$ and $R^3$ is an optionally substituted $C_{1-6}$ alkyl, then $R^1$ cannot be a substituted $C_{1-6}$ alkyl substituted with one or more substituents selected from the group consisting of halogen and hydroxy.

Various embodiments provide compounds of the Formula (I), or pharmaceutically acceptable salts thereof, where the compounds of the Formula (I) can be represented by Formulae (Ia), (Ib), (Ic), or (Id), having the structures below.

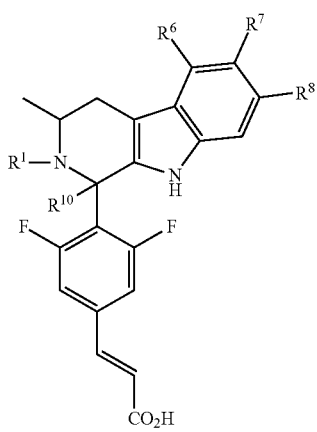

Formula (Ia)

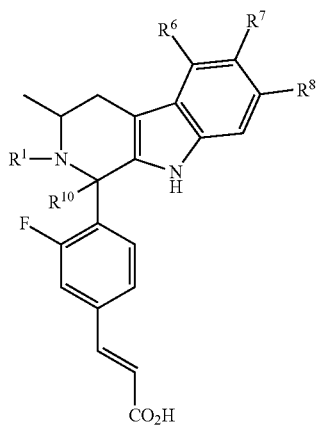

Formula (Ib)

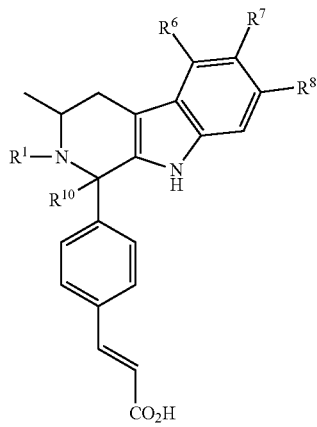

Formula (Ic)

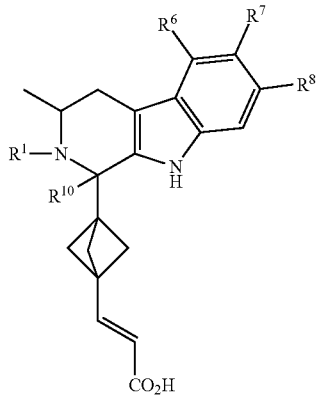

Formula (Id)

In various embodiments, the variables $R^1$, $R^6$, $R^7$, $R^8$ and $R^{10}$ for the compounds of Formulae (Ia), (Ib), (Ic) and (Id) are the same as described elsewhere herein.

In an embodiment, the variable $R^1$ in Formulae (Ia), (Ib), (Ic) and (Id) is an optionally substituted $C_{1-6}$ alkyl selected from the group consisting of $C_4$ alkyl, fluoro($C_4$ alkyl), and trifluoro($C_2$ alkyl). In another embodiment, the variable $R^1$ in Formulae (Ia), (Ib), (Ic) and (Id) is an optionally substituted cycloalkyl selected from the group consisting of unsubstituted cyclobutyl, unsubstituted difluorocyclobutyl, unsubstituted cyclopentyl and unsubstituted bicyclopentyl. In another embodiment, the variable $R^1$ in Formulae (Ia), (Ib), (Ic) and (Id) is an optionally substituted cycloalkyl($C_{1-6}$ alkyl) selected from the group consisting of unsubstituted cyclopropylmethyl, unsubstituted bicyclopentylmethyl, unsubstituted fluorocyclopropylmethyl, unsubstituted fluorocyclobutylmethyl, unsubstituted methoxycyclopropylmethyl, and unsubstituted trifluoromethylcyclopropylmethyl. In another embodiment, the variable $R^1$ in Formulae (Ia), (Ib), (Ic) and (Id) is an optionally substituted heterocyclyl selected from the group consisting of unsubstituted tetrahydropyranyl, unsubstituted tetrahydrofuranyl, and unsubstituted oxetanyl. In another embodiment, the variable $R^1$ in Formulae (Ia), (Ib), (Ic) and (Id). In another embodiment, the variable $R^1$ in Formulae (Ia), (Ib), (Ic) and (Id) is an optionally substituted heterocyclyl($C_{1-6}$ alkyl) selected from the group consisting of unsubstituted oxetanylmethyl and unsubstituted fluorooxetanylmethyl. In various embodiments, when the variables $R^6$, $R^7$ and $R^8$ are hydrogen, the variable $R^1$ in Formulae (Ia), (Ib), (Ic) and (Id) cannot be 2-hydroxyethyl, 2-methylpropyl, 2-fluoro-2-methylpropyl, 3-fluoro-2-methylpropyl, 3-hydroxy-2-methylpropyl or 2-fluoro-3-hydroxy-2-methylpropyl.

In an embodiment, the variables $R^6$, $R^7$ and $R^8$ in Formulae (Ia), (Ib), (Ic) and (Id) are each independently selected from the group consisting of halogen e.g., fluoro, chloro or bromo), hydroxy, and unsubstituted alkoxy (e.g., methoxy, ethoxy or propoxy). In another embodiment, the variables $R^6$ and $R^8$ in Formulae (Ia), (Ib), (Ic) and (Id) are both hydrogen. In another embodiment, the variables $R^6$ and $R^7$ in Formulae (Ia), (Ib), (Ic) and (Id) are both hydrogen. In another embodiment, the variables $R^7$ and $R^8$ in Formulae (Ia), (Ib), (Ic) and (Id) are both hydrogen.

In an embodiment, the variable $R^{10}$ in Formulae (Ia), (Ib), (Ic) and (Id) is hydrogen or a $C_{1-6}$ alkyl. In an embodiment, the variable $R^{10}$ in Formulae (Ia), (Ib), (Ic) and (Id) is not hydrogen.

Various embodiments provide compounds of the Formula (I), or pharmaceutically acceptable salts thereof, where the compounds of the Formula (I) can be represented by Formulae (Ie), (If), (Ig) and (Ih), having the structures below.

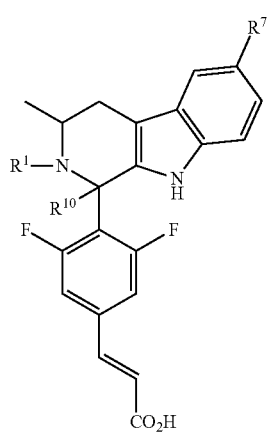

Formula (Ie)

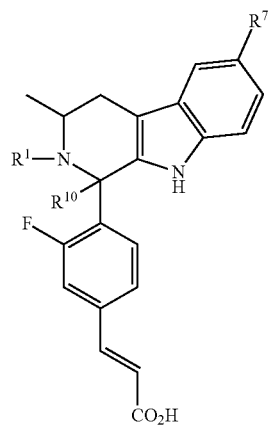

Formula (If)

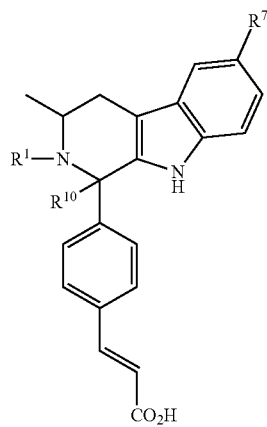

Formula (Ig)

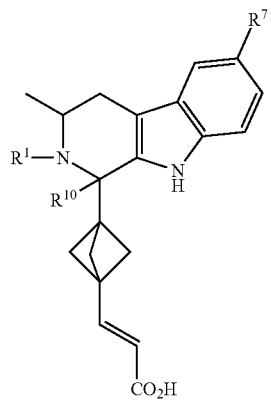

Formula (Ih)

In various embodiments, the variables $R^1$, $R^7$, and $R^{10}$ for the compounds of Formulae (Ie), (If), (Ig) and (Ih) are the same as described elsewhere herein.

In an embodiment, the variable $R^1$ in Formulae (Ie), (If), (Ig) and (Ih) is an optionally substituted $C_{1-6}$ alkyl selected from the group consisting of $C_4$ alkyl, fluoro($C_4$ alkyl), and trifluoro($C_2$ alkyl). In another embodiment, the variable $R^1$ in Formulae (Ie), (If), (Ig) and (Ih) is an optionally substituted cycloalkyl selected from the group consisting of unsubstituted cyclobutyl, unsubstituted difluorocyclobutyl, unsubstituted cyclopentyl and unsubstituted bicyclopentyl. In another embodiment, the variable $R^1$ in Formulae (Ie), (If), (Ig) and (Ih) is an optionally substituted cycloalkyl($C_{1-6}$ alkyl) selected from the group consisting of unsubstituted cyclopropylmethyl, unsubstituted bicyclopentylmethyl, unsubstituted fluorocyclopropylmethyl, unsubstituted fluorocyclobutylmethyl, unsubstituted methoxycyclopropylmethyl, and unsubstituted trifluoromethylcyclopropylmethyl. In another embodiment, the variable $R^1$ in Formulae (Ie), (If), (Ig) and (Ih) is an optionally substituted heterocyclyl selected from the group consisting of unsubstituted tetrahydropyranyl, unsubstituted tetrahydrofuranyl, and unsubstituted oxetanyl. In another embodiment, the variable $R^1$ in Formulae (Ie), (If), (Ig) and (Ih). In another embodiment, the variable $R^1$ in Formulae (Ie), (If), (Ig) and (Ih) is an optionally substituted heterocyclyl($C_{1-6}$ alkyl) selected from the group consisting of unsubstituted oxetanylmethyl and unsubstituted fluorooxetanylmethyl. In various embodiments, when the variable $R^7$ is hydrogen, the variable $R^1$ in Formulae (Ie), (If), (Ig) and (Ih) cannot be 2-hydroxyethyl, 2-methylpropyl, 2-fluoro-2-methylpropyl, 3-fluoro-2-methylpropyl, 3-hydroxy-2-methylpropyl or 2-fluoro-3-hydroxy-2-methylpropyl.

In an embodiment, the variable $R^7$ in Formulae (Ie), (If), (Ig) and (Ih) is selected from the group consisting of halogen (e.g., fluoro, chloro or bromo), hydroxy, and unsubstituted alkoxy (e.g., methoxy, ethoxy or propoxy). In an embodiment, the variable $R^{10}$ in Formulae (Ie), (If), (Ig) and (Ih) is hydrogen or a $C_{1-6}$ alkyl. In an embodiment, the variable $R^{10}$ in Formulae (Ie), (If), (Ig) and (Ih) is not hydrogen.

Methods of Making

Compounds of the Formula (I), or pharmaceutically acceptable salts thereof, can be made in various ways by those skilled using known techniques as guided by the detailed teachings provided herein. For example, in an embodiment, compounds of the Formula (I) are prepared in accordance with General Scheme 1 as shown in FIG. 1. The variables in General Scheme 1 are as described elsewhere herein with respect to the Formula (I). In general, the ring formation and coupling reaction between compounds of the general formulae (A) and (B) to form compounds of the Formula (I) as illustrated in General Scheme 1 can be carried out in a manner similar to that of the reaction between (R)—N-(1-(1H-indol-3-yl)propan-2-yl)-2-fluoro-2-methylpropan-1-amine and ethyl (E)-3-(3-formylbicyclo[1.1.1]pentan-1-yl)acrylate as described in Example 1A below. Any preliminary reaction steps required to form starting compounds of the general formulae (A) and (B) can be readily carried out by those skilled in the art in view of the detailed teaching provided herein, e.g., by appropriate adjustment of the reagents and conditions described in Example 1A for the preparation of (R)—N-(1-(1H-indol-3-yl)propan-2-yl)-2-fluoro-2-methylpropan-1-amine and ethyl (E)-3-(3-formylbicyclo[1.1.1]pentan-1-yl)acrylate, respectively. Similarly, any intermediate reaction products formed as a result of the reaction between compounds of the general formulae (A) and (B) can be readily converted to compounds of the Formula (I) by those skilled in the art in view of the detailed teaching provided herein, e.g., by appropriate adjustment of the reagents and conditions described in Example 1A for the preparation of Compound 1A from intermediate ethyl (E)-3-(3-((1R,3R)-2-(2-fluoro-2-methylpropyl)-3-methyl-2,3,4,9-tetrahydro-1H-pyrido[3,4-b]indol-1-yl)bicyclo[1.1.1]pentan-1-yl)acrylate.

Uses and Methods of Treatment

As described herein, one or more compounds of Formula (I), or pharmaceutically acceptable salts thereof, or a pharmaceutical composition as described herein, can be used to inhibit the growth of a cell. In an embodiment, the cell is identified as having an estrogen receptor that mediates a growth characteristic of the cell. Growth of a cell can be inhibited by contacting the cell with an effective amount of at least one of the compounds described herein, or pharmaceutically acceptable salts thereof, or a pharmaceutical composition as described elsewhere herein. Such contacting of the one or more compounds, or pharmaceutically acceptable salts thereof, can take place in various ways and locations, including without limitation away from a living subject (e.g., in a laboratory, diagnostic and/or analytical setting) or in proximity to a living subject (e.g., within or on an exterior portion of an animal, e.g., a human). For example, an embodiment provides a method of treating a subject, comprising identifying a subject that is in need of treatment for a disease or condition that is estrogen receptor dependent and/or estrogen receptor mediated and administering to said subject an effective amount of one or more compounds of Formula (I), or a pharmaceutically acceptable salt thereof, or a pharmaceutical composition, as described elsewhere herein. Another embodiment provides a use of one or more compounds of Formula (I), or a pharmaceutically acceptable salt thereof, or a pharmaceutical composition (as described elsewhere herein), in the manufacture of a medicament for the treatment of a disease or condition that is estrogen receptor alpha dependent and/or estrogen receptor alpha mediated.

Non-limiting examples of diseases or conditions that are estrogen receptor alpha dependent and/or estrogen alpha receptor mediated and thus suitable for treatment using the compounds, compositions and methods described herein include breast cancers and gynecological cancers. For example, such diseases or conditions may include one or more of the following: breast cancer, endometrial cancer, ovarian cancer and cervical cancer. An embodiment provides a use of one or more compounds of Formula (I), or a pharmaceutically acceptable salt thereof, or a pharmaceutical composition (as described elsewhere herein), in the manufacture of a medicament for the treatment of breast cancers and gynecological cancers, including for example one or more of the following: breast cancer, endometrial cancer, ovarian cancer and cervical cancer.

As described herein, compounds of Formula (I), or a pharmaceutically acceptable salt thereof, or a pharmaceutical composition as described elsewhere herein, can be administered to such subjects by a variety of methods. In any of the uses or methods described herein, administration can be by various routes known to those skilled in the art, including without limitation oral, intravenous, intramuscular, topical, subcutaneous, systemic, and/or intraperitoneal administration to a subject in need thereof.

As used herein, the terms "treat," "treating," "treatment," "therapeutic," and "therapy" do not necessarily mean total cure or abolition of the estrogen receptor dependent and/or estrogen receptor mediated disease or condition. Any alleviation of any undesired signs or symptoms of the disease or condition, to any extent can be considered treatment and/or therapy. Furthermore, treatment may include acts that may worsen the subject's overall feeling of well-being or appearance.

The terms "therapeutically effective amount" and "effective amount" are used to indicate an amount of an active compound, or pharmaceutical agent, that elicits the biological or medicinal response indicated. For example, a therapeutically effective amount of compound, salt or composition can be the amount needed to prevent, alleviate or ameliorate symptoms of the estrogen receptor dependent and/or estrogen receptor mediated disease or condition, or prolong the survival of the subject being treated This response may occur in a tissue, system, animal or human and includes alleviation of the signs or symptoms of the estrogen receptor dependent and/or estrogen receptor mediated disease or condition being treated. Determination of an effective amount is well within the capability of those skilled in the art, in view of the disclosure provided herein. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

The amount of the compound of Formula (I), or a pharmaceutically acceptable salt thereof, required for use in treatment will vary not only with the particular compound or salt selected but also with the route of administration, the nature and/or symptoms of the estrogen receptor dependent and/or estrogen receptor mediated disease or condition being treated and the age and condition of the patient and will be ultimately at the discretion of the attendant physician or clinician. In cases of administration of a pharmaceutically acceptable salt, dosages may be calculated as the free base. As will be understood by those of skill in the art, in certain situations it may be necessary to administer the compounds disclosed herein in amounts that exceed, or even far exceed, the dosage ranges described herein in order to effectively and aggressively treat particularly aggressive estrogen receptor dependent and/or estrogen receptor mediated diseases or conditions.

In general, however, a suitable dose will often be in the range of from about 0.05 mg/kg to about 10 mg/kg. For example, a suitable dose may be in the range from about 0.10 mg/kg to about 7.5 mg/kg of body weight per day, such as about 0.15 mg/kg to about 5.0 mg/kg of body weight of the recipient per day, about 0.2 mg/kg to 4.0 mg/kg of body weight of the recipient per day. The compound may be administered in unit dosage form; for example, containing 1 to 500 mg, 10 to 100 mg or 5 to 50 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

As will be readily apparent to one skilled in the art, the useful in vivo dosage to be administered and the particular mode of administration will vary depending upon the age, weight, the severity of the affliction, and mammalian species treated, the particular compounds employed, and the specific use for which these compounds are employed. The determination of effective dosage levels, that is the dosage levels necessary to achieve the desired result, can be accomplished by one skilled in the art using routine methods, for example, human clinical trials, in vivo studies and in vitro studies. For example, useful dosages of a compound of Formula (I), or pharmaceutically acceptable salts thereof, can be determined by comparing their in vitro activity, and in vivo activity in animal models. Such comparison can be done by comparison against an established drug, such as fulvestrant.

Dosage amount and interval may be adjusted individually to provide plasma levels of the active moiety which are sufficient to maintain the modulating effects, or minimal effective concentration (MEC). The MEC will vary for each compound but can be estimated from in vivo and/or in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the estrogen receptor dependent and/or estrogen receptor mediated disease or condition to be treated and to the route of administration. The severity of the estrogen receptor dependent and/or estrogen receptor mediated disease or condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Compounds, salts and compositions disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, dogs or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

Pharmaceutical Compositions

Some embodiments described herein relate to a pharmaceutical composition, that can include an effective amount of one or more compounds described herein (e.g., a compound of Formula (I), or a pharmaceutically acceptable salt thereof) and a pharmaceutically acceptable carrier, diluent, excipient or combination thereof.

The term "pharmaceutical composition" refers to a mixture of one or more compounds and/or salts disclosed herein with other chemical components, such as diluents or carriers. The pharmaceutical composition facilitates administration of the compound to an organism. Pharmaceutical compositions can also be obtained by reacting compounds with inorganic or organic acids such as hydrochloric acid, hydrobromic acid, sulfuric acid, nitric acid, phosphoric acid, methanesulfonic acid, ethanesulfonic acid, p-toluenesulfonic acid, and salicylic acid. Pharmaceutical compositions will generally be tailored to the specific intended route of administration.

The term "physiologically acceptable" defines a carrier, diluent or excipient that does not abrogate the biological activity and properties of the compound nor cause appreciable damage or injury to an animal to which delivery of the composition is intended.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks appreciable pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the pH and isotonicity of human blood.

As used herein, an "excipient" refers to an essentially inert substance that is added to a pharmaceutical composition to provide, without limitation, bulk, consistency, stability, binding ability, lubrication, disintegrating ability etc., to the composition. For example, stabilizers such as anti-oxidants and metal-chelating agents are excipients. In an embodiment, the pharmaceutical composition comprises an anti-oxidant and/or a metal-chelating agent. A "diluent" is a type of excipient.

The pharmaceutical compositions described herein can be administered to a human patient per se, or in pharmaceutical compositions where they are mixed with other active ingredients, as in combination therapy, or carriers, diluents, excipients or combinations thereof. Proper formulation is dependent upon the route of administration chosen. Techniques for formulation and administration of the compounds described herein are known to those skilled in the art.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. Additionally, the active ingredients are contained in an amount effective to achieve its intended purpose. Many of the compounds used in the pharmaceutical combinations disclosed herein may be provided as salts with pharmaceutically compatible counterions.

Multiple techniques of administering a compound, salt and/or composition exist in the art including, but not limited to, oral, rectal, pulmonary, topical, aerosol, injection, infusion and parenteral delivery, including intramuscular, subcutaneous, intravenous, intramedullary injections, intrathecal, direct intraventricular, intraperitoneal, intranasal and intraocular injections.

One may also administer the compound, salt and/or composition in a local rather than systemic manner, for example, via injection or implantation of the compound directly into the affected area, often in a depot or sustained release formulation. Furthermore, one may administer the compound in a targeted drug delivery system, for example, in a liposome coated with a tissue-specific antibody. The liposomes will be targeted to and taken up selectively by the organ. For example, intranasal or pulmonary delivery to target a respiratory disease or condition may be desirable.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound and/or salt described herein formulated in a compatible pharmaceutical carrier may also be prepared, placed in an appropriate container, and labeled for treatment of an indicated condition.

EXAMPLES

Additional embodiments are disclosed in further detail in the following examples, which are not in any way intended to limit the scope of the claims.

Compounds

The compounds of Formula (I) illustrated in Table 1 can be prepared in various ways, using techniques known to those skilled in the art as guided by the detailed teachings provided herein. For example, the compounds of Formula (I) illustrated in Table 1 can be prepared in accordance with General Scheme 1 as described in the Examples below. Likewise, the compounds of Formula (I) illustrated in Table 2 can be readily prepared in accordance with General Scheme 1 in view of the detailed teachings set forth in the Examples below. Those skilled in the art will understand that a number of structures shown in Table 1 are not stereospecific and/or are depicted as having unfilled valencies, and thus are generic to isotopic and/or stereochemical variants, including racemates, diastereomers, enantiomers and/or deuterated versions, which can be prepared in accordance with the guidance provided herein.

TABLE 1

| No. | Compound Structure |
| --- | --- |
| 1 | 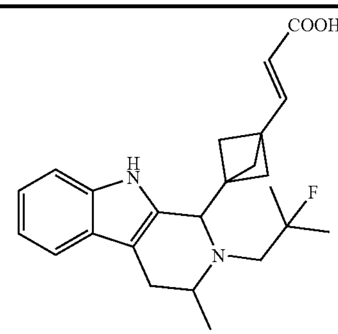 |
| 1A | 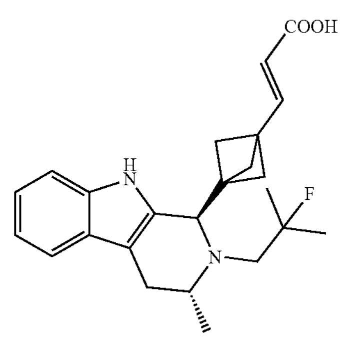 [SMILES: C[C@@H]1Cc2c([nH]c3ccccc23)[C@@H](C23CC(/C=C/C(=O)O)(C2)C3)N1CC(C)(C)F] |

TABLE 1-continued

| No. | Compound Structure |
|---|---|
| 1B | (structure) |
| 2 | (structure) |
| 2A | (structure) |
| 3 | (structure) |
| 3A | (structure) |
| 4 | (structure) |
| 4A | (structure) |
| 4B | (structure) |

TABLE 1-continued

| No. | Compound Structure |
|---|---|
| 5 | (structure) |
| 5A | (structure) |
| 5B | (structure) |
| 5C | (structure) |
| 6 | (structure) |
| 6A | (structure) |
| 7 | (structure) |
| 7A | (structure) |

TABLE 1-continued
| No. | Compound Structure |
|---|---|
| 8 | 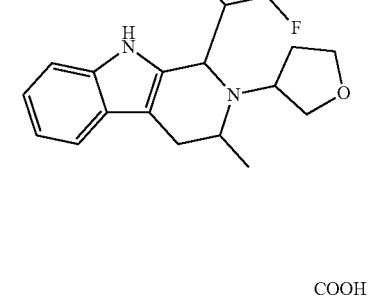 |
| 8A | 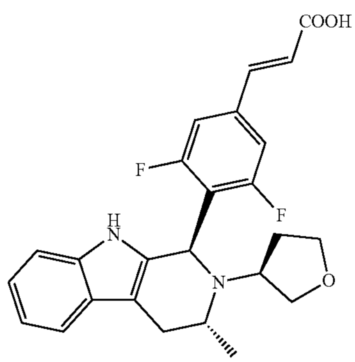 [SMILES: C[C@@H]1Cc2c([nH]c3ccccc23)[C@@H](c2c(F)cc(/C=C/C(=O)O)cc2F)N1[C@H]1CCOC1] |
| 8B | 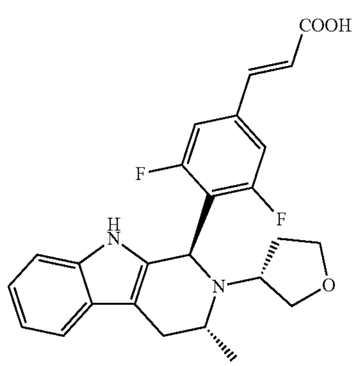 [SMILES: C[C@@H]1Cc2c([nH]c3ccccc23)[C@@H](c2c(F)cc(/C=C/C(=O)O)cc2F)N1[C@@H]1CCOC1] |
| 8C | 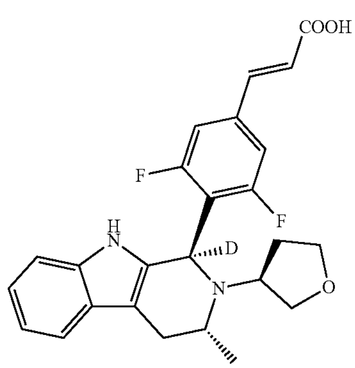 [SMILES: [2H][C@@]1(c2c(F)cc(/C=C/C(=O)O)cc2F)c2[nH]c3ccccc3c2C[C@@H](C)N1[C@H]1CCOC1] |
TABLE 1-continued
| No. | Compound Structure |
|---|---|
| 9 | 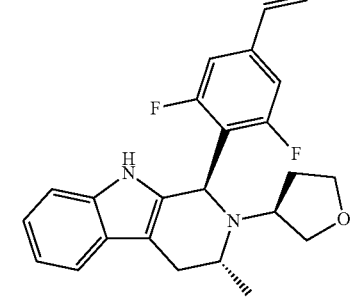 |
| 9A | 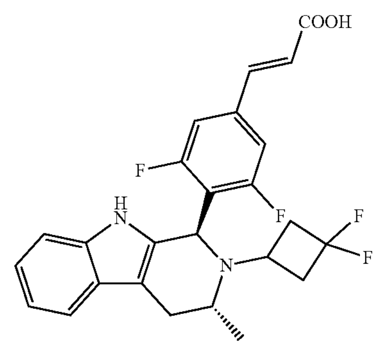 [SMILES: C[C@@H]1Cc2c([nH]c3ccccc23)[C@@H](c2c(F)cc(/C=C/C(=O)O)cc2F)N1C1CC(F)(F)C1] |
| 9B | 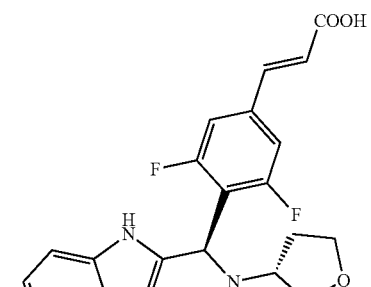 |
| 10 | 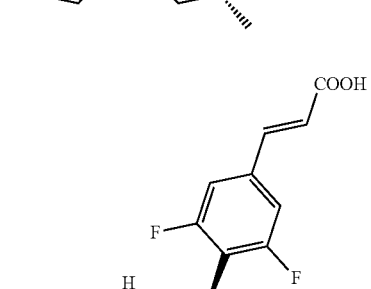 |

TABLE 1-continued

| No. | Compound Structure |
|---|---|
| 10A | 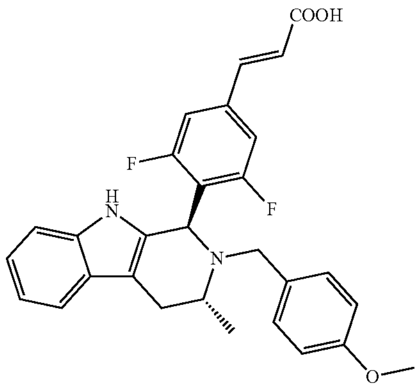 [SMILES: COc1ccc(CN2[C@H](c3c(F)cc(/C=C/C(=O)O)cc3F)c3[nH]c4ccccc4c3C[C@H]2C)cc1] |
| 11 | 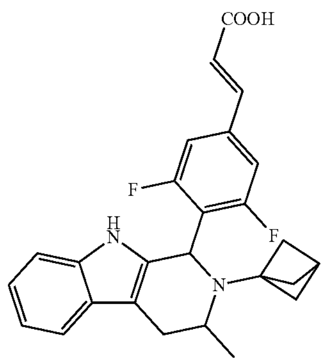 [SMILES: CC1Cc2c([nH]c3ccccc23)C(c2c(F)cc(/C=C/C(=O)O)cc2F)N1C12CC(C1)C2] |
| 11A | 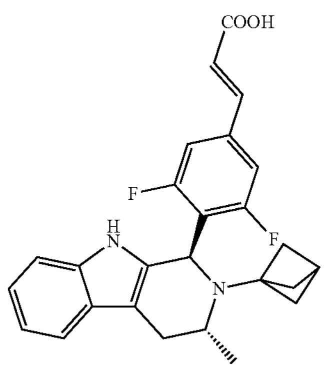 [SMILES: C[C@@H]1Cc2c([nH]c3ccccc23)[C@@H](c2c(F)cc(/C=C/C(=O)O)cc2F)N1C12CC(C1)C2] |
| 11B | 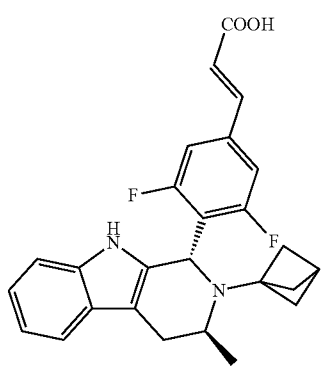 [SMILES: C[C@H]1Cc2c([nH]c3ccccc23)[C@H](c2c(F)cc(/C=C/C(=O)O)cc2F)N1C12CC(C1)C2] |
| 11C | |
| 11D | |
| 12 | |
| 12A | |

TABLE 1-continued
| No. | Compound Structure |
|---|---|
| 13 | 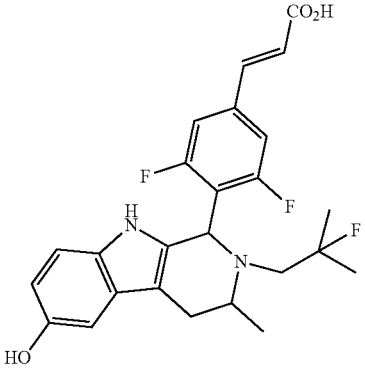 [SMILES: CC1Cc2c([nH]c3ccc(O)cc23)C(c2c(F)cc(/C=C/C(=O)O)cc2F)N1CC(C)(C)F] |
| 13A | 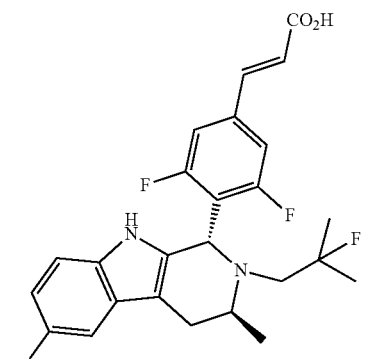 |
| 13B | 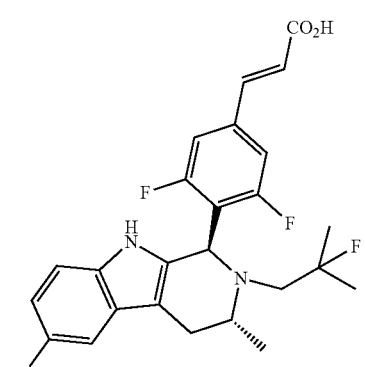 |
| 14 | 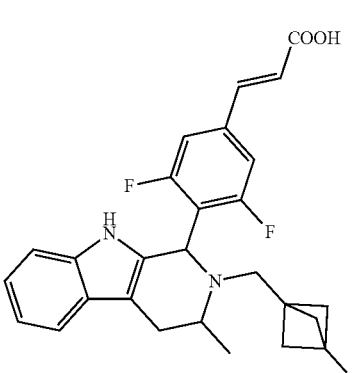 |
| 14A | 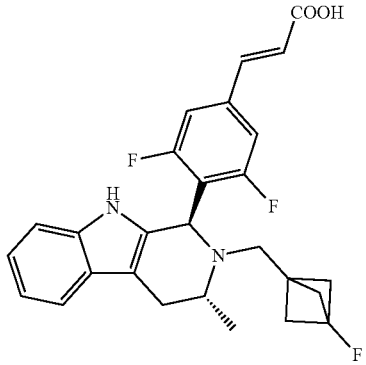 [SMILES: C[C@@H]1Cc2c([nH]c3ccccc23)[C@@H](c2c(F)cc(/C=C/C(=O)O)cc2F)N1CC12CC(F)(C1)C2] |
| 15 | 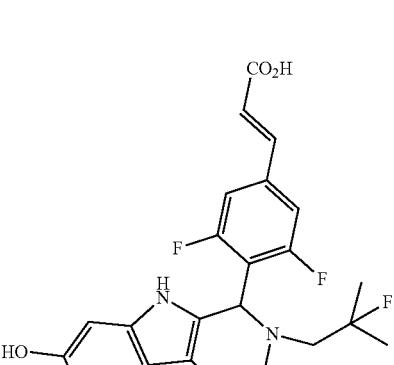 |
| 15A |  |
| 16 |  |

TABLE 1-continued

| No. | Compound Structure |
|---|---|
| 16A | 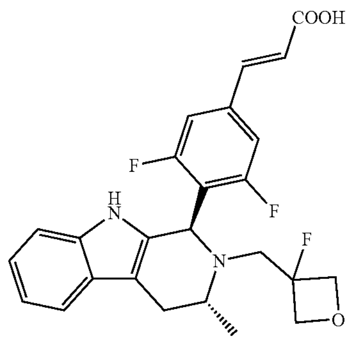 [SMILES: C[C@@H]1Cc2c([nH]c3ccccc23)[C@@H](c2c(F)cc(/C=C/C(=O)O)cc2F)N1CC1(F)COC1] |
| 17 | 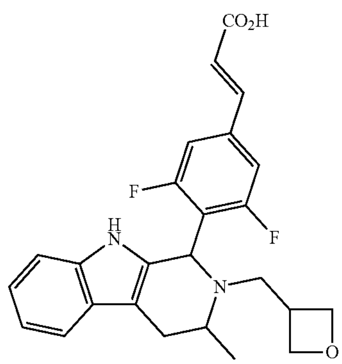 [SMILES: CC1Cc2c([nH]c3ccccc23)C(c2c(F)cc(/C=C/C(=O)O)cc2F)N1CC1COC1] |
| 17A | 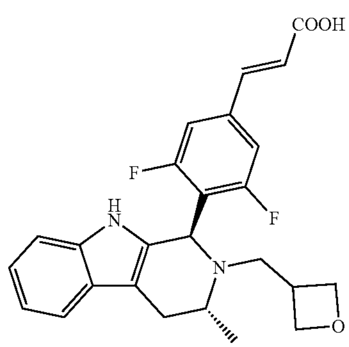 [SMILES: C[C@@H]1Cc2c([nH]c3ccccc23)[C@@H](c2c(F)cc(/C=C/C(=O)O)cc2F)N1CC1COC1] |
| 18 | 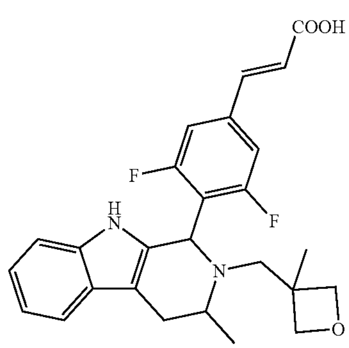 [SMILES: CC1Cc2c([nH]c3ccccc23)C(c2c(F)cc(/C=C/C(=O)O)cc2F)N1CC1(C)COC1] |
| 18A | |
| 19 | |
| 19A | |
| 20 | |

TABLE 1-continued

| No. | Compound Structure |
|-----|--------------------|
| 21  | 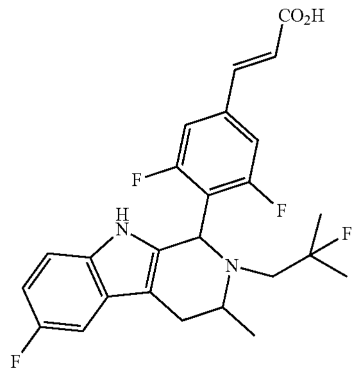 [SMILES: CC1Cc2c([nH]c3ccc(F)cc23)C(c2c(F)cc(/C=C/C(=O)O)cc2F)N1CC(C)(C)F] |
| 21A | 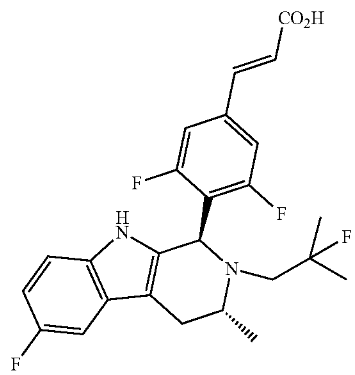 [SMILES: C[C@@H]1Cc2c([nH]c3ccc(F)cc23)[C@@H](c2c(F)cc(/C=C/C(=O)O)cc2F)N1CC(C)(C)F] |
| 22  | 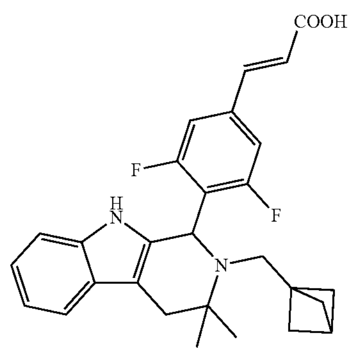 [SMILES: CC1(C)Cc2c([nH]c3ccccc23)C(c2c(F)cc(/C=C/C(=O)O)cc2F)N1CC12CC(C1)C2] |
| 23  | 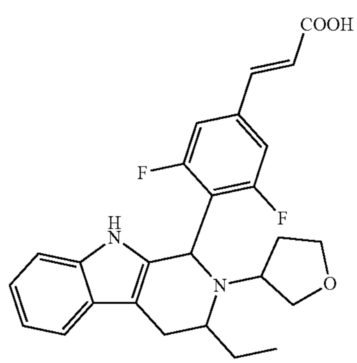 [SMILES: CCC1Cc2c([nH]c3ccccc23)C(c2c(F)cc(/C=C/C(=O)O)cc2F)N1C1CCOC1] |
| 23A | |
| 23B | |
| 24  | |
| 25  | |

TABLE 1-continued
| No. | Compound Structure |
|---|---|
| 25A | 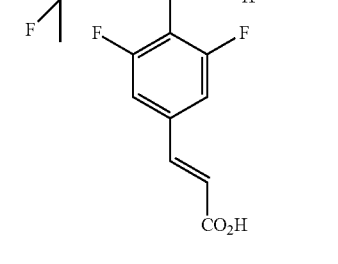 |
| 25B | 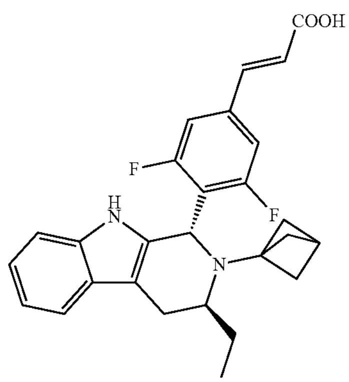 [SMILES: CC[C@H]1Cc2c([nH]c3ccccc23)[C@H](c2c(F)cc(/C=C/C(=O)O)cc2F)N1C12CC(C1)C2] |
| 26 | 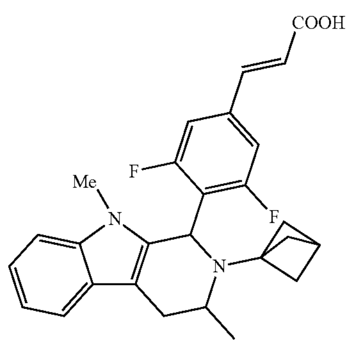 [SMILES: CC1Cc2c(n(C)c3ccccc23)C(c2c(F)cc(/C=C/C(=O)O)cc2F)N1C12CC(C1)C2] |
| 26A | 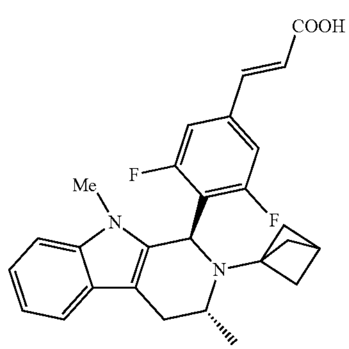 [SMILES: C[C@@H]1Cc2c(n(C)c3ccccc23)[C@@H](c2c(F)cc(/C=C/C(=O)O)cc2F)N1C12CC(C1)C2] |
TABLE 2
| No. | Compound Structure |
|---|---|
| 27 | 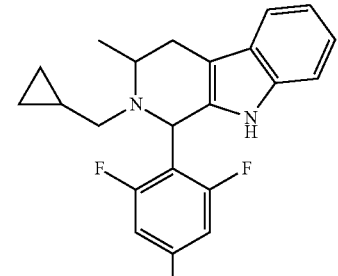 |
| 28 | 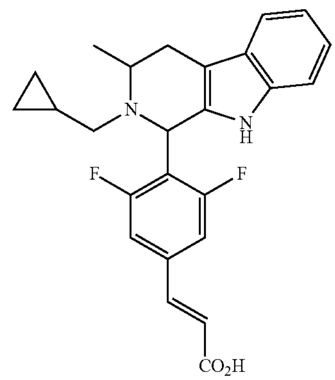 [SMILES: CC1Cc2c([nH]c3ccccc23)C(c2c(F)cc(/C=C/C(=O)O)cc2F)N1CC1CC1] |
| 29 | 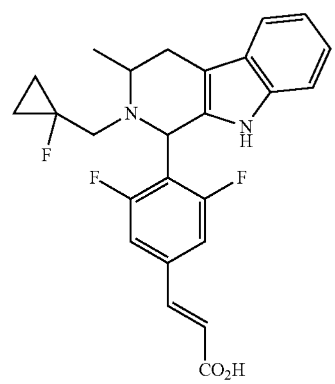 [SMILES: CC1Cc2c([nH]c3ccccc23)C(c2c(F)cc(/C=C/C(=O)O)cc2F)N1CC1(F)CC1] |
| 30 | 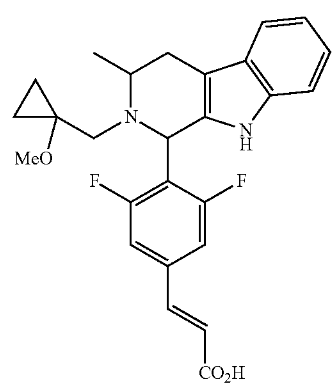 [SMILES: COC1(CN2C(C)Cc3c([nH]c4ccccc34)C2c2c(F)cc(/C=C/C(=O)O)cc2F)CC1] |

TABLE 2-continued
| No. | Compound Structure |
|---|---|
| 31 | 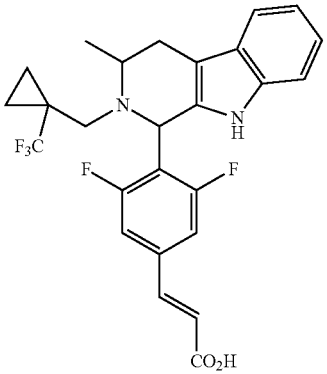 [SMILES: CC1Cc2c([nH]c3ccccc23)C(c2c(F)cc(/C=C/C(=O)O)cc2F)N1CC1(C(F)(F)F)CC1] |
| 32 | 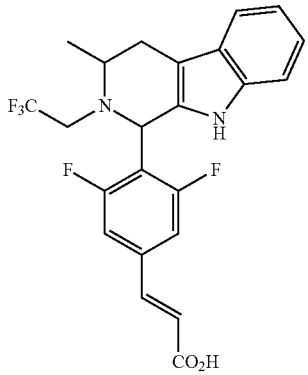 [SMILES: CC1Cc2c([nH]c3ccccc23)C(c2c(F)cc(/C=C/C(=O)O)cc2F)N1CC(F)(F)F] |
| 33 | 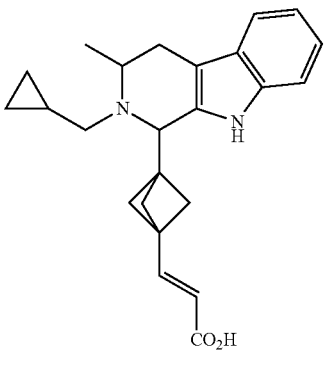 [SMILES: CC1Cc2c([nH]c3ccccc23)C(C23CC(/C=C/C(=O)O)(C2)C3)N1CC1CC1] |
| 34 | 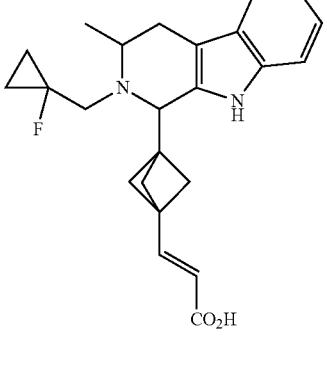 |
| 35 | 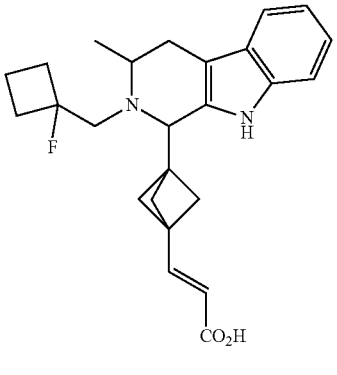 [SMILES: CC1Cc2c([nH]c3ccccc23)C(C23CC(/C=C/C(=O)O)(C2)C3)N1CC1(F)CCC1] |
| 36 | 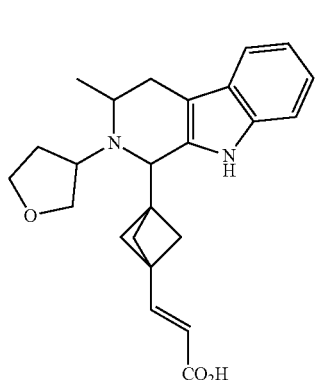 |
| 37 | 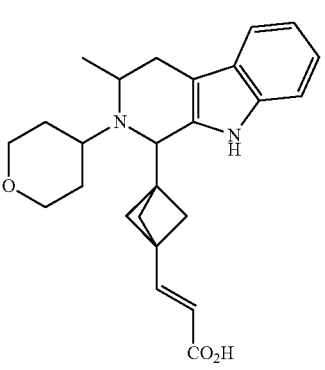 [SMILES: CC1Cc2c([nH]c3ccccc23)C(C23CC(/C=C/C(=O)O)(C2)C3)N1C1CCOCC1] |
| 38 | 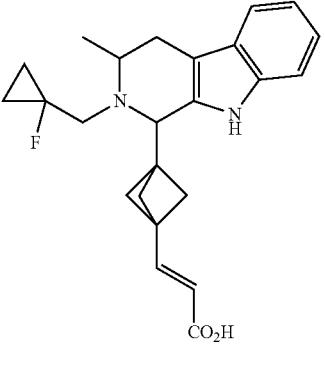 [SMILES: CC1Cc2c([nH]c3ccccc23)C(C23CC(/C=C/C(=O)O)(C2)C3)N1CC1(F)CC1] |

TABLE 2-continued
| No. | Compound Structure |
|---|---|
| 39 | 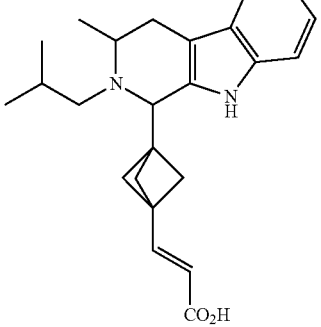 |
| 40 | 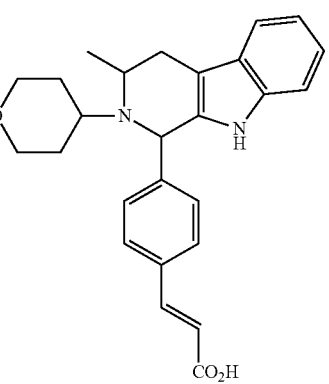 |
| 41 | 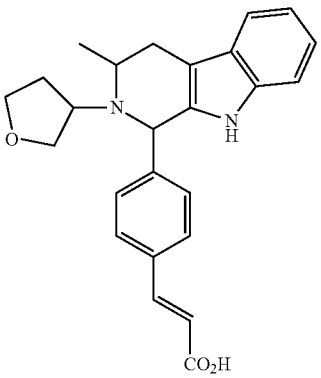 [SMILES: CC1Cc2c([nH]c3ccccc23)C(c2ccc(/C=C/C(=O)O)cc2)N1C1CCOC1] |
| 42 | 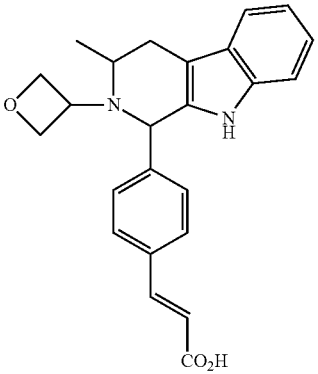 [SMILES: CC1Cc2c([nH]c3ccccc23)C(c2ccc(/C=C/C(=O)O)cc2)N1C1COC1] |
| 43 | 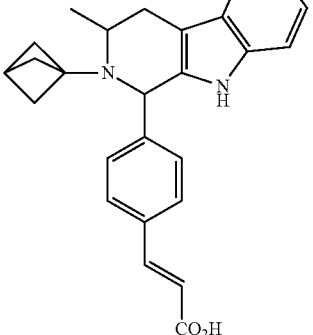 |
| 44 | 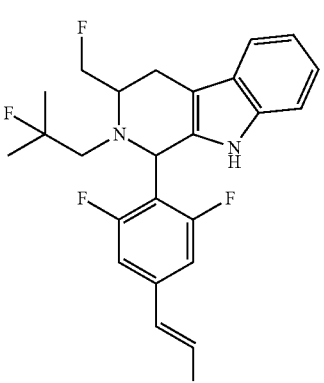 |
| 45 | 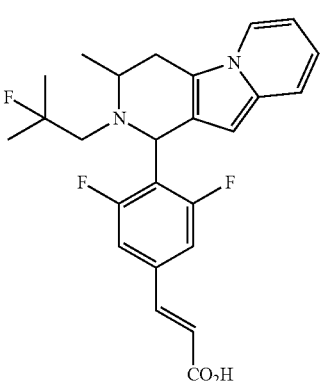 |
| 46 | 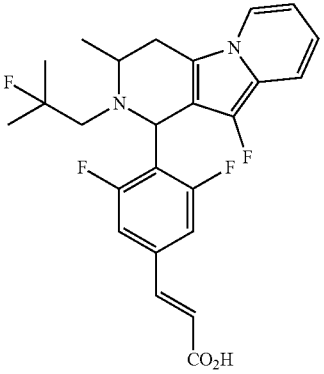 [SMILES: CC1Cc2c(c(F)c3ccccn23)C(c2c(F)cc(/C=C/C(=O)O)cc2F)N1CC(C)(C)F] |

TABLE 2-continued

| No. | Compound Structure |
|---|---|
| 47 | 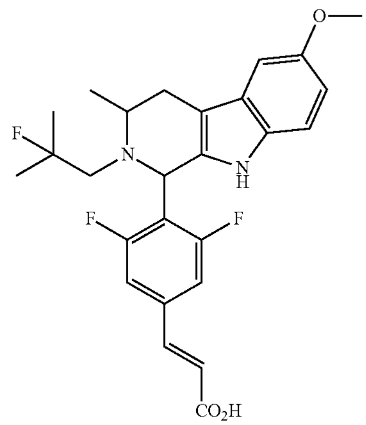 [SMILES: COc1ccc2[nH]c3c(c2c1)CC(C)N(CC(C)(C)F)C3c1c(F)cc(/C=C/C(=O)O)cc1F] |
| 48 | 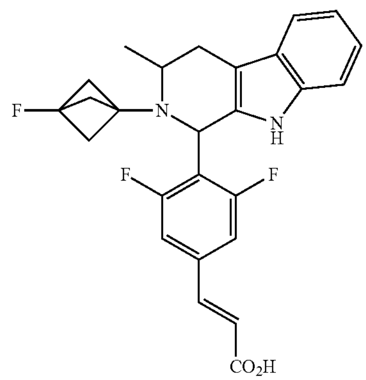 [SMILES: CC1Cc2c([nH]c3ccccc23)C(c2c(F)cc(/C=C/C(=O)O)cc2F)N1C12CC(F)(C1)C2] |
| 49 | 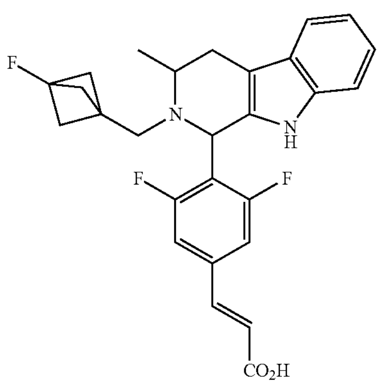 [SMILES: CC1Cc2c([nH]c3ccccc23)C(c2c(F)cc(/C=C/C(=O)O)cc2F)N1CC12CC(F)(C1)C2] |
| 50 | 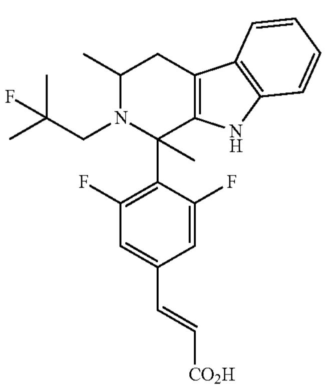 [SMILES: CC1Cc2c([nH]c3ccccc23)C(C)(c2c(F)cc(/C=C/C(=O)O)cc2F)N1CC(C)(C)F] |
| 51 | |

Example 1A (E)-3-(3-((1R,3R)-2-(2-Fluoro-2-methylpropyl)-3-methyl-2,3,4,9-tetrahydro-1H-pyrido[3,4-b]indol-1-yl)bicyclo[1.1.1]pentan-1-yl)acrylic acid (1A)

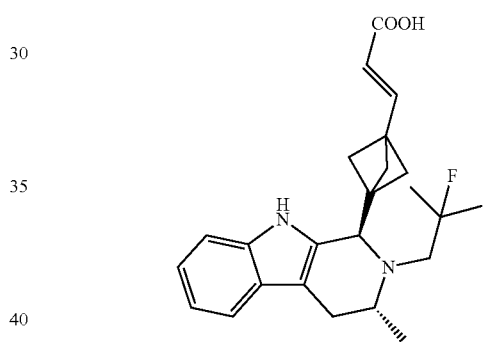

Synthesis of Intermediate 2-fluoro-2-methylpropyl trifluoromethanesulfonate

Step 1

To a stirred solution of ethyl 2-fluoro-2-methylpropanoate (500 mg, 3.72 mmol) in diethyl ether (10 mL) was added lithium aluminium hydride (352 mg, 9.28 mmol) at 0° C. The reaction was stirred at room temperature for 16 h and quenched with 0.3 mL of 15% aqueous NaOH solution at 0° C., followed by 1 mL of water. The mixture was stirred at room temperature for 20 min and filtered through a Celite pad which was washed with diethyl ether (10 mL). The filtrate was concentrated (bath temperature 30° C.) to afford 2-fluoro-2-methylpropan-1-ol (210 mg, 61% yield) as colorless liquid which was used without further purification.

Step 2

To a stirred solution of 2-fluoro-2-methylpropan-1-ol (12 g, 130 mmol) in dichloromethane (120 mL) was added 2,6-lutidine (16.6 g, 155 mmol) and the mixture was cooled to −78° C. Trifluoromethane sulfonic anhydride (25.7 mL, 155 mmol) was added and the reaction was stirred at room temperature for 2 h. The reaction mixture was quenched with ice water (200 mL) and extracted with dichloromethane (2×500 mL). The combined organic layers were washed with water (4×300 mL) and dried over sodium sulfate and concentrated to get a crude red oil. The crude compound was purified by fractional distillation (bath temperature 80° C. to 100° C. at 5 mbar) to afford 2-fluoro-2-methylpropyl trifluoromethanesulfonate (4.8 g, 16% yield) as a colorless liquid. $^1$H NMR (400 MHz, CDCl$_3$) δ=4.41 (d, J=18 Hz, 2H), 1.46 (d, J=21.2 Hz, 6H).

Synthesis of Intermediate (R)-1-(1H-indol-3-yl)propan-2-amine

Step 1

To a stirred suspension of LAH (37.3 g, 984 mmol), in dry THF (2.5 L) was added L-tryptophan (50 g, 245 mmol) at 0° C. and heated at 65° C. for 18 h. To the reaction mixture was added saturated aqueous Na$_2$SO$_4$ solution (300 mL) at 0° C. The resulting suspension was filtered through a celite pad. The pad was washed with EtOAc (2 L) and the combined organics dried over Na$_2$SO$_4$, filtered and evaporated under reduced pressure to afford (S)-2-amino-3-(1H-indol-3-yl)propan-1-ol (45.3 g) as yellow thick liquid. This compound was used directly in the next step without further purification. (45.3 g, 97% yield). MS (ESI) m/z 191.22 [M+H]$^+$.

Step 2

Benzyl chloroformate (41.2 g, 241 mmol) was added dropwise to a suspension of Na$_2$CO$_3$ (43.1 g, 407 mmol) and (S)-2-amino-3-(1H-indol-3-yl)propan-1-ol (45 g, 237 mmol) in a 1:1 solution of water and acetone (2 L) at 0° C. After addition, the cooling bath was removed and the resulting reaction mixture was stirred at rt for 4 h. The reaction mixture was cooled to 0° C., slowly acidified to pH~2 with concentrated HCl, diluted with water and then extracted with ethyl acetate (3×). The combined organic layer was dried over Na$_2$SO$_4$, filtered and evaporated under reduced pressure to obtain the crude product which was purified by flash column chromatography (SiO$_2$, 40 to 70% EtOAc/Hexane) to afford benzyl (S)-(1-hydroxy-3-(1H-indol-3-yl)propan-2-yl)carbamate as a yellow thick liquid. (38 g, 49% yield). MS (ESI) m/z 324.93 [M+H]$^+$.

Step 3 p-Toluenesulfonyl chloride (21.2 g, 111 mmol) was added to a solution of benzyl (S)-(1-hydroxy-3-(1H-indol-3-yl)propan-2-yl)carbamate (34 g, 105 mmol) and TEA (20.7 g, 204 mmol) in dry DCM (350 mL) at 0° C. After addition, the cooling bath was removed and the resulting reaction mixture was stirred at room temperature for 16 h. Solvent was evaporated under reduced pressure. The crude residue was purified by flash column chromatography (SiO$_2$, 30 to 50% EtOAc/Hexane) to afford (S)-2-(((benzyloxy)carbonyl)amino)-3-(1H-indol-3-yl)propyl 4-methylbenzenesulfonate as a pale brown solid. (42 g, 83% yield). MS (ESI) m/z 479.16 [M+H]$^+$.

Step 4

To a stirred solution of compound (S)-2-(((benzyloxy)carbonyl)amino)-3-(1H-indol-3-yl)propyl 4-methylbenzenesulfonate (42 g, 87.8 mmol) in absolute ethanol (2.9 L) was added Pd(OH)$_2$ (5.18 g, 36.9 mmol) and the resulting reaction mixture was stirred an atmosphere of hydrogen gas (150 psi) for 5 h. The mixture was filtered through a Celite pad and the pad was washed with EtOAc (1.5 L) and evaporated under reduced pressure. The crude product was further purified by flash column chromatography (SiO$_2$, 15% methanol/5% NH$_4$OH in DCM) to afford (R)-1-(1H-indol-3-yl)propan-2-amine as off white solid. (4.3 g, 28% yield). $^1$H NMR (300 MHz, DMSO-d$_6$) δ 10.79 (s, 1H), 7.51 (d, J=7.8 Hz, 1H), 7.32 (d, J=7.8 Hz, 1H), 7.11 (d, J=2.1 Hz, 1H), 7.04 (ddd, J=0.9 Hz, 6.9 Hz, 8.1 Hz, 1H), 6.95 (ddd, J=1.2 Hz, 6.9 Hz, 7.8 Hz, 1H), 3.15-3.02 (m, 1H), 2.63 (d, J=6.6 Hz, 2H), 1.82-1.59 (br s 2H), 0.98 (d, J=6.3 Hz, 3H); MS (ESI) m/z 174.24 [M+H]+; [α]$_D$=−34.2° (c=0.5, MeOH).

Synthesis of Intermediate ethyl (E)-3-(3-formylbicyclo[1.1.1]pentan-1-yl)acrylate Step 1

To a suspension of 3-(methoxycarbonyl)bicyclo[1.1.1]pentane-1-carboxylic acid (12 g, 70.5 mmol) in dry THF (200 mL) was added BH$_3$-THF (84 mL, 84.0 mmol, 1.0M in THF) dropwise under argon at 0° C. The mixture was stirred at the same temperature for 1 h. A standard aqueous workup and column purification (SiO$_2$, EtOAc/Hexanes) provided 10.1 g (Yield: 91%) of methyl 3-(hydroxymethyl)bicyclo[1.1.1]pentane-1-carboxylate of the formula

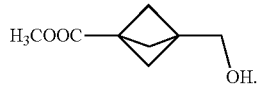

Step 2

To a suspension of methyl 3-(hydroxymethyl)bicyclo[1.1.1]pentane-1-carboxylate (9 g, 57.7 mmol) in dry DCM (200 mL) was added imidazole (7.8 g, 114 mmol) and TBDMS-Cl (10.3 g, 68.3 mmol) at 0° C. The reaction was allowed to stir at rt for 2 h. Standard aqueous work-up and column purification (SiO$_2$, EtOAc/Hexanes) provided 14.5 g (Yield: 93%) of methyl 3-(((tert-butyldimethylsilyl)oxy)methyl)bicyclo[1.1.1]pentane-1-carboxylate of the formula

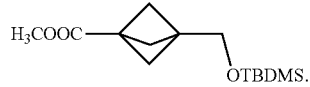

Step 3

To a suspension of methyl 3-(((tert-butyldimethylsilyl)oxy)methyl)bicyclo[1.1.1]pentane-1-carboxylate (7 g, 25.9 mmol) in dry toluene (70 mL) was added DIBAL-H (31.1 mL, 31.1 mmol, 1M in toluene) at −78° C. followed by stirring for 1 h at the same temperature. Standard aqueous work-up followed by column purification (SiO$_2$, EtOAc/Hexanes) provided 4.7 g (Yield: 75%) of 3-(((tert-butyldimethylsilyl)oxy)methyl)bicyclo[1.1.1]pentane-1-carbaldehyde of the formula

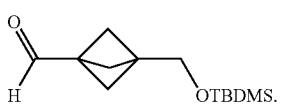 [SMILES: CC(C)(C)[Si](C)(C)OCC12CC(C=O)(C1)C2]

Step 4

To a stirred suspension of 3-(((tert-butyldimethylsilyl)oxy)methyl)bicyclo[1.1.1]pentane-1-carbaldehyde (5 g, 20.8 mmol) in 45 mL of dry THF, NaH (1.01 g, 31.2 mmol) was added at 0° C. The reaction was stirred at rt for 1 h. Ethyl 2-(diethoxyphosphoryl)acetate (3.74 g, 14.5 mmol) was added at 0° C. The mixture was allowed to stir at rt for 3 h. Standard aqueous work-up and column purification (SiO$_2$, EtOAc/Hexanes) provided 3 g (Yield: 42%) of ethyl (E)-3-(3-(((tert-butyldimethylsilyl)oxy)methyl)bicyclo[1.1.1]pentan-1-yl)acrylate of the formula

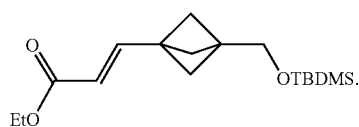 [SMILES: CCOC(=O)/C=C/C12CC(CO[Si](C)(C)C(C)(C)C)(C1)C2]

Step 5

To a stirred solution of ethyl (E)-3-(3-(((tert-butyldimethylsilyl)oxy)methyl)bicyclo[1.1.1]pentan-1-yl)acrylate (0.6 g, 1.93 mmol) in dry THF (10 mL) at 0° C. was added TBAF (1.0 g, 3.86 mmol). The mixture was stirred at rt for 18 h. Standard aqueous work-up and column purification (SiO$_2$, EtOAc/Hexanes) provided 195 mg (Yield: 54%) of ethyl (E)-3-(3-(hydroxymethyl)bicyclo[1.1.1]pentan-1-yl)acrylate of the formula

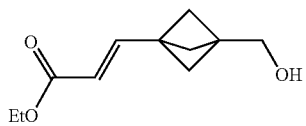 [SMILES: CCOC(=O)/C=C/C12CC(CO)(C1)C2]

as a colorless liquid.

Step 6

To a stirred solution of ethyl (E)-3-(3-(hydroxymethyl)bicyclo[1.1.1]pentan-1-yl)acrylate (195 mg, 0.994 mmol) in DCM (8 mL) was added Dess-Martin periodinane (84 mg, 1.99 mmol) at 0° C. The resulting mixture was stirred rt for 2 h. Standard aqueous work-up and column purification (SiO$_2$, EtOAc/Hexanes) provided 135 mg (Yield: 77%) of ethyl (E)-3-(3-formylbicyclo[1.1.1]pentan-1-yl)acrylate of the formula

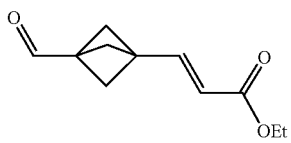 [SMILES: CCOC(=O)/C=C/C12CC(C=O)(C1)C2]

as a colorless liquid. $^1$H NMR (400 MHz, CDCl$_3$) δ 9.60 (s, 1H), 6.94 (d, J=15.6 Hz, 1H), 5.82 (d, J=15.6 Hz, 1H), 4.20 (q, J=4.0 Hz, 2H), 2.16 (s, 6H), 1.30 (t, J=4.0 Hz, 3H).

Synthesis of Compound 1A

Step 1

To a stirred solution of (R)-1-(1H-indol-3-yl)propan-2-amine (2 g, 11.4 mmol) in dioxane (10 mL) was added 2-fluoro-2-methylpropyl trifluoromethanesulfonate (2.55 g, 11.4 mmol) and N,N-diisopropylethylamine (3.08 mL, 17.4 mmol). The mixture was stirred at 90° C. for 3 h and then diluted with ethyl acetate (10 mL) and washed with saturated aqueous NaHCO$_3$ solution (10 mL). The combined organics were dried over sodium sulfate, filtered and concentrated. The resultant residue was purified by column chromatography (SiO$_2$, 40-50% EtOAc/Hexane) to afford 2.19 g (76% yield) of (R)—N-(1-(1H-indol-3-yl)propan-2-yl)-2-fluoro-2-methylpropan-1-amine. MS (ESI) m/z 249.14 [M+H]$^+$.

Step 2

To a stirred solution of (R)—N-(1-(1H-indol-3-yl)propan-2-yl)-2-fluoro-2-methylpropan-1-amine (250 mg, 1.06 mmol) and ethyl (E)-3-(3-formylbicyclo[1.1.1]pentan-1-yl)acrylate in 5 ml of toluene was added acetic acid (64 mg, 1.01 mmol) and the mixture was stirred at 90° C. for 5 h. The reaction mixture was diluted with ethyl acetate (10 mL) and washed with saturated aqueous NaHCO$_3$ solution (10 mL). The combined organics were dried over sodium sulfate, concentrated and the resultant residue was purified by column chromatography (SiO$_2$, 10-12% EtOAc/Hexanes) to afford 200 mg (47% yield) of ethyl (E)-3-(3-((1R,3R)-2-(2-fluoro-2-methylpropyl)-3-methyl-2,3,4,9-tetrahydro-1H-pyrido[3,4-b]indol-yl)bicyclo[1.1.1]pentan-1-yl)acrylate. MS (ESI$^+$) m/z 425.33 [M+H]$^+$.

Step 3

To a stirred solution of ethyl (E)-3-(3-((1R,3R)-2-(2-fluoro-2-methylpropyl)-3-methyl-2,3,4,9-tetrahydro-1H-pyrido[3,4-b]indol-1-yl)bicyclo[1.1.1]pentan-1-yl)acrylate (220 mg, 0.438 mmol) in methanol/THF (1:1, 2 mL) was added 7.5 M aqueous NaOH solution (0.2 mL) at 0° C. The mixture was stirred at 0° C. for 5 h. The resulting reaction mixture was concentrated. The residue was acidified with saturated sodium hydrogen sulfate at 0° C. to pH 5. The precipitate was filtered, washed with water and dried to afford 45 mg (22% yield) of (E)-3-(3-((1R,3R)-2-(2-fluoro-2-methylpropyl)-3-methyl-2,3,4,9-tetrahydro-1H-pyrido[3,4-b]indol-1-yl)bicyclo[1.1.1]pentan-1-yl)acrylic acid as an off white solid. $^1$H NMR (400 MHz, DMSO-d$_6$) δ 12.2 (br s 1H), 10.5 (s, 1H), 7.35 (d, J=8.0 Hz, 1H), 7.27 (d, J=7.6 Hz, 1H), 7.02 (t, J=7.2 Hz, 1H), 6.93 (t, J=6.8 Hz, 1H), 6.81 (s, J=15.6 Hz, 1H), 5.64 (d, J=15.2 Hz, 1H), 3.88 (s, 1H), 3.32-3.21 (m, 1H), 2.67-2.21 (m, 4H), 1.87-1.80 (m, 3H), 1.79-1.77 (m, 3H), 1.41-1.35 (m, 3H), 1.27-1.12 (m, 3H), 1.17-1.16 (m, 3H); MS (ESI$^+$) m/z 397.34 [M+H]$^+$.

Example 1B (E)-3-(3-((1S,3R)-2-(2-Fluoro-2-methylpropyl)-3-methyl-2,3,4,9-tetrahydro-1H-pyrido[3,4-b]indol-1-yl)bicyclo[1.1.1]pentan-1-yl)acrylic acid (1B)

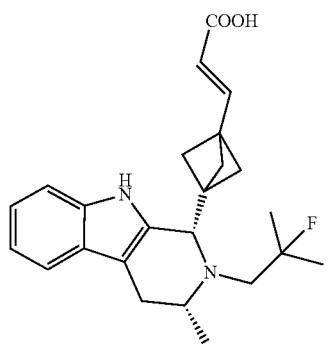 [SMILES: C[C@@H]1Cc2c([nH]c3ccccc23)[C@H](C23CC(/C=C/C(=O)O)(C2)C3)N1CC(C)(C)F]

Step 1

To a stirred solution of (R)-1-(1H-indol-3-yl)propan-2-amine (300 mg, 1.72 mmol) and ethyl (E)-3-(3-formylbicyclo[1.1.1]pentan-1-yl)acrylate (334 mg, 1.72 mmol) in toluene (5 mL) was added acetic acid (220 mg, 3.34 mmol) followed by stirring at 90° C. for 5 h. The reaction mixture was diluted with ethyl acetate (50 mL) and washed with saturated aqueous NaHCO$_3$ solution (30 mL). The combined organic layer was dried over sodium sulfate, filtered and concentrated. The residue was purified by column chromatography (SiO$_2$, 5-7% MeOH in DCM) to afford 350 mg (74% yield) of ethyl (E)-3-(3-((3R)-3-methyl-2,3,4,9-tetrahydro-1H-pyrido[3,4-b]indol-1-yl)bicyclo[1.1.1]pentan-1-yl)acrylate as a 1.2:1.0 mixture of trans/cis isomers. MS (ESI) m/z 351.23 [M+H]$^+$.

Step 2

To a stirred solution of ethyl (E)-3-(3-((3R)-3-methyl-2,3,4,9-tetrahydro-1H-pyrido[3,4-b]indol-1-yl)bicyclo[1.1.1]pentan-1-yl)acrylate (0.35 g, 1 mmol) in dioxane (10 mL) was added 2-fluoro-2-methylpropyl trifluoromethanesulfonate (0.246 g, 1.1 mmol), N,N-diisopropylethylamine (258 mg, 17.4 mmol) and potassium iodide. The reaction was stirred at 130° C. for 4 h in a microwave oven and then diluted with ethyl acetate (50 mL). The combined organics were dried over sodium sulfate and concentrated. The resultant residue was purified by column chromatography (SiO$_2$, using 45-50% ethyl acetate in pet-ether) to afford 0.26 g (61% yield) of ethyl (E)-3-(3-((3R)-2-(2-fluoro-2-methylpropyl)-3-methyl-2,3,4,9-tetrahydro-1H-pyrido[3,4-b]indol-1-yl)bicyclo[1.1.1]pentan-1-yl)acrylate. MS (ESI) m/z 425.2 [M+H]$^+$.

Step 3

To a stirred solution of ethyl (E)-3-(3-((3R)-2-(2-fluoro-2-methylpropyl)-3-methyl-2,3,4,9-tetrahydro-1H-pyrido[3,4-b]indol-1-yl)bicyclo[1.1.1]pentan-1-yl)acrylate (250 mg, 0.587 mmol) in methanol (0.6 mL) and THF (0.6 ml) was added 7.5 M aqueous NaOH (94 mg 2.35 mmol) solution at 0° C. and stirred at rt for 18 h. The reaction mixture was concentrated under reduced pressure. The obtained residue was acidified with 1N HCl at 0° C., extracted with ethyl acetate (3×50 mL) and the combined organic layers were dried over Na$_2$SO$_4$, filtered and evaporated under reduced pressure. The obtained residue was purified by SFC (Column/dimensions: Chiralcel OJ-H (250×4.6 mm), 5 m; % CO$_2$: 60.0; % Co-solvent: 40.0 (100% Methanol); Total Flow: 70.0 g/min; Back Pressure: 100.0 bar; UV: 228 nm; Stack time: 6.5 min; Load/Inj: 11 mg; Solubility: Methanol; Total No of injections: 25; Instrument details: Make/Model: Thar SFC-80) to afford 42 mg (18% yield) of (E)-3-(3-((1S,3R)-2-(2-fluoro-2-methylpropyl)-3-methyl-2,3,4,9-tetrahydro-1H-pyrido[3,4-b]indol-1-yl)bicyclo[1.1.1]pentan-1-yl)acrylic acid as an off white solid. $^1$H NMR (400 MHz, DMSO-d$_6$) δ=12.4-11.8 (br s, 1H), 10.3 (s, 1H), 7.36 (d, J=12.4 Hz, 1H), 7.34 (d, J=12.4 Hz, 1H), 7.10-6.90 (m, 2H), 6.80 (d, J=15.2 Hz, 1H), 5.65 (d, J=15.2 Hz, 1H), 3.91 (s, 1H), 3.31-3.15 (m, 1H), 2.95-2.65 (m, 3H), 2.37 (d, J=14.8 Hz, 1H), 1.93 (d, J=9.2 Hz, 3H), 1.84 (d, J=9.6 Hz, 3H), 1.45-1.22 (m, 6H), 1.10 (d, J=6.8 Hz, 3H); MS (ESI) m/z 397.34 [M+H]$^+$.

Example 2A (E)-3-(4-((1R,3R)-2-((3,3-Difluorocyclobutyl)methyl)-3-methyl-2,3,4,9-tetrahydro-1H-pyrido[3,4-b]indol-1-yl)-3,5-difluorophenyl)acrylic acid (2A)

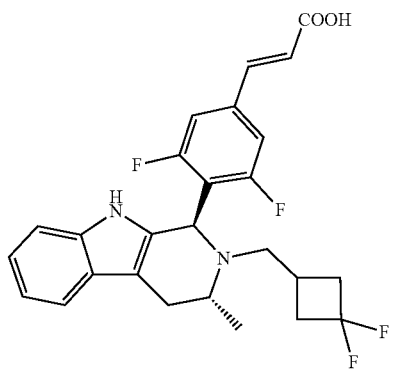 [SMILES: C[C@@H]1Cc2c([nH]c3ccccc23)[C@@H](c2c(F)cc(/C=C/C(=O)O)cc2F)N1CC1CC(F)(F)C1]

Step 1

4-Bromo-2,6-difluorobenzaldehyde (3 g, 13.6 mmol) and methyl acrylate (1.84 mL, 20.4 mmol) were dissolved in thoroughly degassed N,N-dimethylacetamide. Tri-o-tolylphosphine (0.413 g, 1.36 mmol), palladium(II) acetate (0.152 g, 0.678 mmol) and triethylamine (3.7 mL, 27.1 mmol) were added and the reaction was stirred at 80° C. for 6 h. The reaction mixture was cooled, filtered through a Celite pad which was washed with methanol (20 mL). The filtrate was concentrated under reduced pressure. The crude compound was purified by column chromatography (SiO$_2$, 10% EtOAc/Hexanes) to afford 2.5 g (81% Yield) of methyl (E)-3-(3,5-difluoro-4-formylphenyl)acrylate as a pale yellow solid. MS (ESI) m/z 227.08 [M+H]$^+$.

Step 2

To a stirred suspension of 3,3-difluorocyclobutanecarboxylic acid (781 mg, 5.75 mmol) in dry THF (20 mL) was added propylphosphonic anhydride (10.4 mL, 17.2 mmol, 50% wt/wt in EtOAc) and DIPEA (3 mL, 17.2 mmol) at 0°

C. The mixture was stirred for 20 min at the same temperature followed by the addition of (R)-1-(1H-indol-3-yl)propan-2-amine (1 g, 5.75 mmol) at 0° C. and the reaction was stirred for 16 h at room temperature. The reaction mixture was diluted with ice cold water and extracted with EtOAc (2×50 mL). The combined organic layer was dried over Na₂SO₄, filtered and evaporated under reduced pressure. The crude product was purified by flash column chromatography (SiO₂, 20% EtOAc/Hexane) to give 1.2 g (72% yield) of (R)—N-(1-(1H-indol-3-yl)propan-2-yl)-3,3-difluorocyclobutane-1-carboxamide as a light brown solid. MS (ESI) m/z 293 [M+H]⁺.

Step 3

To a stirred suspension of (R)—N-(1-(1H-indol-3-yl)propan-2-yl)-3,3-difluorocyclobutane-1-carboxamide (1.24 g, 4.11 mmol) in dry THF (30 mL) was added LAH (780 mg, 20.5 mmol) portion wise at 0° C. and the reaction was then stirred at reflux for 14 h. The reaction mixture was quenched with ice cold water (50 mL) and extracted with EtOAc (2×50 mL). The combined organics were dried over Na₂SO₄, filtered and evaporated under reduced pressure to afford the crude material which was purified by flash column chromatography (SiO₂, 80% EtOAc/Hexane) to provide 1 g (88% yield) of (R)—N-((3,3-difluorocyclobutyl)methyl)-1-(1H-indol-3-yl)propan-2-amine as an off white solid. MS (ESI) m/z 279 [M+H]⁺.

Step 4

To a stirred solution of (R)—N-((3,3-difluorocyclobutyl)methyl)-1-(1H-indol-3-yl)propan-2-amine (800 mg, 2.88 mmol) in toluene (8 mL) was added methyl (E)-3-(3,5-difluoro-4-formylphenyl)acrylate (650 mg, 2.88 mmol) and acetic acid (345 mg, 5.76 mmol). The resulting mixture was stirred at 90° C. for 5 h. The reaction mixture was diluted with water and extracted with ethyl acetate (2×50 mL). The combined organic layer was dried over Na₂SO₄, filtered and evaporated under reduced pressure to afford 800 mg (57% yield) of crude methyl (E)-3-(4-((1R,3R)-2-((3,3-difluorocyclobutyl)methyl)-3-methyl-2,3,4,9-tetrahydro-1H-pyrido[3,4-b]indol-1-yl)-3,5-difluorophenyl)acrylate as a yellow solid which was used without further purification (cis/trans: 1:8); MS (ESI) m/z 487.2 [M+H]⁺.

Step 5

To a stirred solution of methyl (E)-3-(4-((1R,3R)-2-((3,3-difluorocyclobutyl)methyl)-3-methyl-2,3,4,9-tetrahydro-1H-pyrido[3,4-b]indol-1-yl)-3,5-difluorophenyl)acrylate (230 mg, 0.473 mmol) in THF:methanol (5 mL, 4:1) was added a 7.5M aqueous solution of NaOH (56 mg 1.42 mmol) at 0° C. and the mixture was stirred at rt for 5 h. The reaction mixture was concentrated under reduced pressure to remove methanol. The obtained residue was acidified with 1N HCl at 0° C. The reaction mixture was diluted with EtOAc and washed with water. The combined organics were dried over sodium sulfate and concentrated to provide the crude product which was purified by preparative SFC to afford 95 mg (42% yield) of (E)-3-(4-((1R,3R)-2-((3,3-difluorocyclobutyl)methyl)-3-methyl-2,3,4,9-tetrahydro-1H-pyrido[3,4-b]indol-1-yl)-3,5-difluorophenyl)acrylic acid as off white solid. ¹H NMR (300 MHz, DMSO-d₆) δ 10.59 (s, 1H), 7.60-7.39 (m, 4H), 7.19 (d, J=7.5 Hz, 1H), 7.08-6.90 (m, 2H), 6.67 (d, J=15.9 Hz, 1H), 5.14 (s, 1H), 3.50-3.16 (m, 1H), 2.90-2.70 (m, 2H), 2.63-2.46 (m, 3H), 2.46-2.25 (m, 2H), 2.22-2.15 (m, 1H), 2.05-1.82 (m, 1H), 1.06 (d, J=6.0, 3H); MS (ESI) m/z 473.2 [M+H]⁺. [α]_D=−79.2° (c 0.25, CHCl₃).

Example 3A (E)-3-(3,5-Difluoro-4-((1R,3R)-3-methyl-2-((3-(trifluoromethyl)bicyclo[1.1.1]pentan-1-yl)methyl)-2,3,4,9-tetrahydro-1H-pyrido[3,4-b]indol-1-yl)phenyl)acrylic acid (3A)

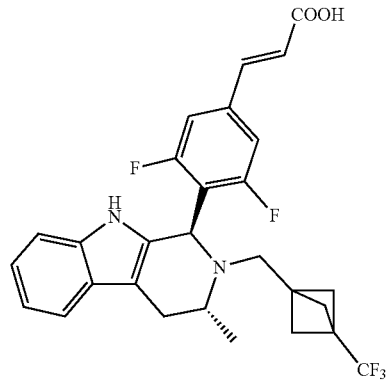 [SMILES: C[C@@H]1Cc2c([nH]c3ccccc23)[C@@H](c2c(F)cc(/C=C/C(=O)O)cc2F)N1CC12CC(C(F)(F)F)(C1)C2]

Step 1

To a stirred suspension of (R)-1-(1H-indol-3-yl)propan-2-amine (200 mg, 1.11 mmol) in dry THF (4 mL) was added propylphosphonic anhydride (2 mL, 3.35 mmol, 50% wt/wt in EtOAc) and DIPEA (0.6 mL, 3.35 mmol) at 0° C. The mixture was stirred for 20 min at 0° C. and then 3-(trifluoromethyl)bicyclo[1.1.1]pentane-1-carboxylic acid (213 mg, 1.22 mmol) was added at 0° C. The reaction was allowed to stir at rt for 16 h. The reaction mixture was diluted with ice cold water and extracted with ethyl acetate (2×50 mL). The combined organic layers were dried over sodium sulfate, filtered and concentrated. The resultant residue was purified by flash column chromatography (SiO₂, 20% EtOAc/Hexane) to afford 200 mg (64% yield) of (R)—N-(1-(1H-indol-3-yl)propan-2-yl)-3-(trifluoromethyl)bicyclo[1.1.1]pentane-1-carboxamide as a pale brown solid. MS (ESI) m/z; 337.36 [M+H]⁺.

Step 2

To a stirred suspension of (R)—N-(1-(1H-indol-3-yl)propan-2-yl)-3-(trifluoromethyl)bicyclo[1.1.1]pentane-1-carboxamide (200 mg, 0.595 mmol) in dry THF (5 mL) was added LAH (135 mg, 3.57 mmol) portionwise at 0° C. and the mixture was heated at reflux for 14 h. Ice water (50 mL) was added and the mixture was extracted with EtOAc (2×50 mL). The combined organic layer was dried over sodium sulfate, filtered and concentrated. The resultant residue was purified by flash column chromatography (SiO₂, 80% EtOAc/Hexane) to afford 150 mg (78% yield) of (R)-1-(1H-indol-3-yl)-N-((3-(trifluoromethyl)bicyclo[1.1.1]pentan-1-yl)methyl)propan-2-amine as an off white solid. MS (ESI) m/z 323.23 [M+H]⁺.

Step 3

To a stirred solution of (R)-1-(1H-indol-3-yl)-N-((3-(trifluoromethyl)bicyclo[1.1.1]pentan-1-yl)methyl)propan-2- amine (150 mg, 0.465 mmol) in toluene (3 mL) was added methyl (E)-3-(3,5-difluoro-4-formylphenyl)acrylate (126 mg, 0.55 mmol) and acetic acid (55 mg, 0.931 mmol). The resulting mixture was stirred at 90° C. for 5 h. The reaction mixture was diluted with water and extracted with ethyl acetate (2×50 mL). The combined organics were dried over Na$_2$SO$_4$, filtered and evaporated under reduced pressure to afford the crude product which was purified by flash column chromatography (SiO$_2$, 15% EtOAc/hexane) to afford 140 mg (56% yield) of methyl (E)-3-(3,5-difluoro-4-((1R,3R)-3-methyl-2-((3-(trifluoromethyl)bicyclo[1.1.1]pentan-1-yl)methyl)-2,3,4,9-tetrahydro-1H-pyrido[3,4-b]indol-1-yl)phenyl)acrylate as an off white solid. MS (ESI) m/z 531.35 [M+H]$^+$.

Step 4

To a stirred solution of methyl (E)-3-(3,5-difluoro-4-((1R,3R)-3-methyl-2-((3-(trifluoromethyl)bicyclo[1.1.1]pentan-1-yl)methyl)-2,3,4,9-tetrahydro-1H-pyrido[3,4-b]indol-1-yl)phenyl)acrylate (140 mg, 0.26 mmol) in THF:methanol (5 mL, 4:1) was added 7.5 M aqueous NaOH (0.10 mL, 0.79 mmol) solution at 0° C. and the mixture was stirred at rt for 5 h. Concentration afforded a residue which was acidified with 1N HCl at 0° C. and extracted with EtOAc (3×50 mL). The combined organics were dried over Na$_2$SO$_4$, filtered and evaporated under reduced pressure. The crude product was further purified by SFC to afford 50 mg (37% yield) of (E)-3-(3,5-difluoro-4-((1R,3R)-3-methyl-2-((3-(trifluoromethyl)bicyclo[1.1.1]pentan-1-yl)methyl)-2,3,4,9-tetrahydro-1H-pyrido[3,4-b]indol-1-yl)phenyl)acrylic acid as a pale yellow solid. $^1$H NMR (400 MHz, DMSO-d$_6$) δ 12.58 (br s 1H), 10.55 (s 1H), 7.53 (d, J=16 Hz, 1H), 7.48 (d, J=10.8 Hz, 2H), 7.41 (d, J=7.8 Hz, 1H), 7.18 (d, J=7.8 Hz, 1H), 7.02-6.92 (m, 2H), 6.68 (d, J=15.9 Hz, 1H), 5.12 (s, 1H), 3.42-3.28 (m, 1H), 2.95 (dd, J=14.7 Hz, 4.2 Hz, 1H), 2.83 (d, J=14.4 Hz, 1H), 2.59 (d, J=16.8 Hz, 1H), 2.37 (d, J=14.4 Hz, 1H), 1.75 (d, J=9.3 Hz, 3H), 1.63 (d, J=9.3 Hz, 3H), 1.07 (d, J=6 Hz, 3H); MS (ESI) m/z 517.32 [M+H]$^+$. [α]$_D$=−70.0° (c=0.5, MeOH, 25° C.).

Examples 4A and 4B (E)-3-(3,5-Difluoro-4-((1R,3R)-3-methyl-2-(3-(trifluoromethyl)bicyclo[1.1.1]pentan-1-yl)-2,3,4,9-tetrahydro-1H-pyrido[3,4-b]indol-1-yl)phenyl)acrylic acid (4A)

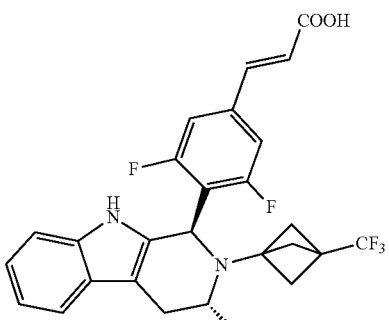

(E)-3-(3,5-Difluoro-4-((1S,3S)-3-methyl-2-(3-(trifluoromethyl)bicyclo[1.1.1]pentan-1-yl)-2,3,4,9-tetrahydro-1H-pyrido[3,4-b]indol-1-yl)phenyl)acrylic acid (4B)

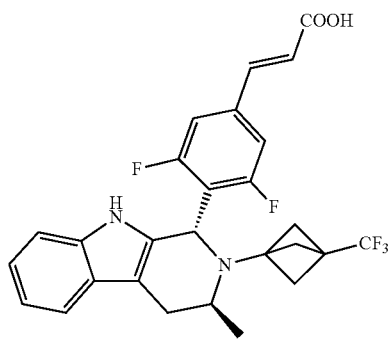 [SMILES: C[C@H]1Cc2c([nH]c3ccccc23)[C@H](c2c(F)cc(/C=C/C(=O)O)cc2F)N1C12CC(C(F)(F)F)(C1)C2]

Step 1

To a stirred solution of 1-(1H-indol-3-yl)propan-2-one (0.400 g, 2.31 mmol) in methanol (3 mL) was added 3-(trifluoromethyl)bicyclo[1.1.1]pentan-1-amine (0.518 g, 2.77 mmol) and acetic acid (14 mg, 0.231 mmol) and the mixture was stirred at rt for 16 hours. The resulting solution was cooled to 0° C. and sodium cyanoborohydride (0.290 g, 4.62 mmol) was added followed by additional stirring for 5 h at rt. The reaction was diluted with ethyl acetate (10 mL) and washed with saturated, aqueous NH$_4$Cl solution (10 mL). The combined organic layer was dried over sodium sulfate, filtered and concentrated. The crude residue was purified by column chromatography using (SiO$_2$, 15% EtOAc/Hexane) to afford 0.4 g of N-(1-(1H-indol-3-yl)propan-2-yl)-3-(trifluoromethyl)bicyclo[1.1.1]pentan-1-amine which was used without further purification; MS (ESI) m/z 309.18 [M+H]$^+$.

Step 2

To a stirred solution of N-(1-(1H-indol-3-yl)propan-2-yl)-3-(trifluoromethyl)bicyclo[1.1.1]pentan-1-amine (1.2 g, 3.90 mmol) in toluene (6 mL) was added methyl (E)-3-(3,5-difluoro-4-formylphenyl)acrylate (0.880 g, 3.90 mmol) and acetic acid (0.467 g, 7.79 mmol). The resulting mixture was stirred at 90° C. for 5 h. The reaction mixture was diluted with EtOAc and washed with water. The combined organic phase was dried over sodium sulfate, filtered and concentrated. The residue was purified by chiral SFC (Chiralcel OD-H (5 μm, 250×21 mm) % CO$_2$: 85.0%, % Co-solvent (EtOH): 15.0%; Total Flow: 60.0 g/min; Back Pressure: 100.0 bar; UV: 220 nm; Stack time: 5.5 min; Load/Inj: 2.8 mg; Solubility: MeOH; Total number of injections: 35; Instrument details: Make/Model: Thar SFC-80) to afford 180 mg (9% yield) of methyl (E)-3-(3,5-difluoro-4-((1R,3R)-3-methyl-2-(3-(trifluoromethyl)bicyclo[1.1.1]pentan-1-yl)-2,3,4,9-tetrahydro-1H-pyrido[3,4-b]indol-1-yl)phenyl)acrylate (designated as PEAK-1) and 180 mg (9% yield) of methyl (E)-3-(3,5-difluoro-4-((1S,3S)-3-methyl-2-(3-(trifluoromethyl)bicyclo[1.1.1]pentan-1-yl)-2,3,4,9-tetrahydro-1H-pyrido[3,4-b]indol-1-yl)phenyl)acrylate (designated as PEAK-2). Methyl (E)-3-(3,5-difluoro-4-((1R,3R)-3-methyl-2-(3-(trifluoromethyl)bicyclo[1.1.1]pentan-1-yl)-2,3,4,9-tetrahydro-1H-pyrido[3,4-b]indol-1-yl)phenyl)acrylate: MS (ESI) m/z 517.18 [M+H]⁺. Methyl (E)-3-(3,5-difluoro-4-((1S,3S)-3-methyl-2-(3-(trifluoromethyl)bicyclo[1.1.1]pentan-1-yl)-2,3,4,9-tetrahydro-1H-pyrido[3,4-b]indol-1-yl)phenyl)acrylate: MS (ESI) m/z 517.18 [M+H]⁺. Note: absolute stereochemistry arbitrarily assigned.

Step 3-a

To a stirred solution of methyl (E)-3-(3,5-difluoro-4-((1R,3R)-3-methyl-2-(3-(trifluoromethyl)bicyclo[1.1.1]pentan-1-yl)-2,3,4,9-tetrahydro-1H-pyrido[3,4-b]indol-1-yl)phenyl)acrylate (180 mg, 0.349 mmol) in methanol (1.5 mL) was added aqueous solution of NaOH (0.13 mL, 0.039 g, 0.988 mmol, 7.5M) at 0° C. and the mixture was stirred at rt for 5 h. The reaction mixture was concentrated under reduced pressure to remove methanol. The residue was acidified with 1N HCl at 0° C., diluted with EtOAc and washed with water. The combined organic layer was dried over sodium sulfate, filtered and concentrated. The crude residue was purified by SFC (Chiralcel OJ-H (5 µm, 250×21 mm); % CO₂: 50.0%; % Co-solvent (EtOH): 50.0%; Total Flow: 60.0 g/min; Back Pressure: 90.0 bar; UV: 220 nm; Stack time: 6.5 min; Load/Inj: 36 mg; Solubility: MeOH; Total Number of injections: 6; Instrument details: Make/Model: Thar SFC-80) to afford 90 mg (55% yield) of (E)-3-(3,5-difluoro-4-((1R,3R)-3-methyl-2-(3-(trifluoromethyl)bicyclo[1.1.1]pentan-1-yl)-2,3,4,9-tetrahydro-1H-pyrido[3,4-b]indol-1-yl)phenyl)acrylic acid as an off white solid. ¹H NMR (300 MHz, DMSO-d₆) δ 10.6 (br s, 1H), 7.62-7.39 (m, 4H), 7.18 (d, J=7.5 Hz, 1H), 7.03-6.92 (m, J=7.2 Hz, 2H), 6.68 (d, J=16.2 Hz, 1H), 5.38 (s, 1H), 3.62 (br s, 1H), 3.05-2.97 (m, 1H), 2.63-2.58 (m, 1H), 2.08-1.79 (m 6H), 1.09 (d, J=6 Hz, 3H); MS (ESI) m/z 503.26 [M+H]⁺. [α]$_D$=−58.4° (c 0.25, CHCl₃, 24° C.).

Step 3-b

To a stirred solution of methyl (E)-3-(3,5-difluoro-4-((1S,3S)-3-methyl-2-(3-(trifluoromethyl)bicyclo[1.1.1]pentan-1-yl)-2,3,4,9-tetrahydro-1H-pyrido[3,4-b]indol-1-yl)phenyl)acrylate (170 mg, 0.329 mmol) in methanol (1.5 mL) was added aqueous NaOH (0.13 mL, 0.988 mmol, 7.5M) at 0° C. and the reaction was stirred at rt for 5 h. The reaction mixture was concentrated under reduced pressure to remove methanol. The residue was acidified with 1N HCl at 0° C. then diluted with EtOAc and washed with water. The combined organic layer was dried over sodium sulfate, filtered and concentrated. The crude residue was purified by SFC (Chiralcel OJ-H (5 am, 250×21 mm); % CO₂: 55.0; % Co-solvent (EtOH): 45.0; Total Flow: 60.0 g/min; Back Pressure: 90.0 bar; UV: 220 nm; Stack time: 6.8 min; Load/Inj: 12 mg; Solubility: MeOH; Total No of injections: 15; Instrument details: Make/Model: Thar SFC-80) to afford 115 mg (70% yield) of (E)-3-(3,5-difluoro-4-((1S,3S)-3-methyl-2-(3-(trifluoromethyl)bicyclo[1.1.1]pentan-1-yl)-2,3,4,9-tetrahydro-1H-pyrido[3,4-b]indol-1-yl)phenyl)acrylic acid as an off white solid. ¹H NMR (300 MHz, DMSO-d₆) δ 10.6 (br s, 1H), 7.62-7.39 (m, 4H), 7.18 (d, J=7.8 Hz, 1H), 7.03-6.92 (m, 2H), 6.68 (d, J=15.2 Hz, 1H), 5.39 (s, 1H), 3.62 (br s, 1H), 3.01-2.95 (m, 1H) 2.63-2.58 (m, 1H), 2.12-1.72 (m, 6H), 1.09 (d, J=6.0 Hz, 3H); MS (ESI): m/z 503.26 [M+H]⁺. [α]$_D$ +42.4 (c 0.25, CHCl₃, 24° C.).

Compounds 4A and 4B are shown above and in Table 1 with absolute stereochemistry arbitrarily assigned.

Example 5A (E)-3-(4-((1R,3R)-2-(Bicyclo[1.1.1]pentan-1-ylmethyl)-3-methyl-2,3,4,9-tetrahydro-1H-pyrido[3,4-b]indol-1-yl)-3,5-difluorophenyl)acrylic acid (5A)

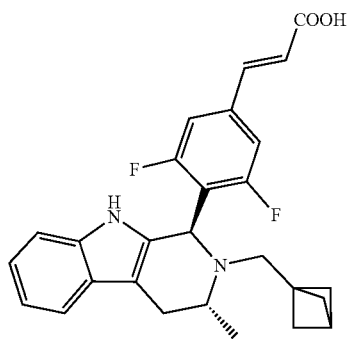 [SMILES: C[C@@H]1Cc2c([nH]c3ccccc23)[C@@H](c2c(F)cc(/C=C/C(=O)O)cc2F)N1CC12CC(C1)C2]

Step 1

To a stirred solution of (R)-1-(1H-indol-3-yl)propan-2-amine (0.500 g, 2.87 mmol) in THF (10 mL) was added propylphosphonic anhydride (2.25 mL, 8.60 mmol, 50% wt/wt in EtOAc) and N,N-diisopropylethylamine (1.5 mL, 8.60 mmol) at rt. The solution was stirred for 10 minutes and then a solution of bicyclo[1.1.1]pentane-1-carboxylic acid (0.375 g, 3.16 mmol) was added and the mixture was stirred at rt for an additional 16 h. Water (3 mL) was added and the reaction mixture was extracted with EtOAc (2×50 mL). The combined organic layers were dried over Na₂SO₄, filtered and evaporated under reduced pressure. The crude product was triturated with ether to obtain 700 mg (90% yield) of (R)—N-(1-(1H-indol-3-yl)propan-2-yl)bicyclo[1.1.1]pentane-1-carboxamide of the formula

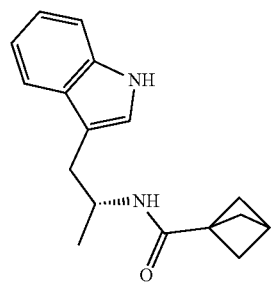 [SMILES: C[C@H](Cc1c[nH]c2ccccc12)NC(=O)C12CC(C1)C2]

as a pale yellow solid. MS (ESI) m/z 269.26 [M+H]⁺.

Step 2

To a stirred solution of (R)—N-(1-(1H-indol-3-yl)propan-2-yl)bicyclo[1.1.1]pentane-1-carboxamide (700 mg, 2.61 mmol) in THF (10 mL) was added LAH (600 mg, 15.7 mmol) portion wise at 0° C. The mixture was heated to reflux for 16 h, cooled to rt and then slowly treated with ice water (50 mL) and extracted with EtOAc (2×50 mL). The combined organic layer was dried over Na₂SO₄, filtered and concentrated under reduced pressure. The crude residue was triturated with ether to obtain 600 mg (90% yield) of semi-pure (R)—N-(bicyclo[1.1.1]pentan-1-ylmethyl)-1-(1H-indol-3-yl)propan-2-amine of the formula

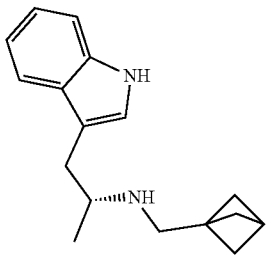 [SMILES: C[C@H](Cc1c[nH]c2ccccc12)NCC12CC(C1)C2]

as a pale yellow solid. MS (ESI) m/z 255.36 [M+H]+.

Step 3

To a stirred solution of semi-pure (R)—N-(bicyclo[1.1.1]pentan-1-ylmethyl)-1-(1H-indol-3-yl)propan-2-amine (600 mg, 2.36 mmol) in toluene (12 mL), methyl (E)-3-(3,5-difluoro-4-formylphenyl)acrylate (540 mg, 2.36 mmol) and acetic acid (285 mg, 4.7 mmol) were added and the mixture was stirred at 90° C. for 12 h. The reaction mixture was neutralized with a saturated aqueous solution of sodium bicarbonate then extracted with EtOAc (2×50 mL). The combined organic layer was dried over Na$_2$SO$_4$, filtered and evaporated under reduced pressure to afford 400 mg (36% yield) of crude methyl (E)-3-(4-((1R,3R)-2-(bicyclo[1.1.1]pentan-1-ylmethyl)-3-methyl-2,3,4,9-tetrahydro-1H-pyrido[3,4-b]indol-1-yl)-3,5-difluorophenyl)acrylate as a mixture of cis/trans isomers. MS (ESI) m/z 463.38 [M+H]+.

Step 4

To a stirred solution of methyl (E)-3-(4-((1R,3R)-2-(bicyclo[1.1.1]pentan-1-ylmethyl)-3-methyl-2,3,4,9-tetrahydro-1H-pyrido[3,4-b]indol-1-yl)-3,5-difluorophenyl)acrylate (400 mg of a mixture of cis/trans isomers, 0.86 mmol) in a mixture of THF/MeOH (6 mL, 5:1) was added an aqueous solution of NaOH (0.5 mL, 1.5M) at 0° C. and the mixture was stirred at rt for 16 h. Standard aqueous work-up and SFC purification provided 140 mg (Yield 37%) of (E)-3-(4-((1R,3R)-2-(bicyclo[1.1.1]pentan-1-ylmethyl)-3-methyl-2,3,4,9-tetrahydro-1H-pyrido[3,4-b]indol-1-yl)-3,5-difluorophenyl)acrylic acid as pale yellow solid: $^1$H NMR (400 MHz, DMSO-d$_6$) δ 12.50 (br s 1H), 10.50 (s, 1H), 7.55 (d, J=16.0 Hz, 1H), 7.46 (d, J=8 Hz, 2H), 7.39 (d, J=8 Hz, 1H), 7.16 (d, J=8 Hz, 1H), 6.99 (dd, J=7.6 Hz, 6.8 Hz, 1H), 6.94 (dd, J=7.6 Hz, 7.2 Hz, 1H), 6.67 (d, J=16 Hz, 1H), 5.08 (s, 1H), 3.45-3.56 (m, 1H), 2.94 (dd, J=12.8 Hz, 4 Hz, 1H), 2.68 (d, J=14 Hz, 1H), 2.56 (dd, J=12 Hz, 0.9 Hz, 1H), 2.37 (s, 1H), 2.24 (d, J=14.8 Hz, 1H), 1.56 (d, J=8.8 Hz, 3H), 1.46 (d, J=9.2 Hz, 3H), 1.00 (d, J=6.4 Hz, 3H); MS (ESI) m/z 449.39 [M+H]+, [α]$_D$ +65.6° (c 0.25, MeOH, 24° C.).

Example 6A (E)-3-(3,5-Difluoro-4-((1R,3R)-3-methyl-2-(tetrahydro-2H-pyran-4-yl)-2,3,4,9-tetrahydro-1H-pyrido[3,4-b]indol-1-yl)phenyl)acrylic acid (6A)

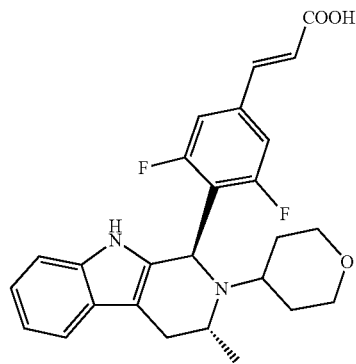 [SMILES: C[C@@H]1Cc2c([nH]c3ccccc23)[C@@H](c2c(F)cc(/C=C/C(=O)O)cc2F)N1C1CCOCC1]

Step 1

To a stirred solution of (R)-1-(1H-indol-3-yl)propan-2-amine (0.5 g, 2.86 mmol) in ethanol (3 mL) was added tetrahydro-4H-furan-4 one (0.27 g 2.86 mmol) and the mixture was heated to 80° C. for 3 h. The resulting reaction mixture was cooled to 0° C. and sodium borohydride (0.216 g, 5.72 mmol) was added. The mixture was stirred at rt for 2 h and then diluted with ethyl acetate (10 mL) and washed with saturated aqueous NH$_4$Cl solution (10 mL) followed by brine. The combined organic layers were dried over sodium sulfate and concentrated under reduced pressure to afford 0.61 g (82% yield) of (R)—N-(1-(1H-indol-3-yl)propan-2-yl)tetrahydro-2H-pyran-4-amine as a colorless gummy liquid. MS (ESI) m/z 259.18 [M+H]+.

Step 2

To a stirred solution of N-(1-(1H-indol-3-yl)propan-2-yl)tetrahydro-2H-pyran-4-amine (0.5 g, 1.93 mmol) in 5 mL of toluene was added methyl (E)-3-(3,5-difluoro-4-formylphenyl)acrylate (0.437 g, 1.94 mmol) and acetic acid (232 mg, 3.87 mmol). The resulting mixture was stirred at 90° C. for 5 h. The reaction mixture was diluted with EtOAc, washed with water, dried over sodium sulfate and concentrated under reduced pressure to afford 220 mg (24% yield) of methyl (E)-3-(3,5-difluoro-4-((1R,3R)-3-methyl-2-(tetrahydro-2H-pyran-4-yl)-2,3,4,9-tetrahydro-1H-pyrido[3,4-b]indol-1-yl)phenyl)acrylate as a pale yellow solid. MS (ESI) m/z 467.31 [M+H]+.

Step 3

To a stirred solution of methyl (E)-3-(3,5-difluoro-4-((1R,3R)-3-methyl-2-(tetrahydro-2H-pyran-4-yl)-2,3,4,9-tetrahydro-1H-pyrido[3,4-b]indol-1-yl)phenyl)acrylate (220 mg, 0.398 mmol) in methanol (2 mL) was added an aqueous solution of NaOH (0.159 mL, 1.19 mmol, 7.5M) solution at 0° C. and stirred at rt for 4 h. The reaction mixture was concentrated under reduced pressure and the residue was acidified with 1N HCl at 0° C. The mixture was extracted with ethyl acetate (3×50 mL) and the combined organic layers were dried over Na$_2$SO$_4$, filtered and evaporated under reduced pressure. The crude product was purified by SFC (Column/dimensions: (R,R)-Whelk-01 (5 μm, 250×30 mm); % $CO_2$: 60.0; % co-solvent (IPA): 40.0; total flow: 70.0 g/min; Back Pressure: 100.0 bar; UV: 224 nm; Stack time: 5.8 min; Load/Inj: 4.2 mg; Solubility: Methanol; Total No of injections: 35; Instrument details: Make/Model: Thar SFC-80) to afford 80 mg (Yield: 46%) of (E)-3-(3,5-difluoro-4-((1R,3R)-3-methyl-2-(tetrahydro-2H-pyran-4-yl)-2,3,4,9-tetrahydro-1H-pyrido[3,4-b]indol-1-yl)phenyl)acrylic acid as an off white solid. $^1$H NMR (400 MHz, DMSO-$d_6$) δ 12.50 (br s 1H), 10.56 (br s 1H), 7.55-7.36 (m, 4H), 7.19 (d, J=8 Hz, 1H), 7.00-6.90 (m. 2H), 6.65 (d, J=16.4 Hz, 1H), 5.50 (s, 1H), 3.89-3.70 (m, 2H), 3.60-3.52 (m, 1H), 3.23-3.12 (m, 2H), 2.94-2.78 (m, 2H), 2.57-2.51 (m, 1H), 1.75-1.50 (m, 3H), 1.34-1.15 (m, 4H); MS (ESI) m/z 453.25 [M+H]$^+$, [t]$_D$=−80.0° (c 0.25, MeOH, 24° C.).

Example 7A (E)-3-(3,5-Difluoro-4-((1R,3R)-3-methyl-2-(oxetan-3-yl)-2,3,4,9-tetrahydro-1H-pyrido[3,4-b]indol-1-yl)phenyl)acrylic acid (7A)

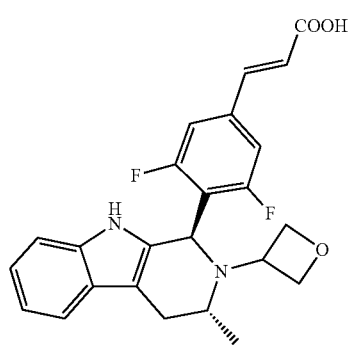 [SMILES: C[C@@H]1Cc2c([nH]c3ccccc23)[C@@H](c2c(F)cc(/C=C/C(=O)O)cc2F)N1C1COC1]

Step 1

To a stirred solution of (R)-1-(1H-indol-3-yl)propan-2-amine (0.8 g, 4.60 mmol) in 3 mL of ethanol was added oxetane-3-one (0.397 g 5.52 mmol) and reaction mixture was stirred at 50° C. for 3 hours. The resulting reaction mixture was cooled to 0° C., treated with sodium borohydride (0.262 g, 6.90 mmol) and stirred for 5 h at room temperature. The mixture was diluted with ethyl acetate (10 mL) and washed with saturated aqueous $NH_4Cl$ solution (10 mL). The combined organic layers were dried over sodium sulfate and concentrated. The crude residue was purified by column chromatography ($SiO_2$, 2-3% methanol/DCM) to afford 0.3 g (28% Yield) of (R)—N-(1-(1H-indol-3-yl)propan-2-yl)oxetan-3-amine as a colorless, gummy liquid. MS (ESI) m/z 231.17 [M+H]$^+$.

Step 2

To a stirred solution of (R)—N-(1-(1H-indol-3-yl)propan-2-yl)oxetan-3-amine (0.300 g, 1.30 mmol) in toluene (3 mL) was added methyl (E)-3-(3,5-difluoro-4-formylphenyl)acrylate (0.353 g, 1.56 mmol) and acetic acid (0.156, 2.61 mmol). The resulting mixture was stirred at 90° C. for 5 h. The reaction mixture was diluted with EtOAc and washed with water. The combined organics were dried over sodium sulfate and concentrated. The residue was purified by reversed phase prep-HPLC to afford 180 mg (32% Yield) of methyl (E)-3-(3,5-difluoro-4-((1R,3R)-3-methyl-2-(oxetan-3-yl)-2,3,4,9-tetrahydro-1H-pyrido[3,4-b]indol-1-yl)phenyl)acrylate as a pale yellow solid. MS (ESI) m/z 439.24 [M+H]$^+$.

Step 3

To a stirred solution of methyl (E)-3-(3,5-difluoro-4-((1R,3R)-3-methyl-2-(oxetan-3-yl)-2,3,4,9-tetrahydro-1H-pyrido[3,4-b]indol-1-yl)phenyl)acrylate (130 mg, 0.296 mmol) in methanol (1.5 mL) was added an aqueous solution of NaOH (35 mg, 0.888 mmol, 7.5M) at 0° C. The mixture was stirred at rt for 5 h. The reaction mixture was concentrated under reduced pressure to remove methanol. The obtained residue was acidified with 1N HCl at 0° C. and then diluted with EtOAc and washed with water. The combined organic layers were dried over sodium sulfate, filtered and concentrated. The residue was triturated with n-pentane to afford 70 mg (56% yield) of (E)-3-(3,5-difluoro-4-((1R,3R)-3-methyl-2-(oxetan-3-yl)-2,3,4,9-tetrahydro-1H-pyrido[3,4-b]indol-1-yl)phenyl)acrylic acid as an off white solid. $^1$H NMR (400 MHz, DMSO-$d_6$) δ 12.6 (br s, 1H), 10.6 (br s, 1H), 7.57-7.39 (m, 4H), 7.19 (d, J=7.2 Hz, 1H), 7.02-6.93 (m, J=7.2 Hz, 2H), 6.68 (d, J=16 Hz, 1H), 5.12 (s, 1H), 4.63 (br s, 1H), 4.52 (br s, 1H), 4.20 (br s, 1H), 3.93 (br s, 2H), 2.93 (d, J=15.2 Hz, 1H), 2.56 (br s, 2H), 1.00 (br s, 3H); MS (ESI) m/z 425.29 [M+H]$^+$.

Examples 8A and 8B (E)-3-(3,5-Difluoro-4-((1R,3R)-3-methyl-2-((S)-tetrahydrofuran-3-yl)-2,3,4,9-tetrahydro-1H-pyrido[3,4-b]indol-1-yl)phenyl)acrylic acid (8A)

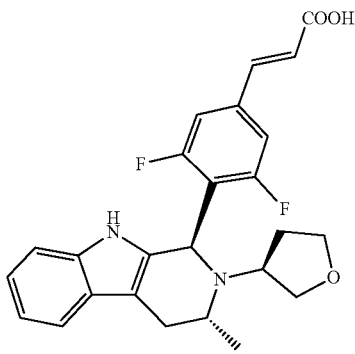 [SMILES: C[C@@H]1Cc2c([nH]c3ccccc23)[C@@H](c2c(F)cc(/C=C/C(=O)O)cc2F)N1[C@H]1CCOC1]

(E)-3-(3,5-Difluoro-4-((1R,3R)-3-methyl-2-((R)-tetrahydrofuran-3-yl)-2,3,4,9-tetrahydro-1H-pyrido[3,4-b]indol-1-yl)phenyl)acrylic acid (8B)

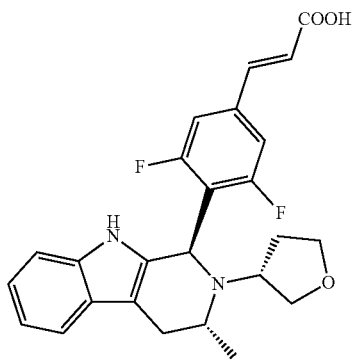 [SMILES: C[C@@H]1Cc2c([nH]c3ccccc23)[C@@H](c2c(F)cc(/C=C/C(=O)O)cc2F)N1[C@@H]1CCOC1]

Step 1

To a stirred solution of (R)-1-(1H-indol-3-yl)propan-2-amine (0.8 g, 4.60 mmol) in ethanol (3 mL) was added dihydrofuran-3(2H)-one (0.474 g, 5.52 mmol) and acetic acid (0.275 g, 4.60 mmol) at rt and stirred for 3 hours. The resulting reaction mixture was cooled to 0° C. and treated with sodium borohydride (0.262 g, 6.90 mmol) and then stirred for 5 h at rt. The mixture was diluted with ethyl acetate (10 mL) and washed with saturated aqueous NH$_4$Cl solution (10 mL). The combined organic layers were dried over sodium sulfate and concentrated. The obtained residue was purified by column chromatography (SiO$_2$, 2-3% MeOH/DCM) to afford 0.450 g (40% Yield) of N—((R)-1-(1H-indol-3-yl)propan-2-yl)tetrahydrofuran-3-amine as a colorless gummy liquid. MS (ESI) m/z 245.21 [M+H]$^+$.

Step 2

To a stirred solution of N—((R)-1-(1H-indol-3-yl)propan-2-yl)tetrahydrofuran-3-amine (0.450 g, 1.84 mmol) in toluene (3 mL) was added methyl (E)-3-(3,5-difluoro-4-formylphenyl)acrylate (0.501 g, 2.21 mmol) and acetic acid (0.221 g, 3.68 mmol). The resulting mixture was stirred at 90° C. for 5 h. The reaction mixture was diluted with EtOAc, washed with water, dried over sodium sulfate, filtered and concentrated. The residue was purified by chiral SFC to afford 150 mg (18% yield) of methyl (E)-3-(3,5-difluoro-4-((1R,3R)-3-methyl-2-((S)-tetrahydrofuran-3-yl)-2,3,4,9-tetrahydro-1H-pyrido[3,4-b]indol-1-yl)phenyl)acrylate and 180 mg (22% yield) of methyl (E)-3-(3,5-difluoro-4-((1R,3R)-3-methyl-2-((R)-tetrahydrofuran-3-yl)-2,3,4,9-tetrahydro-1H-pyrido[3,4-b]indol-1-yl)phenyl)acrylate as pale yellow solids. Methyl (E)-3-(3,5-difluoro-4-((1R,3R)-3-methyl-2-((S)-tetrahydrofuran-3-yl)-2,3,4,9-tetrahydro-1H-pyrido[3,4-b]indol-1-yl)phenyl)acrylate: MS (ESI): m/z 453.24 [M+H]$^+$. Methyl (E)-3-(3,5-difluoro-4-((1R,3R)-3-methyl-2-((R)-tetrahydrofuran-3-yl)-2,3,4,9-tetrahydro-1H-pyrido[3,4-b]indol-1-yl)phenyl)acrylate: MS (ESI) m/z 453.25 [M+H]$^+$.

Step 3-a

To a stirred solution of methyl (E)-3-(3,5-difluoro-4-((1R,3R)-3-methyl-2-((S)-tetrahydrofuran-3-yl)-2,3,4,9-tetrahydro-1H-pyrido[3,4-b]indol-1-yl)phenyl)acrylate (150 mg, 0.296 mmol) in methanol (1.5 mL) was added an aqueous solution of NaOH (0.132 mL, 0.995 mmol, 7.5M) at 0° C. and stirred at rt for 5 h. The reaction mixture was concentrated under reduced pressure. The residue was acidified with 1N HCl at 0° C., extracted with ethyl acetate (3×50 mL) and the combined organic layers were dried over Na$_2$SO$_4$, filtered and evaporated under reduced pressure to afford the crude product. The residue was purified by chiral SFC to afford 40 mg (27% Yield) of (E)-3-(3,5-difluoro-4-((1R,3R)-3-methyl-2-((S)-tetrahydrofuran-3-yl)-2,3,4,9-tetrahydro-1H-pyrido[3,4-b]indol-1-yl)phenyl)acrylic acid as an off white solid. $^1$H NMR (300 MHz, DMSO-d$_6$) δ 10.6 (br s, 1H), 7.65-7.34 (m, 4H), 7.19 (d, J=7.5 Hz, 1H), 7.04-6.88 (m, 2H), 6.64 (d, J=15.6 Hz, 1H), 5.29 (s, 1H), 3.79-3.40 (m, 6H), 2.83 (dd, J=15, 4.2 Hz, 1H), 2.57 (d, J=6.9 Hz, 1H), 1.69-1.62 (m, 1H), 1.58-1.46 (m, 1H), 1.16 (d, J=6.9 Hz, 3H); MS (ESI): m/z 439.26 [M+H]+; [α]$_D$=−73.2° (c 0.25, CHCl$_3$, 24° C.).

Step 3-b

To a stirred solution of methyl (E)-3-(3,5-difluoro-4-((1R,3R)-3-methyl-2-((R)-tetrahydrofuran-3-yl)-2,3,4,9-tetrahydro-1H-pyrido[3,4-b]indol-1-yl)phenyl)acrylate (0.180 g, 0.398 mmol) in methanol (2 mL) was added an aqueous solution of NaOH (0.159 mL, 1.19 mmol, 7.5M) at 0° C. and stirred at rt for 5 h. The reaction mixture was concentrated under reduced pressure. The obtained residue was acidified with 1N HCl at 0° C. and extracted with ethyl acetate (3×50 mL). The combined organic layers were dried over Na$_2$SO$_4$, filtered and evaporated under reduced pressure to afford the crude product. The residue was purified by chiral SFC to afford 80 mg (46% Yield) of (E)-3-(3,5-difluoro-4-((1R,3R)-3-methyl-2-((R)-tetrahydrofuran-3-yl)-2,3,4,9-tetrahydro-1H-pyrido[3,4-b]indol-1-yl)phenyl)acrylic acid as an off white solid. $^1$H NMR (300 MHz, DMSO-d$_6$) δ 12.7 (br s, 1H), 10.6 (s, 1H), 7.58-7.32 (m, 4H), 7.18 (d, J=8.1 Hz, 1H), 7.02-6.91 (m, 2H), 6.66 (d, J=15.6 Hz, 1H), 5.31 (s, 1H), 3.88-3.75 (m, 1H), 3.68-3.48 (m, 3H), 3.31-3.22 (m, 1H), 3.08 (t, J=8.1 Hz, 1H), 2.89 (dd, J=15 Hz, 3.6 Hz, 1H), 2.54-2.51 (m, 1H), 2.14-1.96 (m, 2H), 1.14 (d, J=6.3 Hz, 3H); MS (ESI): m/z 439.26 [M+H]+; [t]$_D$=−70.4° (c 0.25, CHCl$_3$, 24° C.).

The stereochemistry for compounds 8A and 8B was confirmed with small-molecule X-ray crystallography as indicated above and in Table 1.

Examples 9A and 9B (E)-3-(4-((1R,3R)-2-(3,3-Difluorocyclobutyl)-3-methyl-2,3,4,9-tetrahydro-1H-pyrido[3,4-b]indol-1-yl)-3,5-difluorophenyl)acrylic acid (9A)

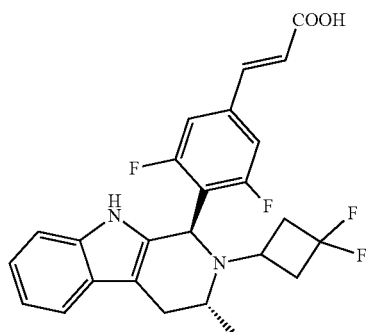

(E)-3-(4-((1S,3S)-2-(3,3-Difluorocyclobutyl)-3-methyl-2,3,4,9-tetrahydro-1H-pyrido[3,4-b]indol-1-yl)-3,5-difluorophenyl)acrylic acid (9B)

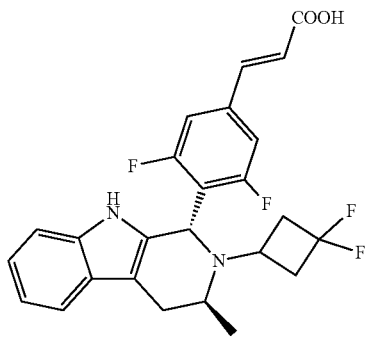 [SMILES: C[C@H]1Cc2c([nH]c3ccccc23)[C@H](c2c(F)cc(/C=C/C(=O)O)cc2F)N1C1CC(F)(F)C1]

Step 1

To a stirred solution of 1-(1H-indol-3-yl)propan-2-one (2 g, 11.6 mmol) in methanol (10 mL) was added 3,3-difluorocyclobutan-1-amine hydrochloride (1.81 g 12.7 mmol) and acetic acid (0.069 g, 1.15 mmol) at rt. The reaction was stirred for 3 hours, cooled to 0° C. and sodium cyanoborohydride (1.40 g, 23.1 mmol) was added. The mixture was stirred at rt for 24 h. The reaction was diluted with ethyl acetate (10 mL), washed with saturated aqueous NH$_4$Cl solution (10 mL) followed by brine. The combined organic layers were dried over sodium sulfate, filtered and concentrated under reduced pressure. The residue was purified by column chromatography (SiO$_2$, 2-3% MeOH/DCM) to afford 2.2 g (72% Yield) of N-(1-(1H-indol-3-yl)propan-2-yl)-3,3-difluorocyclobutan-1-amine as a colorless gummy liquid. MS (ESI) m/z 265.35 [M+H]$^+$.

Step 2

To a stirred solution of N-(1-(1H-indol-3-yl)propan-2-yl)-3,3-difluorocyclobutan-1-amine (2.2 g, 8.33 mmol) in toluene (25 mL) was added methyl (E)-3-(3,5-difluoro-4-formylphenyl)acrylate (2.07 g, 9.16 mmol) and acetic acid (0.1 ml, 1.66 mmol). The resulting mixture was stirred at 80° C. for 5 h. The reaction mixture was diluted with EtOAc and washed with water, dried over sodium sulfate, filtered and concentrated. The residue was purified by chiral SFC (Column/dimensions: Chiralpak AD-H (5 am, 250×21 mm); % CO$_2$: 65.0; % co-solvent (EtOH): 35.0; Total Flow: 60.0 g/min; Back Pressure: 100.0 bar; UV: 221 nm; Stack time: 5.0 min; Load/Inj: 2.5 mg; Solubility: MeOH; Total No of injections: 60; Instrument details: Make/Model: Thar SFC-80) to afford 500 mg (13% Yield) of methyl (E)-3-(4-((1R, 3R)-2-(3,3-difluorocyclobutyl)-3-methyl-2,3,4,9-tetrahydro-1H-pyrido[3,4-b]indol-1-yl)-3,5-difluorophenyl)acrylate (Designated as Peak 1) and 500 mg (13% Yield) of methyl (E)-3-(4-((1S,3S)-2-(3,3-difluorocyclobutyl)-3-methyl-2,3,4,9-tetrahydro-1H-pyrido[3,4-b]indol-1-yl)-3,5-difluorophenyl)acrylate (Designated as Peak 2). Methyl (E)-3-(4-((1R,3R)-2-(3,3-difluorocyclobutyl)-3-methyl-2,3,4,9-tetrahydro-1H-pyrido[3,4-b]indol-1-yl)-3,5-difluorophenyl)acrylate: MS (ESI) m/z 473.26 [M+H]$^+$. Methyl (E)-3-(4-((1S,3S)-2-(3,3-difluorocyclobutyl)-3-methyl-2,3,4,9-tetrahydro-1H-pyrido[3,4-b]indol-1-yl)-3,5-difluorophenyl)acrylate: MS (ESI) m/z 473.26 [M+H]$^+$.

Step 3-a

To a stirred solution of methyl (E)-3-(4-((1R,3R)-2-(3,3-difluorocyclobutyl)-3-methyl-2,3,4,9-tetrahydro-1H-pyrido[3,4-b]indol-1-yl)-3,5-difluorophenyl)acrylate (0.250 g, 0.520 mmol) in methanol (1.5 mL) was added an aqueous solution of NaOH (0.14 mL, 1.05 mmol, 7.5M) at 0° C. and the reaction was stirred at rt for 5 h. The reaction mixture was concentrated under reduced pressure. The resulting residue was acidified with 1N HCl at 0° C. and then extracted ethyl acetate (3×50 mL). The combined organic layers were dried over Na$_2$SO$_4$, filtered and evaporated under reduced pressure. The residue was purified by chiral SFC [Column/dimensions: Chiralcel OD-H (5 am, 250×30 mm); % CO$_2$: 65.0; % Co-solvent (MeOH): 35.0; Total Flow: 60.0 g/min; Back Pressure: 100.0 bar; UV: 223 nm; Stack time: 3.5 min; Load/Inj: 4.0 mg; Solubility: MeOH+DCM; Total Number of injections: 55; instrument details: Make/Model: Thar SFC-80] to afford 130 mg (53% yield) of (E)-3-(4-((1R,3R)-2-(3,3-difluorocyclobutyl)-3-methyl-2,3,4,9-tetrahydro-1H-pyrido[3,4-b]indol-1-yl)-3,5-difluorophenyl)acrylic acid as an off white solid. $^1$H NMR (300 MHz, DMSO-d$_6$) δ 10.6 (s 1H), 7.60-7.38 (m, 4H), 7.18 (d, J=7.5 Hz, 1H), 7.08-6.90 (m, 2H), 6.68 (d, J=15.9 Hz, 1H), 5.16 (s, 1H), 3.59-3.42 (m, 1H), 3.40-3.25 (m, 1H), 2.94 (dd, J=14.9, 4.0 Hz, 2H), 2.90-2.71 (m, 1H), 2.71-2.56 (m, 1H), 2.22-2.05 (m, 1H), 2.00-1.80 (m, 1H), 1.03 (d, J=6.6, 3H); MS (ESI) m/z 459.26 [M+H]+; [α]$_D$=−40.0° (c 0.25, MeOH, 24° C.).

Step 3-b

To a stirred solution of methyl (E)-3-(4-((1S,3S)-2-(3,3-difluorocyclobutyl)-3-methyl-2,3,4,9-tetrahydro-1H-pyrido[3,4-b]indol-1-yl)-3,5-difluorophenyl)acrylate (250 mg, 0.525 mmol) in methanol (1.5 mL) was added an aqueous solution of NaOH (0.14 mL, 1.05 mmol, 7.5M) at 0° C. and the reaction was stirred at rt for 5 h. The mixture was concentrated under reduced pressure to remove solvent. The residue was acidified with 1N HCl solution at 0° C. and then extracted with ethyl acetate (3×50 mL). The combined organic layer was dried over Na$_2$SO$_4$, filtered and evaporated under reduced pressure. The residue was purified by chiral SFC [Column/dimensions: Chiralcel OD-H (5 am, 250×30 mm); % CO$_2$: 60.0; % Co-solvent (MeOH): 40.0; Total Flow: 100.0 g/min; Back Pressure: 100.0 bar; UV: 220 nm; Stack time: 4.5 min; Load/Inj: 13.0 mg; Solubility: MeOH; Total No of injections: 28; Instrument details: Make/Model: Thar SFC-200-005] to afford 140 mg (57% Yield) of (E)-3-(4-((1S,3S)-2-(3,3-difluorocyclobutyl)-3-methyl-2,3,4,9-tetrahydro-1H-pyrido[3,4-b]indol-1-yl)-3,5-difluorophenyl)acrylic acid as an off white solid. $^1$H NMR (300 MHz, DMSO-d$_6$) δ 10.6 (s 1H), 7.60-7.38 (m, 4H), 7.18 (d, J=7.5 Hz, 1H), 7.08-6.90 (m, 2H), 6.68 (d, J=15.9 Hz, 1H), 5.16 (s, 1H), 3.59-3.42 (m, 1H), 3.40-3.25 (m, 1H), 2.94 (dd, J=14.9, 4.0 Hz, 2H), 2.90-2.71 (m, 1H), 2.71-2.56 (m, 1H), 2.22-2.05 (m, 1H), 2.00-1.80 (m, 1H), 1.03 (d, J=6.6, 3H); MS (ESI) m/z 459.26 [M+H]+; [α]$_D$=+32.0° (c 0.25, MeOH, 24° C.).

Compounds 9A and 9B are shown above and Table 1 with absolute stereochemistry arbitrarily assigned.

Example 10A (E)-3-(3,5-Difluoro-4-((1R,3R)-2-(4-methoxybenzyl)-3-methyl-2,3,4,9-tetrahydro-1H-pyrido[3,4-b]indol-1-yl)phenyl)acrylic acid (10A)

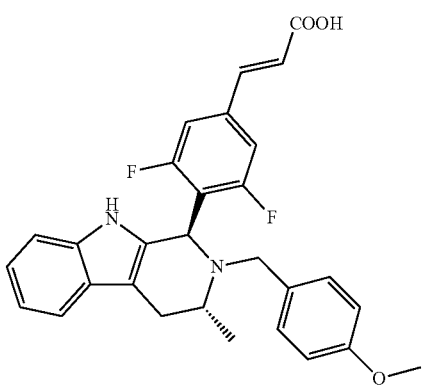 [SMILES: COc1ccc(CN2[C@H](c3c(F)cc(/C=C/C(=O)O)cc3F)c3[nH]c4ccccc4c3C[C@H]2C)cc1]

Step 1

To a stirred solution of (R)-1-(1H-indol-3-yl)propan-2-amine (1 g, 5.73 mmol) in 3 mL of ethanol was added 4-methoxybenzaldehyde (0.781 g, 5.73 mmol) and the mixture was stirred at 70° C. for 30 min. The resulting reaction mixture was cooled to 0° C., sodium borohydride (0.326 g, 8.59 mmol) was added and the reaction was stirred for 1 h at rt. The reaction was diluted with ethyl acetate (10 mL) and washed with saturated aqueous NH$_4$Cl solution (10 mL). The combined organic layers were dried over sodium sulfate, filtered and concentrated. The obtained residue was purified by column chromatography (SiO$_2$, 2-3% MeOH/DCM) to afford 1.00 g (59% Yield) of (R)-1-(1H-indol-3-yl)-N-(4-methoxybenzyl)propan-2-amine. MS (ESI) m/z 295.18 [M+H]$^+$.

Step 2

To a stirred solution of (R)-1-(1H-indol-3-yl)-N-(4-methoxybenzyl)propan-2-amine (300 mg, 1.09 mmol) in toluene (5 mL) was added methyl (E)-3-(3,5-difluoro-4-formylphenyl)acrylate (230 mg, 1.09 mmol) and acetic acid (0.122 g, 2.03 mmol). The resulting mixture was stirred at 90° C. for 5 h. The reaction mixture was diluted with EtOAc and washed with water. The combined organic layers were dried over sodium sulfate, filtered and concentrated. The residue was purified by reverse phase prep-HPLC to afford 230 mg (44% yield) of methyl (E)-3-(3,5-difluoro-4-((1R,3R)-2-(4-methoxybenzyl)-3-methyl-2,3,4,9-tetrahydro-1H-pyrido[3,4-b]indol-1-yl)phenyl)acrylate as a pale yellow solid. MS (ESI) m/z 503.21 [M+H]$^+$.

Step 3

To a stirred solution of methyl (E)-3-(3,5-difluoro-4-((1R,3R)-2-(4-methoxybenzyl)-3-methyl-2,3,4,9-tetrahydro-1H-pyrido[3,4-b]indol-1-yl)phenyl)acrylate (80 mg, 0.150 mmol) in methanol (1.5 mL) was added an aqueous solution of NaOH (0.212 mL, 1.59 mmol, 7.5M) at 0° C. and the mixture was stirred at rt for 5 h. The reaction mixture was concentrated under reduced pressure. The obtained residue was acidified with 1N HCl at 0° C., diluted with EtOAc and washed with water. The combined organic layers were dried over sodium sulfate, filtered and concentrated. The residue was purified by reverse phase prep-HPLC to afford 25 mg (33% Yield) of (E)-3-(3,5-difluoro-4-((1R,3R)-2-(4-methoxybenzyl)-3-methyl-2,3,4,9-tetrahydro-1H-pyrido[3,4-b]indol-1-yl)phenyl)acrylic acid as an off white solid. $^1$H NMR (300 MHz, DMSO-d$_6$) δ 12.8-12.4 (br s, 1H), 10.6 (s, 1H), 7.44-7.37 (m, 3H), 7.21-7.14 (m, 4H), 7.02-6.90 (m, 2H), 6.84-6.82 (m, 2H), 6.65-6.61 (m, 1H), 5.17 (s, 1H), 3.71 (s, 3H), 3.68 (d, J=13.6 Hz, 1H), 3.45 (d, J=13.6 Hz, 1H), 2.86-2.84 (m, 1H), 2.58-2.54 (m, 1H), 1.12 (m, 1H), 1.07-1.06 (d, J=6.4 Hz, 3H); MS (ESI) m/z 489.19 [M+H]$^+$.

Examples 11A and 11B (E)-3-(4-((1R,3R)-2-(Bicyclo[1.1.1]pentan-1-yl)-3-methyl-2,3,4,9-tetrahydro-1H-pyrido[3,4-b]indol-1-yl)-3,5-difluorophenyl)acrylic acid (11A)

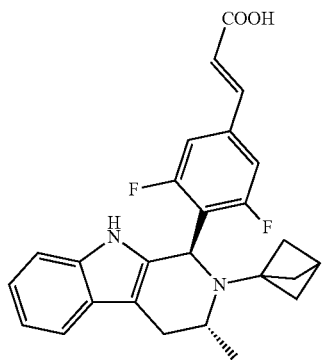 [SMILES: C[C@@H]1Cc2c([nH]c3ccccc23)[C@@H](c2c(F)cc(/C=C/C(=O)O)cc2F)N1C12CC(C1)C2]

(E)-3-(4-((1S,3S)-2-(Bicyclo[1.1.1]pentan-1-yl)-3-methyl-2,3,4,9-tetrahydro-1H-pyrido[3,4-b]indol-1-yl)-3,5-difluorophenyl)acrylic acid (11B)

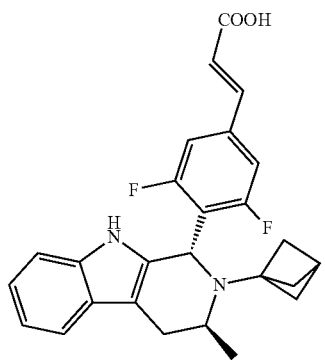 [SMILES: C[C@H]1Cc2c([nH]c3ccccc23)[C@H](c2c(F)cc(/C=C/C(=O)O)cc2F)N1C12CC(C1)C2]

Step 1

To a solution of 1-(1H-indol-3-yl)propan-2-one (0.062 g, 0.51 mmol) in MeOH (1 mL) was added glacial acetic acid to adjust the pH to 5-6. To this solution was added bicyclo[1.1.1]pentan-1-amine as the hydrochloride salt (0.075 g, 0.43 mmol) followed by sodium cyanoborohydride (0.054 g, 0.86 mmol). The reaction mixture was stirred at room temperature under a nitrogen atmosphere for 16 h. The solvent was removed under reduced pressure. Water (5 mL) was added and the mixture was extracted with ethyl acetate (2×5 mL). The combined organic layer was washed with saturated sodium bicarbonate solution, brine, dried over sodium sulfate, filtered and concentrated under reduced pressure. The crude residue was purified by flash column chromatography (SiO$_2$, 3-5% MeOH/DCM) to afford N-(1-(1H-indol-3-yl)propan-2-yl)bicyclo[1.1.1]pentan-1-amine (0.060 g, 58%) as a light yellow solid. MS (ESI) m/z: 241.26 [M+H]$^+$.

Step 2

To a solution of N-(1-(1H-indol-3-yl)propan-2-yl)bicyclo[1.1.1]pentan-1-amine (1.3 g, 5.41 mmol) in toluene (15 mL) were added methyl (E)-3-(3,5-difluoro-4-formylphenyl)acrylate (1.2 g, 4.87 mmol) and acetic acid (0.7 mL, 10.8 mmol). The resulting solution was stirred at 80° C. for 2 h. The reaction mixture was cooled to room temperature and poured into an aqueous solution of potassium carbonate (20 mL) and extracted with ethyl acetate (3×20 mL). The combined organic layers were dried over sodium sulfate, filtered and concentrated. The crude product was purified by column chromatography (SiO$_2$, 40% EtOAc/hexanes) to provide 1.0 g of a racemic mixture. The isomers were separated by chiral SFC [Chiral pak AD-H, (250×21 mm), 70 mL per min, liquid CO$_2$/IPA] to afford methyl (E)-3-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenyl)acrylate (0.381 g, 17% yield) (Designated as Peak 1, retention time: 6.41 min) and methyl (E)-3-(4-((1S,3S)-2-(bicyclo[1.1.1]pentan-1-yl)-3-methyl-2,3,4,9-tetrahydro-1H-pyrido[3,4-b]indol-1-yl)-3,5-difluorophenyl)acrylate (0.481 g, 21% yield) (Designated as Peak 2, retention time: 9.59 min), both as yellow solids. The absolute stereochemistry for peak 1 and peak 2 was arbitrarily assigned.

Methyl (E)-3-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenyl)acrylate: MS (ESI) m/z: 449.6 [M+H]$^+$.

Methyl (E)-3-(4-((1S,3S)-2-(bicyclo[1.1.1]pentan-1-yl)-3-methyl-2,3,4,9-tetrahydro-1H-pyrido[3,4-b]indol-1-yl)-3,5-difluorophenyl)acrylate: MS (ESI) m/z: 449.6 [M+H]$^+$.

Step 3-a

To a solution of methyl (E)-3-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenyl)acrylate (0.381 g, 0.850 mmol) in THF (4 mL) and MeOH (2 mL) was added an aqueous sodium hydroxide solution (1.2 mL, 9 mmol, 7.5M). The solution was stirred at room temperature for 4 h. Water (10 mL) was added to the reaction mixture and the pH of the aqueous solution was adjusted to 5 by addition of 2N HCl solution. The solution was extracted with diethyl ether (3×50 mL). The combined organic phase was dried over sodium sulfate, filtered and concentrated under reduced pressure. The crude product was purified by reverse phase HPLC [PURITAS PREP Cis (250×21.2 mm), 17 mL/min, (3 mM ammonium acetate+0.02% Formic acid) in water/acetonitrile, retention time 4.47 min] to afford (E)-3-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenyl)acrylic acid (0.110 g, 29% yield) as a pale yellow solid. $^1$H NMR (400 MHz, DMSO-d$_6$) δ 12.4 (s, 1H), 10.5 (s, 1H), 7.6 (d, J=16.0 Hz, 1H), 7.5 (d, J=10.0 Hz, 2H), 7.4 (d, J=8.0 Hz, 1H), 7.2 (d, J=7.6 Hz, 1H), 6.9 (m, 2H), 6.7 (d, J=16.0 Hz, 1H), 5.3 (s, 1H), 3.6 (m, 1H), 2.9 (m, 1H), 2.6 (m, 1H), 2.3 (s, 1H), 1.8 (d, J=8.4 Hz, 3H), 1.6 (d, J=1.2 Hz, 3H), 1.2 (m, 3H); MS (ESI) m/z 435.4 [M+H]$^+$.

Step 3-b

To a solution of methyl (E)-3-(4-((1S,3S)-2-(bicyclo[1.1.1]pentan-1-yl)-3-methyl-2,3,4,9-tetrahydro-1H-pyrido[3,4-b]indol-1-yl)-3,5-difluorophenyl)acrylate (0.481 g, 1.07 mmol) in THF (6 mL) and methanol (3 mL) was added an aqueous solution of sodium hydroxide solution (1.5 mL, 11.2 mmole, 7.5M). The solution was stirred at room temperature for 4 h. The pH of the aqueous solution was adjusted to 5 by addition of 2N HCl solution. The solution was extracted with diethyl ether (3×70 mL). The combined organic phase was dried over sodium sulfate, filtered and concentrated under reduced pressure. The residue was purified by reverse phase HPLC [PURITAS PREP Cis (250×21.2 mm), 17 mL/min, (3 mM ammonium acetate+0.02% formic acid) in water/acetonitrile, retention time: 5.29 min] to provide (E)-3-(4-((1S,3S)-2-(bicyclo[1.1.1]pentan-1-yl)-3-methyl-2,3,4,9-tetrahydro-1H-pyrido[3,4-b]indol-1-yl)-3,5-difluorophenyl)acrylic acid (0.153 g, 32% yield) as a pale yellow solid. $^1$H NMR (400 MHz, DMSO-d$_6$) δ 12.4 (br s, 1H), 10.5 (s, 1H), 7.6 (d, J=16.0 Hz, 1H), 7.5 (d, J=10.0 Hz, 2H), 7.4 (d, J=8.0 Hz, 1H), 7.2 (d, J=7.6 Hz, 1H), 6.9 (m, 2H), 6.7 (d, J=16.0 Hz, 1H), 5.3 (s, 1H), 3.6 (m, 1H), 2.9 (m, 1H), 2.6 (m, 1H), 2.3 (s, 1H), 1.8 (d, J=8.4 Hz, 3H), 1.6 (d, J=1.2 Hz, 3H), 1.2 (m, 3H); MS (ESI) m/z: 435.6 [M+H]$^+$.

The stereochemistry for compounds 11A and 11B shown above and in Table 1 was arbitrarily assigned and later confirmed by independent synthesis.

Figure 2:
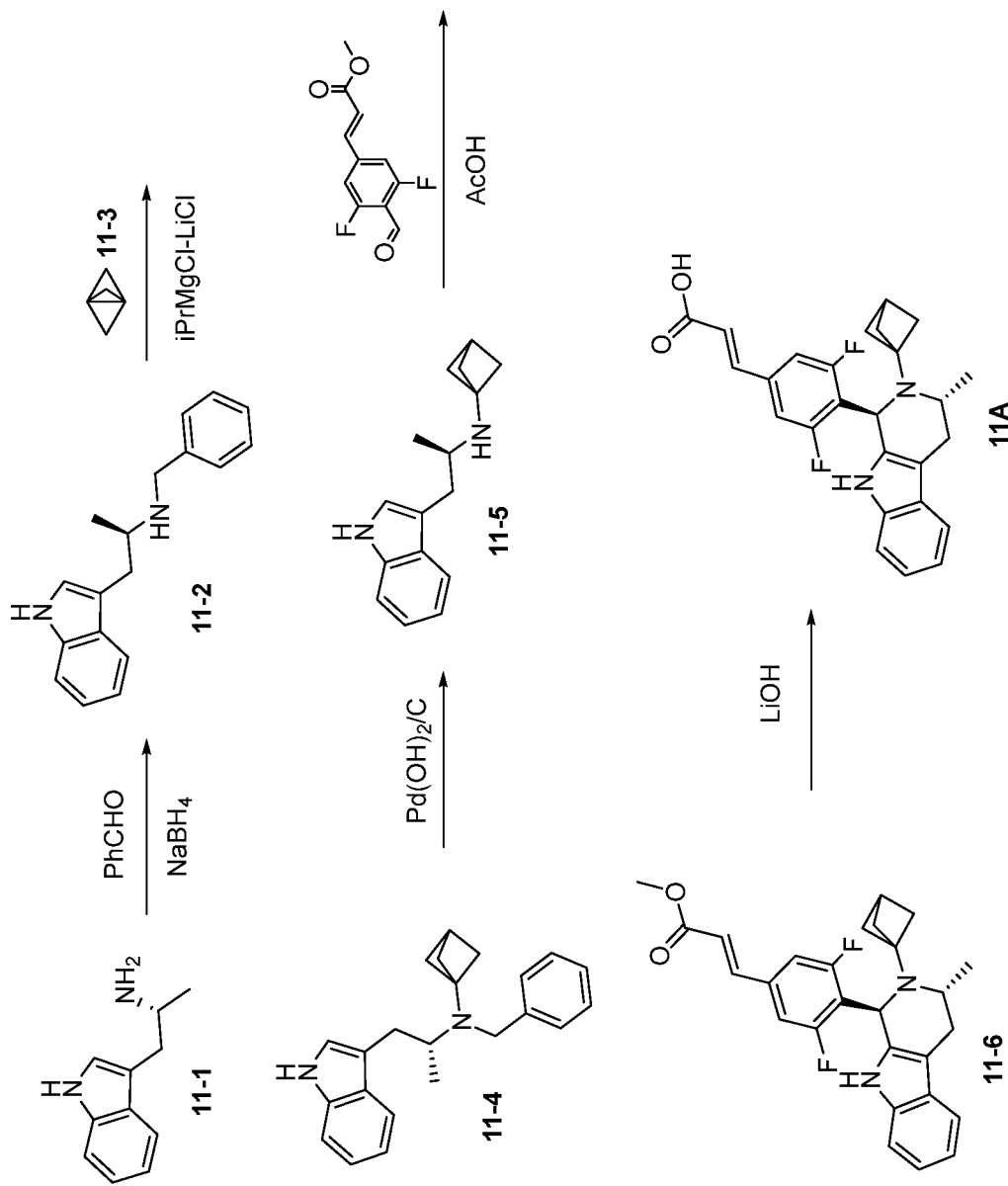
FIG. 2 illustrates a method of making Compound 11A.

Alternative Route to Synthesize Compound 11A
(FIG. 2)

Step 1

To a solution of benzaldehyde (PhCHO) (14.58 ml, 143 mmol) in EtOH (287 ml) was added (R)-1-(1H-indol-3-yl)propan-2-amine 11-1 (25.0 g, 143 mmol) and the reaction was heated to 50° C. for 3 h. The mixture was cooled to 0° C. and sodium borohydride (8.14 g, 214 mmol) was added in one portion and the reaction was stirred for 3 h at 0° C. The reaction was poured into a saturated, aqueous sodium bicarbonate solution (200 mL) and extracted with DCM (300 mL). The layers were separated and the aqueous layer was washed 3 times with DCM. The combined organic phase was dried with sodium sulfate, filtered and concentrated under vacuum. The residue was purified on silica gel using an MPLC system (340 g cartridge) eluting from 60-100% EA/hexane to afford (R)—N-benzyl-1-(1H-indol-3-yl)propan-2-amine 11-2 (36 g, 95%). $^1$H NMR (300 MHz, CDCl$_3$-d) δ 8.20-8.00 (s, 1H), 7.57 (d, J=7.9 Hz, 1H), 7.35 (d, J=8.0 Hz, 1H), 7.29-7.13 (m, 6H), 7.09 (t, J=7.4 Hz, 1H), 6.98 (s, 1H), 3.89 (d, J=13.1 Hz, 1H), 3.74 (d, J=13.1 Hz, 1H), 3.22-3.01 (m, 1H), 2.87 (t, J=7.5 Hz, 2H), 1.17 (d, J=6.2 Hz, 3H).

Step 2

1,1-Dibromo-2,2-bis(chloromethyl)cyclopropane (25 g, 84 mmol) was dissolved in anhydrous n-Bu$_2$O (30 mL) at room temperature. The resulting solution was cooled to −78° C. (dry ice/acetone cooling bath) and PhLi (100 ml, 168 mmol, 1.7M solution in n-Bu$_2$O) was added dropwise. The reaction mixture was stirred at −78° C. for 5 minutes and then warmed to 0° C. for 2 h. The white-yellow suspension of tricyclo[1.1.1.0$^{1,3}$]pentane 11-3 in n-Bu$_2$O was allowed to warm to room temperature and stirred for a few minutes.

Step 3

(R)—N-benzyl-1-(1H-indol-3-yl)propan-2-amine 11-2 (27.8 g, 105 mmol) was dissolved in anhydrous THF (90 mL) and treated with iPrMgCl—LiCl complex (162 mL, 211 mmol, 1.3M solution in THF) via syringe pump at room temperature. (Caution: vigorous gas evolution!) The resulting solution was vigorously stirred at room temperature for 30 min. The resulting mixture was added to the solution of tricyclo[1.1.1.0$^{1,3}$]pentane 11-3 in n-Bu$_2$O that was prepared in step 2 at room temperature. The septum was removed and the tube was sealed. The reaction mixture was vigorously stirred at 60° C. for 16 hours. The heterogeneous solution was poured into a saturated aqueous solution of NH$_4$Cl (200 mL) at 0° C. The sealed tube was washed carefully with ethyl acetate and water. The mixture was transferred to a separatory funnel and the layers were separated. The aqueous layers were washed with ethyl acetate (2×250 mL). All of the organic layers were combined, dried over sodium sulfate and concentrated under vacuum. The crude residue was purified by a MPLC (340 g column) using hexane/ethyl acetate (10-90%) and (R)—N-(1-(1H-indol-3-yl)propan-2-yl)-N-benzylbicyclo[1.1.1]pentan-1-amine 11-4 was obtained as a yellow oil (15.0 g, 45.4 mmol, 54% yield relative to the quantity of 1,1-dibromo-2,2-bis(chloromethyl)cyclopropane employed). $^1$H NMR (300 MHz, CDCl$_3$-d) δ 7.85-7.97 (br s, 1H), 7.53 (d, J=7.9 Hz, 1H), 7.36 (app t, J=7.5 Hz, 3H), 7.32-7.14 (m, 4H), 7.09 (t, J=7.5 Hz, 1H), 7.00 (d, J=2.0 Hz, 1H), 3.87 (d, J=15.1 Hz, 1H), 3.76 (d, J=15.1 Hz, 1H), 3.59-3.33 (m, 1H), 3.09 (dd, J=14.1, 4.8 Hz, 1H), 2.71 (dd, J=14.1, 9.6 Hz, 1H), 2.30 (s, 1H), 1.92-1.70 (m, 6H), 1.06 (d, J=6.6 Hz, 3H).

Step 4

Palladium hydroxide [10% on charcoal (wet), 5.0 g] was added to a solution of (R)—N-(1-(1H-indol-3-yl)propan-2-yl)-N-benzylbicyclo[1.1.1]pentan-1-amine 11-4 (15.5 g, 46.9 mmol) in EtOH (300 mL). The mixture was stirred under a hydrogen atmosphere (1 atm) at room temperature for 16 h. The solution was filtered through a pad of Celite® and the pad was washed with MeOH and CH$_2$Cl$_2$. The filtrate was concentrated under reduce pressure to obtain (R)—N-(1-(1H-indol-3-yl)propan-2-yl)bicyclo[1.1.1]pentan-1-amine 11-5 (11.0 g, 98% yield). $^1$H NMR (300 MHz, CDCl$_3$-d) δ 8.16-7.95 (br s, 1H), 7.62 (d, J=7.9 Hz, 1H), 7.36 (d, J=8.0 Hz, 1H), 7.19 (t, J=7.4 Hz, 1H), 7.12 (t, J=7.4 Hz, 1H), 7.02 (s, 1H), 3.25-3.11 (m, 1H), 2.88 (dd, J=14.2, 7.2 Hz, 1H), 2.74 (dd, J=14.2, 6.5 Hz, 1H), 2.36 (s, 1H), 1.95-1.51 (m, 6H), 1.12 (d, J=6.2 Hz, 3H); MS (ESI) m/z 240.9 [M+H]$^+$.

Step 5

To a stirred solution of (R)—N-(1-(1H-indol-3-yl)propan-2-yl)bicyclo[1.1.1]pentan-1-amine 11-5 (800 mg, 3.2 mmol) in toluene (8 mL) was added (E)-methyl-3-(3,5-difluoro-4-formylphenyl) acrylate (750 mg, 3.2 mmol) followed by AcOH (0.36 mL, 6.4 mmol) and the mixture was heated at 90° C. for 5 h. The reaction mixture was cooled to rt, diluted with water and extracted with ethyl acetate. The combined organic layer was dried over sodium sulfate, filtered and concentrated. The residue was purified by column chromatography (SiO$_2$, 20% ethyl acetate in hexanes) to afford methyl (E)-3-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenyl)acrylate (1.2 g, 2.7 mmol, 80% yield). Note: the product still contained about 4% cis isomer. A solution of methyl (E)-3-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenyl)acrylate (1.2 g, 2.7 mmol) in toluene (8 mL) was kept in a pre-heated oil bath (80° C.) and stirred for 10 min at same temperature. Hexane (8 mL) was added slowly to the solution and the mixture was stirred at 80° C. for 1 h. The reaction mixture was cooled to rt over a period of 1 h. The resulting solids were filtered and dried under reduced pressure to afford methyl (E)-3-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenyl)acrylate 11-6 (700 mg, 60% overall yield). $^1$H NMR (300 MHz, DMSO-d$_6$) δ 10.48 (br s, 1H), 7.63 (d, J=18.0 Hz, 1H), 7.50 (d, J=10.2 Hz, 2H), 7.38 (d, J=6.9 Hz, 1H), 7.17 (d, J=7.2 Hz, 1H), 7.01-6.91 (m, 2H), 6.80 (d, J=16.2 Hz, 1H), 5.33 (s, 1H), 3.73 (s, 3H), 3.61 (br s, 1H), 3.01-2.93 (m, 1H), 2.57 (d, J=16.2 Hz, 1H), 2.24 (s, 1H), 1.77 (d, J=9.0 Hz, 3H), 1.57 (d, J=9.0 Hz, 3H), 1.08 (d, J=6 Hz, 3H); MS (ESI) m/z 449.10 [M+H]$^+$.

Step 6

To a stirred solution of methyl (E)-3-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenyl)acrylate 11-6 (700 mg, 1.56 mmol) in a mixture of THF/H$_2$O (1:1, 10 mL) at 0° C. was added LiOH.H$_2$O (320 mg, 9.3 mmol). The resulting reaction mixture was stirred at rt for 6 h. The mixture was concentrated under reduced pressure to remove solvent and the residue was diluted with water and washed with diethyl ether. The aqueous layer was treated with aqueous HCl solution (1M) at 0° C. to adjust pH to ~5. The precipitate that formed was filtered, washed with water and dried under reduced pressure to afford (E)-3-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenyl) acrylic acid 11A (0.500 g, 1.15 mmol, 74% yield). $^1$H NMR (300 MHz, DMSO-d$_6$) δ 12.56 (br s, 1H), 10.58 (br s, 1H), 7.55 (d, J=15.9 Hz, 1H), 7.45 (d, J=10.2 Hz, 2H), 7.39 (d, J=7.5 Hz, 1H), 7.17 (d, J=7.2 Hz, 1H), 6.99 (dd, J=7.5, 6.0 Hz, 1H), 6.93 (dd, J=9.0, 6.3 Hz, 1H), 6.67 (d, J=15.9 Hz, 1H), 5.33 (s, 1H), 3.68-3.58 (m, 1H), 2.96 (dd, J=15.3, 4.2 Hz, 1H), 2.57 (dd, J=15.0, 1.5 Hz, 1H), 2.24 (s, 1H), 1.78 (d, J=9.3 Hz, 3H), 1.58 (d, J=9.6 Hz, 3H). 1.08 (d, J=6.6 Hz, 3H); MS (ESI) m/z 435.13 [M+H]+; [α]$^{25}_D$ −46.00 (c 0.5, MeOH); mp: 171-173° C.

Example 11C (E)-3-(4-((1S,3R)-2-(Bicyclo[1.1.1]pentan-1-yl)-3-methyl-2,3,4,9-tetrahydro-1H-pyrido[3,4-b]indol-1-yl)-3,5-difluorophenyl)acrylic acid (11C)

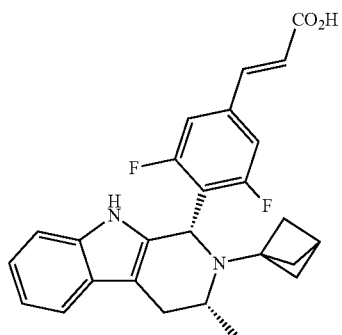

Step 1

To a stirred solution of (R)—N-(1-(1H-indol-3-yl)propan-2-yl)bicyclo[1.1.1]pentan-1-amine (7.3 g, 30.4 mmol) in toluene (150 mL) was added methyl (E)-3-(3,5-difluoro-4-formylphenyl)acrylate (6.87 g, 30.4 mmol) followed by AcOH (3.5 mL, 60.8 mmol) and the resulting reaction mixture was stirred at 90° C. for 4 h. The reaction mixture was cooled to room temperature, diluted with water and extracted with ethyl acetate. The combined organic layers were dried over Na$_2$SO$_4$, filtered and concentrated. The residue was purified by column chromatography (SiO$_2$, 20% ethyl acetate/hexanes) to afford a solid which was triturated with n-pentane (100 mL). The resulting solids were filtered. The mother liquor (containing the pentane washings) was concentrated and purified by reversed phase HPLC [Mobile phase: (A) 10 mM aqueous ammonium bicarbonate, (B) Acetonitrile; Flow: 19 mL/min; Column: X Select C18 (150×19 mm) 5 μm; Gradient-(Time (min)/% B): 0.1/75, 10/80, 12/80, 12.1/98, 14/98, 14.1/75, 17/75, Solubility: ACN+H$_2$O+THF] to afford methyl (E)-3-(4-((1S,3R)-2-(bicyclo[1.1.1]pentan-1-yl)-3-methyl-2,3,4,9-tetrahydro-1H-pyrido[3,4-b]indol-1-yl)-3,5-difluorophenyl)acrylate (100 mg, 0.22 mmol, 0.73% yield) as an off-white solid. MS (ESI) r/z 449.34 [M+H]$^+$.

Step 2

To a stirred solution of methyl (E)-3-(4-((1S,3R)-2-(bicyclo[1.1.1]pentan-1-yl)-3-methyl-2,3,4,9-tetrahydro-1H-pyrido[3,4-b]indol-1-yl)-3,5-difluorophenyl)acrylate (100 mg, 0.22 mmol) in a mixture of THF and water (1:1, total of 2 mL) at 0° C. was added LiOH.H$_2$O (46 mg, 1.33 mmol). The resulting reaction mixture was stirred at rt for 4 h and then concentrated. Water (10 mL) was added to the residue and the mixture was cooled to 0° C. and treated with 0.1 M HCl to adjust pH to ~6. The reaction mixture was extracted with Et$_2$O (2×20 mL). The organic layer was washed with water (2×20 mL), dried over Na$_2$SO$_4$, filtered and concentrated to afford (E)-3-(4-((1S,3R)-2-(bicyclo[1.1.1]pentan-1-yl)-3-methyl-2,3,4,9-tetrahydro-1H-pyrido[3,4-b]indol-1-yl)-3,5-difluorophenyl)acrylic acid (30 mg, 0.06 mmol, 31% yield) as a pale yellow solid. $^1$H NMR (400 MHz, DMSO) δ 12.57 (br s, 1H), 10.75 (s, 1H), 7.49 (d, J=16.0 Hz, 1H), 7.40 (d, J=9.6 Hz, 3H), 7.24 (d, J=8.0 Hz, 1H), 7.02 (t, J=6.8 Hz, 1H), 6.95 (t, J=6.8 Hz, 1H), 6.63 (d, J=16.0 Hz, 1H), 5.40 (s, 1H), 3.52-3.48 (m, 1H), 2.92 (dd, J=15.6, 5.6 Hz, 1H), 2.53 (s, 1H), 2.32 (s, 1H), 1.80 (s, 6H), 1.02 (d, J=7.2 Hz, 3H); MS (ESI) m/z 435.25.

Example 11D (E)-3-(4-((1R,3R)-2-(Bicyclo[1.1.1]pentan-1-yl)-3-methyl-2,3,4,9-tetrahydro-1H-pyrido[3,4-b]indol-1-yl-1-d)-3,5-difluorophenyl)acrylic acid (11D)

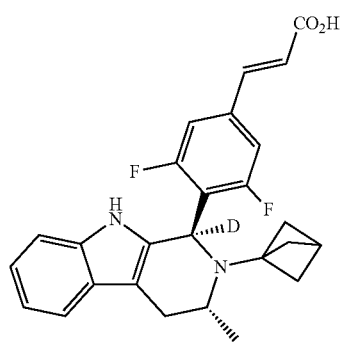 [SMILES: [2H][C@@]1(c2c(F)cc(/C=C/C(=O)O)cc2F)c2[nH]c3ccccc3c2C[C@@H](C)N1C12CC(C1)C2]

Step 1

To a stirred solution of (R)—N-(1-(1H-indol-3-yl)propan-2-yl)bicyclo[1.1.1]pentan-1-amine (0.100 g, 0.416 mmol) in toluene (1.0 mL) was added methyl (E)-3-(3,5-difluoro-4-(formyl-d)phenyl)acrylate (0.095 g, 0.416 mmol) and acetic acid (0.050 g, 0.832 mmol) and the mixture was heated at 90° C. for 5 h. The reaction mixture was cooled to rt, diluted with EtOAc (10 mL) and washed with aqueous saturated solution of sodium bicarbonate. The combined organic layers were dried over Na$_2$SO$_4$, filtered and concentrated. The residue was purified by flash chromatography (SiO$_2$, 20% ethyl acetate/hexane) to afford methyl (E)-3-(4-((1R,3R)-2-(bicyclo[1.1.1]pentan-1-yl)-3-methyl-2,3,4,9-tetrahydro-1H-pyrido[3,4-b]indol-1-yl-1-d)-3,5-difluorophenyl)acrylate (0.122 mg, 0.271 mmol, 65% yield) as a white solid. The resultant material was dissolved in toluene (1 mL) which was pre-heated to 90° C. Hexane, pre-heated to 70° C., was slowly added. The mixture was cooled to rt and then stored at 4° C. for 12 h. The resulting solid was filtered to afford methyl (E)-3-(4-((1R,3R)-2-(bicyclo[1.1.1]pentan-1-yl)-3-methyl-2,3,4,9-tetrahydro-1H-pyrido[3,4-b]indol-1-yl-1-d)-3,5-difluorophenyl)acrylate (0.029 mg, 0.065 mmol, 16% yield); MS (APCI) m/z 450.20 [M+H]$^+$.

Step 2

To a stirred solution of methyl (E)-3-(4-((1R,3R)-2-(bicyclo[1.1.1]pentan-1-yl)-3-methyl-2,3,4,9-tetrahydro-1H-pyrido[3,4-b]indol-1-yl-1-d)-3,5-difluorophenyl)acrylate (0.029 mg, 0.065 mmol) in THF/water (1:1, total of 0.8 mL) at 0° C. was added LiOH (0.017 g, 0.400 mmol) and the reaction was stirred at rt for 5 h. The organic volatiles were removed under reduced pressure at 20° C. The residue was treated with an aqueous solution of hydrogen chloride (1N) at 0° C. to adjust pH to 6. The aqueous layer was extracted with diethyl ether (2×10 mL) and the combined organic layer was washed with water, dried over sodium sulfate, filtered and concentrated. The residue was triturated with diethyl ether: pentane (1:10, 3 mL total) which were removed under reduced pressure to afford (E)-3-(4-((1R,3R)-2-(bicyclo[1.1.1]pentan-1-yl)-3-methyl-2,3,4,9-tetrahydro-1H-pyrido[3,4-b]indol-1-yl-1-d)-3,5-difluorophenyl)acrylic acid as a white solid (0.024 mg, 0.055 mmol, 83% yield). $^1$H NMR (400 MHz, DMSO-$d_6$) δ 12.6 (br s, 1H), 10.6 (br s, 1H), 7.54 (d, J=15.8 Hz, 1H), 7.45 (d, J=10.2 Hz, 2H), 7.39 (d, J=7.9 Hz, 1H), 7.18 (d, J=7.9 Hz, 1H), 7.02-6.97 (m, 1H), 6.97-6.92 (m, 1H), 6.67 (d, J=16.1 Hz, 1H), 3.68-3.58 (m, 1H), 2.96 (dd, J=14.9, 5.0 Hz, 1H), 2.62-2.54 (m, 1H), 2.25 (s, 1H), 1.77 (d, J=9.0 Hz, 3H), 1.59 (d, J=9.2 Hz, 3H), 1.08 (d, J=6.5 Hz, 3H); MS (APCI) m/z 436.2 [M+H]$^+$.

Example 12A

Ethyl (E)-3-(4-((1R,3R)-2-(Bicyclo[1.1.1]pentan-1-yl)-3-methyl-2,3,4,9-tetrahydro-1H-pyrido[3,4-b]indol-1-yl)-3,5-difluorophenyl)acrylate (12A)

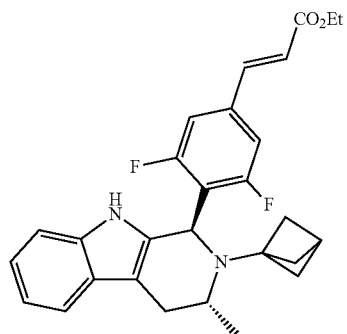 [SMILES: CCOC(=O)/C=C/c1cc(F)c([C@@H]2c3[nH]c4ccccc4c3C[C@@H](C)N2C23CC(C2)C3)c(F)c1]

Step 1

4-Bromo-2,6-difluorobenzaldehyde (7.0 g, 31.7 mmol) and ethyl acrylate (4.7 g, 47.5 mmol) were combined in a sealed tube and the solution was degassed thoroughly with argon for 10 min. N,N-dimethylacetmide (70 mL), tri-o-tolylphosphine (0.92 g, 1.36 mmol), palladium(II) acetate (0.34 g, 0.678 mmol) and triethylamine (9 mL, 27.1 mmol) were added and the mixture was degassed again for 15 min. The resulting reaction mixture was stirred at 80° C. for 6 h. The reaction mixture was cooled to room temperature, filtered through a Celite pad which was washed thoroughly with methanol (20 mL). The obtained filtrate was concentrated under reduced pressure. The crude compound was purified by flash chromatography (SiO$_2$, 1:9 ethyl acetate/hexane) to afford ethyl (E)-3-(3,5-difluoro-4-formylphenyl)acrylate (4.5 g, 18.7 mmol, 59% yield) as a pale yellow solid.

Step 2

To a stirred solution of (R)—N-(1-(1H-indol-3-yl)propan-2-yl)bicyclo[1.1.1]pentan-1-amine (500 mg, 2.34 mmol) in toluene (5.8 mL) was added ethyl (E)-3-(3,5-difluoro-4-formylphenyl)acrylate (500 mg, 2.57 mmol) and acetic acid (280 mg, 4.67 mmol) and the mixture was heated at 90° C. for 5 h. The reaction mixture was diluted with EtOAc and washed with water. The combined organic layers were dried over Na$_2$SO$_4$, filtered and concentrated. The residue was purified by flash chromatography (SiO$_2$, 20% ethyl acetate/hexanes) to afford ethyl (E)-3-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenyl)acrylate (700 mg, 1.51 mmol, 65% yield) as a pale yellow solid. $^1$H NMR (400 MHz, DMSO-$d_6$) δ 10.50 (s, 1H), 7.60 (d, J=16.0 Hz, 1H), 7.48 (d, J=10.0 Hz, 2H), 7.38 (d, J=7.2 Hz, 1H), 7.17 (d, J=8.0 Hz, 1H), 7.00-6.92 (m, 2H), 6.77 (d, J=16.4 Hz, 1H), 5.33 (s, 1H), 4.19 (q, J=7.6 Hz, 2H), 3.63-3.61 (m, 1H), 2.95 (dd, J=14.8 Hz, 4.0 Hz, 1H), 2.57 (dd, J=14.8 Hz, 2.0 Hz, 1H), 2.24 (s, 1H), 1.77 (d, J=8.4 Hz, 3H), 1.58 (d, J=8.0 Hz, 3H), 1.25 (t, J=7.2 Hz, 3H), 1.08 (d, J=6.4 Hz, 3H); $^{19}$F NMR (400 MHz, DMSO-$d_6$) δ –112.01; MS (ESI) m/z 463.36 [M+H]$^+$.

Examples 13A and 13B (E)-3-(3,5-Difluoro-4-((1S,3S)-2-(2-fluoro-2-methylpropyl)-6-hydroxy-3-methyl-2,3,4,9-tetrahydro-1H-pyrido[3,4-b]indol-1-yl)phenyl)acrylic acid (13A)

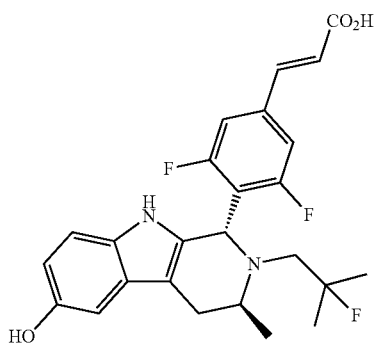 [SMILES: C[C@H]1Cc2c([nH]c3ccc(O)cc23)[C@H](c2c(F)cc(/C=C/C(=O)O)cc2F)N1CC(C)(C)F]

(E)-3-(3,5-Difluoro-4-((1R,3R)-2-(2-fluoro-2-methylpropyl)-6-hydroxy-3-methyl-2,3,4,9-tetrahydro-1H-pyrido[3,4-b]indol-1-yl)phenyl)acrylic acid (13B)

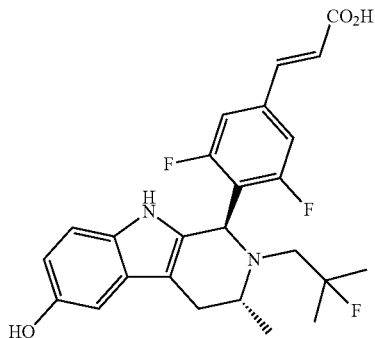 [SMILES: C[C@@H]1Cc2c([nH]c3ccc(O)cc23)[C@@H](c2c(F)cc(/C=C/C(=O)O)cc2F)N1CC(C)(C)F]

Step 1

Ammonium acetate (1.18 g, 15.3 mmol) was added in one portion to the mixture of 5-(benzyloxy)-1H-indole-3-carbaldehyde (3.5 g, 13.93 mmol) and nitroethane (14.9 ml, 209 mmol) and heated at reflux for 8 hours. The reaction mixture was cooled to room temperature and excess nitroethane was removed in vacuo. Saturated aqueous NaHCO$_3$ solution (15 mL) was added and the resulting mixture was extracted with ethyl acetate (3×20 mL). The organic layers were combined, dried over anhydrous Na$_2$SO$_4$, filtered and concentrated in vacuo. The crude product was purified by column chromatography (SiO$_2$, 0-50% EtOAc in hexane) to afford (Z)-5-(benzyloxy)-3-(2-nitroprop-1-en-1-yl)-1H-indole (1.7 g, 40% yield) as a yellow solid. MS (APCI) m/z 309.12 [M+H]$^+$.

Step 2

To a stirred solution of (Z)-5-(benzyloxy)-3-(2-nitroprop-1-en-1-yl)-1H-indole (1 g, 3.24 mmol) was added LAH (4.86 mL, 9.73 mmol, 2M in THF) dropwise at 0° C. and heated at reflux for 18 hours. The reaction mixture was cooled to rt and quenched with cold water slowly (0.4 mL), 15% aqueous NaOH solution (0.80 mL) and water (1.2 mL). The resulting solid was extracted with EtOAc (3×10 mL). The combined organic layer was dried over sodium sulfate, filtered, and concentrated. The resulting residue was purified by column chromatography (SiO$_2$, 0-20% methanol in dichloromethane) to afford 1-(5-(benzyloxy)-1H-indol-3-yl)propan-2-amine (0.46 g, 51% yield). MS (APCI) m/z 281.16 [M+H]$^+$.

Step 3

To a stirred solution of 1-(5-(benzyloxy)-1H-indol-3-yl)propan-2-amine (0.30 g, 1.070 mmol) in 1,4-dioxane (3.6 mL) was added 2-fluoro-2-methylpropyl trifluoromethanesulfonate (0.300 g, 1.34 mmol) and N,N-diisopropylethylamine (0.373 ml, 2.14 mmol) and the reaction was heated at 90° C. for 3 h. The reaction mixture was cooled to room temperature and diluted with water (20 mL). The mixture was extracted with EtOAc (2×15 mL). The combined organic layer was dried over sodium sulfate, filtered and concentrated. The residue was purified by column chromatography (60-80% EtOAc in hexane) to afford N-(1-(5-(benzyloxy)-1H-indol-3-yl)propan-2-yl)-2-fluoro-2-methylpropan-1-amine (0.22 g, 58% yield) MS (APCI) m/z 355.21 [M+H]$^+$.

Step 4

To a stirred solution of N-(1-(5-(benzyloxy)-1H-indol-3-yl)propan-2-yl)-2-fluoro-2-methylpropan-1-amine (0.27 g, 0.762 mmol) in MeOH (3.81 ml) was added palladium hydroxide (20 wt/wt %) (0.047 g, 0.076 mmol) The reaction was stirred under 1 atm of hydrogen gas for 4 h. The reaction mixture was filtered through a Celite pad and the filtrate was concentrated under reduced pressure to afford 3-(2-((2-fluoro-2-methylpropyl)amino)propyl)-1H-indol-5-ol (0.16 g, 79% yield) MS (APCI) m/z 265.16 [M+H]$^+$.

Step 5

To a stirred solution of 3-(2-((2-fluoro-2-methylpropyl)amino)propyl)-1H-indol-5-ol (0.15 g, 0.567 mmol) in toluene (2.8 mL) were added ethyl (E)-3-(3,5-difluoro-4-formylphenyl)acrylate (0.150 g, 0.624 mmol) and acetic acid (0.07 g, 1.14 mmol) and the mixture was heated at 80° C. for 4 h. The reaction mixture was diluted with EtOAc and washed with water. The organic layer was separated and the aqueous layer was extracted with ethyl acetate (2×15 mL). The combined organic layer was dried over sodium sulfate, filtered and concentrated. The residue was purified by column chromatography (SiO$_2$, 15-60% EtOAc in hexane) to afford ethyl (E)-3-(3,5-difluoro-4-((1R,3R)-2-(2-fluoro-2-methylpropyl)-6-hydroxy-3-methyl-2,3,4,9-tetrahydro-1H-pyrido[3,4-b]indol-1-yl)phenyl)acrylate (0.16 g, 0.329 mmol, 58% yield, pale yellow solid) as a mixture of enantiomers MS (APCI) m/z 487.21 [M+H]$^+$.

Step 6

To a stirred solution of racemic ethyl (E)-3-(3,5-difluoro-4-((1R,3R)-2-(2-fluoro-2-methylpropyl)-6-hydroxy-3-methyl-2,3,4,9-tetrahydro-1H-pyrido[3,4-b]indol-1-yl)phenyl)acrylate (0.16 g, 0.329 mmol) in a mixture of MeOH:THF:water (1:1:1, total of 3 mL) at 0° C. was added sodium hydroxide (0.04 g, 0.987 mmol). The reaction was stirred at rt for 2 h. After the reaction was completed, the mixture was concentrated under reduced pressure. The residue was acidified with an aqueous solution of citric acid (1M) at 0° C. Ethyl acetate was added to dissolve the precipitate. The organic layer was separated, dried over sodium sulfate, filtered and concentrated to obtain a mixture of enantiomers: (E)-3-(3,5-difluoro-4-((1R,3R)-2-(2-fluoro-2-methylpropyl)-6-hydroxy-3-methyl-2,3,4,9-tetrahydro-1H-pyrido[3,4-b]indol-1-yl)phenyl)acrylic acid (0.11 g, 73.0% yield) as a pale yellow solid. MS (APCI) m/z 459.18 [M+H]$^+$.

Step 7

120 mg of racemic (E)-3-(3,5-difluoro-4-((1R,3R)-2-(2-fluoro-2-methylpropyl)-6-hydroxy-3-methyl-2,3,4,9-tetrahydro-1H-pyrido[3,4-b]indol-1-yl)phenyl)acrylic acid was purified by SFC (Preparative SFC Conditions: Column/dimensions Chiralcel OD-H (250×30 mm), 5 µm; % CO$_2$: 5.0; % Co-solvent (MeOH): 35.0; Total Flow: 100.0 g/min; Back Pressure: 100.0 bar; UV: 210 nm; Stack time: 5.5 min; Load/Inj: 6.5 mg) to afford (E)-3-(3,5-Difluoro-4-((1R,3R)-2-(2-fluoro-2-methylpropyl)-6-hydroxy-3-methyl-2,3,4,9-tetrahydro-1H-pyrido[3,4-b]indol-1-yl)phenyl)acrylic acid (Designated as Peak 1) (22 mg, 0.04 mmol, 18% yield). $^1$H NMR (300 MHz, DMSO-d$_6$) δ 10.2 (s, 1H), 8.53 (br s, 1H), 7.45 (d, J=16.8 Hz, 1H), 7.40 (d, J=10.5 Hz, 2H), 6.96 (d, J=8.4 Hz, 1H), 6.71 (d, J=2.1, 1H), 6.64 (d, J=16.2 Hz, 1H), 6.51 (dd, J=9.0 Hz, 2.7 Hz, 1H), 5.16 (s, 1H), 3.53-3.45 (m, 1H), 2.91-2.73 (m, 2H), 2.44-2.26 (m, 2H), 1.19 (d, J=21.3 Hz, 3H), 1.12 (d, J=21.6 Hz, 3H), 1.04 (d, J=6.6 Hz, 3H), carboxylic acid proton not observed; MS (ESI) m/z 459.32 [M+H]$^+$. (E)-3-(3,5-Difluoro-4-((1S,3S)-2-(2-fluoro-2-methylpropyl)-6-hydroxy-3-methyl-2,3,4,9-tetrahydro-1H-pyrido[3,4-b]indol-1-yl)phenyl)acrylic acid (Designated as Peak 2) (20 mg 0.04 mmol, 18% yield) as an off white solid. $^1$H NMR (300 MHz, DMSO-d$_6$) δ 10.2 (s, 1H), 8.53 (br s, 1H), 7.34 (d, J=16.2 Hz, 1H), 7.32 (d, J=10.6 Hz, 2H), 6.96 (d, J=8.4 Hz, 1H), 6.71 (d, J=2.1, 1H), 6.59 (d, J=16.2 Hz, 1H), 6.50 (dd, J=8.7, 2.1 Hz, 1H), 5.15 (s, 1H), 3.51-3.42 (m, 1H), 2.91-2.73 (m, 2H), 2.44-2.27 (m, 2H), 1.19 (d, J=21.3 Hz, 3H), 1.12 (d, J=21.0 Hz, 3H), 1.04 (d, J=6.6 Hz, 3H), carboxylic acid proton not observed; MS (ESI) m/z 459.29 [M+H]$^+$.

Compounds 13A and 13B are shown above and in Table 1 with absolute stereochemistry arbitrarily assigned.

Example 14A (E)-3-(3,5-Difluoro-4-((1R,3R)-2-((3-fluorobicyclo[1.1.1]pentan-1-yl)methyl)-3-methyl-2,3,4,9-tetrahydro-1H-pyrido[3,4-b]indol-1-yl)phenyl)acrylic acid (14A)

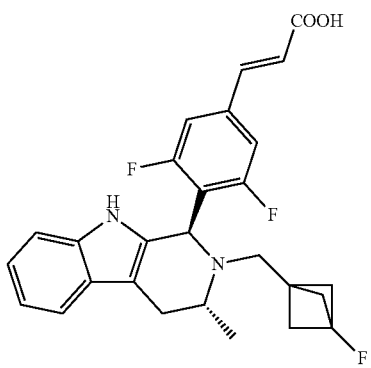 [SMILES: C[C@@H]1Cc2c([nH]c3ccccc23)[C@@H](c2c(F)cc(/C=C/C(=O)O)cc2F)N1CC12CC(F)(C1)C2]

Step 1

To a stirred suspension of 3-fluorobicyclo[1.1.1]pentane-1-carboxylic acid (560 mg, 4.3 mmol), in anhydrous THF (5 mL) was added a solution of propylphosphonic anhydride (5.5 mL, 8.6 mmol, 50 wt % in EtOAc) and N,N-diisopropylethylamine (1.8 mL, 8.6 mmol) at 0° C., and the mixture was stirred for 20 min at the same temperature. (R)-1-(1H-indol-3-yl)propan-2-amine (500 mg, 2.8 mmol) was added into the reaction mixture at 0° C. and the mixture was stirred at rt for 18 h. After completion of the reaction as indicated by TLC, the reaction mixture was diluted with ice cold water and extracted with ethyl acetate (2×50 mL). The combined organic layers were dried over sodium sulfate, filtered and concentrated. The resultant residue was purified by flash chromatography (SiO$_2$, 25% ethyl acetate/hexanes) to afford (R)—N-(1-(1H-indol-3-yl)propan-2-yl)-3-fluorobicyclo[1.1.1]pentane-1-carboxamide (500 mg, 1.75 mmol, 60% yield) as a pale brown liquid. MS (ESI) m/z 287.25 [M+H]$^+$.

Step 2

To a stirred suspension of (R)—N-(1-(1H-indol-3-yl)propan-2-yl)-3-fluorobicyclo[1.1.1]pentane-1-carboxamide (500 mg, 1.7 mmol), in dry THF (5 mL) was added a solution of borane THF complex (3.5 mL, 3.5 mmol, 1.0M in THF) at 0° C. and the mixture was stirred at rt for 16 h. The completion of the reaction (as monitored by TLC) was determined by consumption of starting material. The reaction mixture was cooled to rt followed by addition of methanol (10 mL) and then the mixture was stirred at room temperature for 1 h. The reaction mixture was diluted with water and extracted with ethyl acetate (2×50 mL). The combined organic layer was dried over sodium sulfate, filtered and concentrated. The resultant residue was purified by flash chromatography (SiO$_2$, 80% ethyl acetate/hexanes) to afford (R)—N-((3-fluorobicyclo[1.1.1]pentan-1-yl)methyl)-1-(1H-indol-3-yl)propan-2-amine (450 mg, 1.65 mmol, 94% yield) as an off white solid. MS (ESI) m/z 273.53 [M+H]$^+$.

Step 3

To a stirred solution of (R)—N-((3-fluorobicyclo[1.1.1]pentan-1-yl)methyl)-1-(1H-indol-3-yl)propan-2-amine (350 mg, 1.2 mmol) in toluene (3 mL) was added methyl (E)-3-(3,5-difluoro-4-formylphenyl)acrylate (290 mg, 1.2 mmol), followed by acetic acid (154 mg, 2.5 mmol) at room temperature. The resulting mixture was stirred at 90° C. for 6 h and cooled to room temperature. The reaction mixture was diluted with water and extracted with ethyl acetate (2×50 mL). The combined organic layers were dried over Na$_2$SO$_4$, filtered and concentrated under reduced pressure to afford crude compound (E)-methyl 3-(3,5-difluoro-4-((1R,3R)-2-((3-fluorobicyclo[1.1.1]pentan-1-yl)methyl)-3-methyl-2,3,4,9-tetrahydro-1H-pyrido[3,4-b]indol-1-yl)phenyl)acrylate (480 mg, 0.99 mmol, 77% yield) as a brown liquid which was used in the next step without purification. MS (ESI) m/z 481.86 [M+H]$^+$.

Step 4

To a stirred solution of (E)-methyl 3-(3,5-difluoro-4-((1R,3R)-2-((3-fluorobicyclo[1.1.1]pentan-1-yl)methyl)-3-methyl-2,3,4,9-tetrahydro-1H-pyrido[3,4-b]indol-1-yl)phenyl)acrylate (600 mg, 1.25 mmol) in a mixture of THF/methanol/water (1:1:1, total of 6 mL) at 0° C. was added NaOH (100 mg, 2.49 mmol). The mixture was stirred at rt for 5 h. The volatiles were removed under reduced pressure. The resulting residue was acidified with aqueous hydrogen chloride solution (1M) at 0° C. to adjust pH to 5, and the aqueous phase was extracted with EtOAc (3×50 mL). The combined organic layer was dried over Na$_2$SO$_4$, filtered and concentrated. The crude product was further purified by SFC [Column/dimensions: Chiralcel OD-H (250×30 mm), 5 am silica; % CO$_2$: 70.0%; % Co-solvent (MeOH): 30.0%; Total Flow: 100.0 g/min; Back Pressure: 100.0 bar; UV: 212 nm; Stack time: 5.80 min; Load/Inj 5.2 mg; Solubility: Methanol; Total No of injections: 130; Instrument details (Make/Model): Thar SFC-200-005]; to afford (E)-3-(3,5-difluoro-4-((1R,3R)-2-((3-fluorobicyclo[1.1.1]pentan-1-yl)methyl)-3-methyl-2,3,4,9-tetrahydro-1H-pyrido[3,4-b]indol-1-yl)phenyl)acrylic acid (220 mg, 0.47 mmol, 37% yield) as an off white solid. Traces of an unknown aliphatic impurity that were observed by $^1$H NMR. Further purification by reverse phase HPLC [Mobile phase: (A) 10 mM aqueous ammonium bicarbonate, (B) acetonitrile; Flow: 19 mL/min; column: XBRIDGE C18 (150×19 mm) 5 am Gradient-(Time (min)/% B): 0.1/30, 10/60, 11/60, 11.1/99, 13/99, 13.1/10, 15/10] to give pure (E)-3-(3,5-difluoro-4-((1R,3R)-2-((3-fluorobicyclo[1.1.1]pentan-1-yl)methyl)-3-methyl-2,3,4,9-tetrahydro-1H-pyrido[3,4-b]indol-1-yl)phenyl)acrylic acid (50 mg, 0.17 mmol, 8.6% yield). $^1$H NMR (400 MHz, DMSO-d$_6$) δ 10.6 (s, 1H), 7.48 (d, J=15.6 Hz, 1H), 7.43 (d, J=11.1 Hz, 2H), 7.40 (d, J=7.5 Hz, 1H), 7.18 (d, J=7.2 Hz, 1H), 7.02-6.92 (m, 2H), 6.68 (d, J=14.7 Hz, 1H), 5.13 (s, 1H), 3.37-3.32 (m, 1H), 2.95 (d, J=15 Hz, 2H), 2.59 (d, J=13.2 Hz, 2H), 1.82 (d, J=7.8 Hz, 3H), 1.70 (d, J=7.8 Hz, 3H), 1.03 (d, J=6.3 Hz, 3H), proton of carboxylic acid not observed; MS (ESI) m/z 467.38 [M+H]+; $[\alpha]^{25}_D$ −90.00 (c 0.5, MeOH).

Example 15A (E)-3-(3,5-Difluoro-4-((1R,3R)-2-(2-fluoro-2-methylpropyl)-7-hydroxy-3-methyl-2,3,4,9-tetrahydro-1H-pyrido[3,4-b]indol-1-yl)phenyl)acrylic acid (15A)

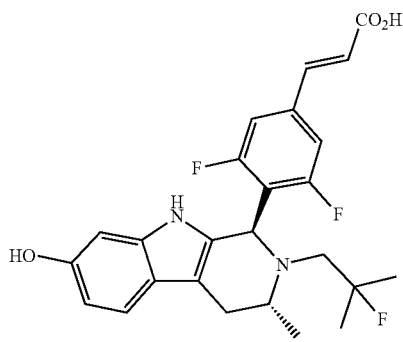 [SMILES: C[C@@H]1Cc2c([nH]c3cc(O)ccc23)[C@@H](c2c(F)cc(/C=C/C(=O)O)cc2F)N1CC(C)(C)F]

Step 1

To a suspension of (R)-2-(((9H-fluoren-9-yl)methoxy)carbonylamino)propanoic acid (10 g, 32.1 mmol) in DCM (100 mL) at 0° C. was added oxalyl chloride (4.3 mL, 48.2 mmol), followed by a catalytic amount of DMF (0.18 mL, 10 mol %). The mixture was stirred at room temperature for 4 h and then concentrated. The resulting residue was dissolved in toluene and concentrated repeatedly (2×50 mL) to afford crude compound (9H-fluoren-9-yl)methyl (R)-(1-chloro-1-oxopropan-2-yl)carbamate (22 g, crude weight) as a pale yellow solid.

Step 2

Ethylmagnesium bromide (44 mL, 134.5 mmol, 3.0M solution in $Et_2O$) was added dropwise at 0° C. to a solution of 6-(benzyloxy)-1H-indole (10 g, 44.8 mmol) over a period of 1 h in DCM (100 mL) under an atmosphere of argon. The resultant reaction mixture was warmed to room temperature and stirred for an additional 1 h. The above reaction mixture was cooled to 0° C. and treated with a solution of (9H-fluoren-9-yl)methyl (R)-(1-chloro-1-oxopropan-2-yl)carbamate (22 g, 67.2 mmol, crude) in DCM (100 mL) under an atmosphere of argon. After the addition was complete, the reaction was warmed to room temperature and stirred at rt for 12 h. The reaction mixture was cooled back to 0° C. and the excess of unreacted Grignard reagent was destroyed with aqueous HCl (200 mL, 2N). The organic layer was separated and the aqueous layer was extracted with $CH_2Cl_2$ (2×200 mL). The combined organic layer was washed with water followed by brine, dried over sodium sulfate, filtered and concentrated to afford (R)-(9H-Fluoren-9-yl)methyl 1-(6-(benzyloxy)-1H-indol-3-yl)-1-oxopropan-2-ylcarbamate (22.0 g, 42.6 mmol, crude) as a brown liquid. MS (ESI) m/z 517.35 [M+H]$^+$.

Step 3

To a solution of (R)-(9H-Fluoren-9-yl)methyl 1-(6-(benzyloxy)-1H-indol-3-yl)-1-oxopropan-2-ylcarbamate (20 g, 38.75 mmol, crude) in a mixture of acetonitrile/IPA (7:1, total of 200 mL) was added sodium borohydride (14.3 g, 388 mmol) in several portions under argon atmosphere at 0° C. The mixture was heated to reflux for 15 h. After completion of the reaction based on complete consumption of starting material (as monitored by TLC), the reaction mixture was cooled back to 0° C. Methanol (50 mL) was added to destroy excess reagent and the resulting mixture was stirred at rt for 30 min. Water (500 mL) was added and the aqueous phase was extracted with ethyl acetate (3×200 mL). The combined organic layer was washed with water, brine, dried over sodium sulfate, filtered and concentrated under reduced pressure. The residue was triturated with pentane to afford crude compound, (R)-1-(6-(benzyloxy)-1H-indol-3-yl)propan-2-amine (9 g, 25.4 mmol), as an off white solid used as is in the subsequent reaction. MS (ESI) m/z 281.47 [M+H]$^+$.

Step 4

To a stirred solution of (R)-1-(6-(benzyloxy)-1H-indol-3-yl)propan-2-amine (9 g, 32.1 mmol, crude) in 1,4-dioxane (80 mL) was added 2-fluoro-2-methylpropyl trifluoromethanesulfonate (7.9 g, 35.4 mmol) and N,N-diisopropylethylamine (8.8 mL, 48.21 mmol). The reaction was heated to 90° C. for 3 h, cooled to room temperature and diluted with water (50 mL). The aqueous layer was extracted with EtOAc (2×50 mL). The combined organic phase was dried over sodium sulfate, filtered and concentrated. The resultant residue was purified by flash chromatography ($SiO_2$, 50% ethyl acetate in petroleum ethers) to afford (R)—N-(1-(6-(benzyloxy)-1H-indol-3-yl)propan-2-yl)-2-fluoro-2-methylpropan-1-amine (4 g, 11.3 mmol, 26% yield over 3 steps). MS (ESI) m/z 355.37 [M+H]$^+$.

Step 5

To a stirred solution of (R)—N-(1-(6-(benzyloxy)-1H-indol-3-yl)propan-2-yl)-2-fluoro-2-methylpropan-1-amine (4 g, 11.3 mmol) in EtOAc (50 mL) was added 10% wet Pd/C (800 mg). The reaction was stirred at rt for 12 h under 1 atm of hydrogen gas. The mixture was filtered through a Celite pad. The filtrate was concentrated under reduced pressure to afford (R)-3-(2-(2-fluoro-2-methylpropylamino)propyl)-1H-indol-6-ol (1.8 g, 6.81 mmol, 64% yield). MS (ESI) m/z 265.17 [M+H]$^+$.

Step 6

To a stirred solution of (R)-3-(2-(2-fluoro-2-methylpropylamino)propyl)-1H-indol-6-ol (1.8 g, 6.81 mmol) in toluene (30 mL) were added methyl (E)-3-(3,5-difluoro-4-formylphenyl) acrylate (1.69 g, 7.49 mmol) and AcOH (0.2 mL, 3.5 mmol) and the mixture was heated at 90° C. for 5 h. The reaction mixture was diluted with EtOAc and washed with water. The organic layer was separated and the aqueous layer was extracted with EtOAc (2×20 mL). The combined organic phase was dried over sodium sulfate, filtered and concentrated. The resultant residue was purified by flash chromatography ($SiO_2$, 20% ethyl acetate/hexane) to afford ((E)-methyl 3-(3,5-difluoro-4-((1R,3R)-2-(2-fluoro-2-methylpropyl)-7-hydroxy-3-methyl-2,3,4,9-tetrahydro-1H-pyrido[3,4-b]indol-1-yl)phenyl)acrylate (1.2 g, 19.4 mmol, 37% yield) as an off white solid. MS (ESI) m/z 473.38 [M+H]$^+$.

Step 7

To a stirred solution of (E)-methyl 3-(3,5-difluoro-4-((1R,3R)-2-(2-fluoro-2-methylpropyl)-7-hydroxy-3-methyl-2,3, 4,9-tetrahydro-1H-pyrido[3,4-b]indol-1-yl)phenyl)acrylate (800 mg, 16.9 mmol) in THF/water (1:1, 15 mL) at 0° C. was added LiOH (232 mg, 10.2 mmol). The mixture was stirred at rt for 5 h. The organic volatiles were removed under reduced pressure. The residue was acidified with an aqueous hydrogen chloride solution (1N) at 0° C. The reaction mixture was diluted with EtOAc and washed with water. The combined organic layer was dried over sodium sulfate, filtered and concentrated. The crude compound was purified by reverse phase prep HPLC [mobile phase: (A) 10 mM aqueous ammonium bicarbonate, (B) Acetonitrile; Flow: 19 mL/min. Column: Inertsil $C_{18}$ (250×20 mm), 5 m] to afford the ammonium salt of (E)-3-(3,5-difluoro-4-((1R,3R)-2-(2-fluoro-2-methylpropyl)-7-hydroxy-3-methyl-2,3,4,9-tetrahydro-1H-pyrido[3,4-b]indol-1-yl)phenyl) acrylic acid (40 mg, 0.08 mmol, 5% yield) as an orange solid after lyophilization. $^1$H NMR (300 MHz, DMSO-$d_6$) δ 10.2 (s, 1H), 7.42 (d, J=15.0 Hz, 1H), 7.38 (d, J=10.5 Hz, 2H), 7.15 (d, J=8.7 Hz, 1H), 6.64 (d, J=15.8 Hz, 1H), 6.57 (d, J=2.1 Hz, 1H), 6.47 (dd, J=8.1, 1.8 Hz, 1H), 5.13 (s, 1H), 3.53-3.45 (m, 1H), 2.91-2.79 (m, 2H), 2.47-2.26 (m, 2H), 1.19 (d, J=20.4 Hz, 3H), 1.12 (d, J=21.0 Hz, 3H), 1.03 (d, J=6.3 Hz, 3H), carboxylic acid and phenolic protons were not observed; MS (ESI) m/z 458.97 [M+H]$^+$.

Example 16A (E)-3-(3,5-Difluoro-4-((1R,3R)-2-((3-fluorooxetan-3-yl)methyl)-3-methyl-2,3,4,9-tetrahydro-1H-pyrido[3,4-b]indol-1-yl)phenyl)acrylic acid (16A)

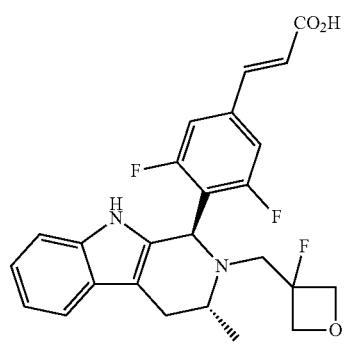 [SMILES: C[C@@H]1Cc2c([nH]c3ccccc23)[C@@H](c2c(F)cc(/C=C/C(=O)O)cc2F)N1CC1(F)COC1]

Step 1

To a stirred solution of (R)-1-(1H-indol-3-yl)propan-2-amine (0.15 g, 0.861 mmol) in dioxane (2.87 ml) was added (3-fluorooxetan-3-yl)methyl trifluoromethanesulfonate (0.226 g, 0.947 mmol) and N,N-diisopropylethylamine (0.300 ml, 1.722 mmol) and the mixture was stirred at 90° C. for 4 h. The reaction mixture was diluted with ethyl acetate (10 mL) and washed with saturated aqueous NaHCO$_3$ solution (5 mL). The combined organics were dried over sodium sulfate, filtered and concentrated. The resultant residue was purified by flash chromatography (SiO$_2$, 60-80% ethyl acetate/hexane) to afford (R)—N-((3-fluorooxetan-3-yl)methyl)-1-(1H-indol-3-yl)propan-2-amine (0.18 g, 80% yield). MS (APCI) m/z 263.15 [M+H]$^+$.

Step 2

To a stirred solution of (R)—N-((3-fluorooxetan-3-yl)methyl)-1-(1H-indol-3-yl)propan-2-amine (0.10 g, 0.381 mmol) in toluene (1.91 ml) were added (E)-ethyl 3-(3,5-difluoro-4-formylphenyl)acrylate (0.097 g, 0.404 mmol)acetic acid (0.046 g, 0.762 mmol). The mixture was stirred at 90° C. for 5 h. The reaction mixture was diluted with EtOAc, the organic layer was separated and then washed with water. The combined organic layer was dried over sodium sulfate, filtered and concentrated. The resulting residue was purified by flash chromatography (SiO$_2$, 15-60% ethyl acetate/hexane) to afford ethyl (E)-3-(3,5-difluoro-4-((1R,3R)-2-((3-fluorooxetan-3-yl)methyl)-3-methyl-2,3,4,9-tetrahydro-1H-pyrido[3,4-b]indol-1-yl)phenyl)acrylate (0.11 g, 60% yield) as a pale yellow solid. MS (APCI) m/z 485.2 [M+H]$^+$.

Step 3

To a stirred solution of (E)-ethyl 3-(3,5-difluoro-4-((1R,3R)-2-((3-fluorooxetan-3-yl)methyl)-3-methyl-2,3,4,9-tetrahydro-1H-pyrido[3,4-b]indol-1-yl)phenyl)acrylate (0.08 g, 0.165 mmol) in a mixture of methanol:THF:water (1:1:1, total of 3 mL) at 0° C. was added sodium hydroxide (0.020 g, 0.495 mmol) and the mixture was stirred at rt for 2 h. The reaction mixture was concentrated and the residue was acidified with an aqueous solution of citric acid (1M) at 0° C. to adjust pH to 5. The precipitate that formed was filtered, washed with water and dried. The resulting solid was dissolved in DMSO (1 mL) and purified by reversed phase HPLC, using 10-50% acetonitrile (contains 0.1% formic acid) in water (contains 0.1% formic acid) to afford (E)-3-(3,5-difluoro-4-((1R,3R)-2-((3-fluorooxetan-3-yl)methyl)-3-methyl-2,3,4,9-tetrahydro-1H-pyrido[3,4-b]indol-1-yl)phenyl)acrylic acid (0.035 g, 46% yield) after lyophilization $^1$H NMR (400 MHz, DMSO-$d_6$) δ 12.6 (s, 1H), 10.6 (s, 1H), 7.54 (d, J=16 Hz, 1H), 7.47 (d, J=8 Hz, 2H), 7.42 (d, J=8 Hz, 1H), 7.20 (d, J=8 Hz, 1H), 7.03-6.92 (m, 2H), 6.67 (d, J=16 Hz, 1H), 5.28 (s, 1H), 4.61-4.44 (m, 3H), 4.35-4.25 (m, 1H), 2.87-2.73 (m, 2H), 2.63-2.56 (m, 2H), 1.24-1.14 (m, 2H), 1.12 (d, J=8 Hz, 3H); MS (APCI) m/z 457.17 [M+H]$^+$.

Example 17A ((E)-3-(3,5-Difluoro-4-((1R,3R)-3-methyl-2-(oxetan-3-ylmethyl)-2,3,4,9-tetrahydro-1H-pyrido[3,4-b]indol-1-yl)phenyl)acrylic acid (17A)

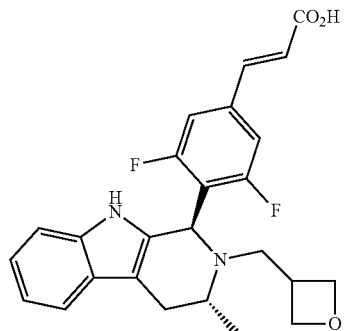

Step 1

To a stirred solution of (R)-1-(1H-indol-3-yl)propan-2-amine (0.15 g, 0.861 mmol) in dioxane (2.87 ml) were added oxetan-3-ylmethyl trifluoromethanesulfonate (0.218 g, 0.990 mmol) and N,N-diisopropylethylamine (0.330 ml, 1.89 mmol). The mixture was stirred at 90° C. for 4 h. The reaction mixture was diluted with ethyl acetate (10 mL) and washed with saturated aqueous NaHCO$_3$ solution (5 mL). The combined organic layers were dried over sodium sulfate and concentrated. The resulting residue was purified by flash chromatography (SiO$_2$, 0-10% MeOH in DCM) to afford (R)-1-(1H-indol-3-yl)-N-(oxetan-3-ylmethyl)propan-2-amine (0.11 g, 0.450 mmol, 52% yield) MS (APCI) m/z 245.16 [M+H]+.

Step 2

To a stirred solution of (R)-1-(1H-indol-3-yl)-N-(oxetan-3-ylmethyl)propan-2-amine (0.064 g, 0.262 mmol) in toluene (1.3 ml) were added (E)-ethyl 3-(3,5-difluoro-4-formylphenyl)acrylate (0.067 g, 0.278 mmol) and acetic acid (0.031 g, 0.524 mmol) The reaction was stirred at 90° C. for 5 h. The reaction mixture was diluted with EtOAc and washed with water. The combined organic phase was dried over sodium sulfate, filtered and concentrated. The resulting residue was purified by flash chromatography (SiO$_2$, 15-60% EtOAc in hexane) to afford ethyl (E)-3-(3,5-difluoro-4-((1R,3R)-3-methyl-2-(oxetan-3-ylmethyl)-2,3,4,9-tetrahydro-1H-pyrido[3,4-b]indol-1-yl)phenyl)acrylate (0.061 g, 0.131 mmol, 50% yield) as an pale yellow solid. MS (APCI) m/z 467.21 [M+H]$^+$.

Step 3

To a stirred solution of (E)-ethyl 3-(3,5-difluoro-4-((1R,3R)-3-methyl-2-(oxetan-3-ylmethyl)-2,3,4,9-tetrahydro-1H-pyrido[3,4-b]indol-1-yl)phenyl)acrylate (0.06 g, 0.129 mmol) in a mixture of methanol:THF:water (1:1:1, total of 3 mL) at 0° C. was added sodium hydroxide (0.015 g, 0.386 mmol). The reaction mixture was stirred at rt for 2 h and then concentrated. The resulting residue was acidified with a aqueous solution of citric acid (1M) at 0° C. to carefully adjust pH to 5. The precipitate that formed was dissolved in EtOAc. The organic phase was washed with water, dried over sodium sulfate, filtered and concentrated. The resulting solid was dissolved in DMSO (1 mL) and purified by reversed-phase HPLC, using 10-60% acetonitrile (contains 0.1% formic acid) in water (contains 0.1% formic acid). The resulting fractions were lyophilized under reduced pressure to afford (E)-3-(3,5-difluoro-4-((1R,3R)-3-methyl-2-(oxetan-3-ylmethyl)-2,3,4,9-tetrahydro-1H-pyrido[3,4-b]indol-1-yl)phenyl)acrylic acid (0.009 g, 16% yield) $^1$H NMR (400 MHz, DMSO-d$_6$) δ 12.6 (s, 1H), 10.6 (s, 1H), 7.55 (d, J=16 Hz, 1H), 7.48 (d, J=8 Hz, 2H), 7.40 (d, J=8 Hz, 1H), 7.20 (d, J=8 Hz, 1H), 7.02-6.92 (m, 2H), 6.67 (d, J=16 Hz, 1H), 5.10 (s, 1H), 4.62-4.51 (m, 2H), 4.16 (t, J=5.9 Hz, 1H), 3.93 (t, J=5.9 Hz, 1H), 3.21-3.11 (m, 1H), 3.02-2.90 (m, 2H), 2.86-2.76 (m, 1H), 2.64-2.53 (m, 2H), 1.07 (d, J=4 Hz, 3H); MS (APCI) m/z 439.18 [M+H]$^+$.

Example 18A (E)-3-(3,5-Difluoro-4-((1R,3R)-3-methyl-2-((3-methyloxetan-3-yl)methyl)-2,3,4,9-tetrahydro-1H-pyrido[3,4-b]indol-1-yl)phenyl)acrylic acid (18A)

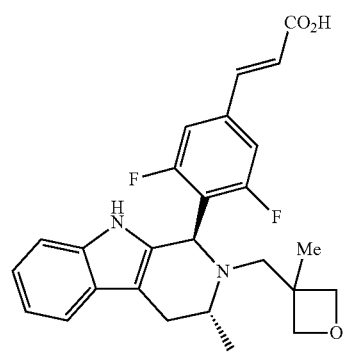 [SMILES: C[C@@H]1Cc2c([nH]c3ccccc23)[C@@H](c2c(F)cc(/C=C/C(=O)O)cc2F)N1CC1(C)COC1]

Step 1

To a stirred solution of (R)-1-(1H-indol-3-yl)propan-2-amine (0.22 g, 1.26 mmol) in dichloromethane (5 ml) was added HATU (0.386 g, 1.64 mmol) and N,N-diisopropylethylamine (0.506 ml, 2.90 mmol) at rt and the mixture was stirred for 10 min. 3-Methyloxetane-3-carboxylic acid (0.161 g, 1.39 mmol) was added and the reaction was stirred at rt for 16 h. The reaction mixture was diluted with EtOAc and washed with an aqueous saturated NaHCO$_3$ solution. The organic layer was separated, dried over Na$_2$SO$_4$, filtered and concentrated. The resulting residue was purified by flash chromatography (SiO$_2$, 0-10% MeOH in DCM) to afford (R)—N-(1-(1H-indol-3-yl)propan-2-yl)-3-methyloxetane-3-carboxamide (0.30 g, 1.10 mmol, 87% yield) MS (APCI) m/z 273.15 [M+H]$^+$.

Step 2

To a stirred solution of (R)—N-(1-(1H-indol-3-yl)propan-2-yl)-3-methyloxetane-3-carboxamide (0.22 g, 0.808 mmol) in THF (3 ml) was added LAH (2.83 ml, 5.65 mmol, 2M in THF) dropwise at 0° C. and the mixture was heated to reflux for 48 hours. The completion of the reaction (as monitored by TLC) was gauged by consumption of starting material. The reaction mixture was quenched slowly with ice cold water (0.25 mL), an aqueous solution of 15% NaOH solution (0.50 mL) and water (0.75 mL). The resulting residue was extracted with EtOAc (2×20 mL) and the separated organic phase was dried over Na$_2$SO$_4$, filtered, and concentrated. The resulting residue was purified by column chromatography [SiO$_2$, 0-50% DCM/(DCM:7M ammonia in methanol (9:1 v/v))] to afford (R)-1-(1H-indol-3-yl)-N-((3-methyloxetan-3-yl)methyl)propan-2-amine (0.12 g, 57% yield) MS (APCI) m/z 259.17 [M+H]$^+$.

Step 3

To a stirred solution of (R)-1-(1H-indol-3-yl)-N-((3-methyloxetan-3-yl)methyl)propan-2-amine (0.10 g, 0.387 mmol) in toluene (1.91 mL) were added (E)-ethyl 3-(3,5-difluoro-4-formylphenyl)acrylate (0.099 g, 0.410 mmol) and acetic acid (0.046 g, 0.774 mmol). The reaction mixture was stirred at 90° C. for 5 h and cooled to rt. The mixture was diluted with EtOAc and washed with water. The combined organic layers were dried over sodium sulfate, filtered and concentrated. The resulting residue was purified by flash chromatography (SiO$_2$, 15-60% ethyl acetate in hexane) to afford ethyl (E)-3-(3,5-difluoro-4-((1R,3R)-3-methyl-2-((3-methyloxetan-3-yl)methyl)-2,3,4,9-tetrahydro-1H-pyrido[3,4-b]indol-1-yl)phenyl)acrylate (0.11 g, 59% yield) as a pale yellow solid. MS (APCI) m/z 481.22 [M+H]$^+$.

Step 4

To a stirred solution of (E)-ethyl 3-(3,5-difluoro-4-((1R,3R)-3-methyl-2-((3-methyloxetan-3-yl)methyl)-2,3,4,9-tetrahydro-1H-pyrido[3,4-b]indol-1-yl)phenyl)acrylate (0.061 g, 0.127 mmol) in a mixture of methanol:THF:water (1:1:1, total of 3 mL) at 0° C. was added sodium hydroxide (0.020 g, 0.495 mmol). The reaction was stirred at rt for 2 h. The resulting mixture was concentrated under reduced pressure and the residue was acidified with an aqueous solution of citric acid (1M) at 0° C. to adjust pH to 5. The precipitate that formed was filtered, washed with water and dried. The resulting solid was dissolved in DMSO (1 mL) and purified by reversed phase HPLC using 10-60% acetonitrile (contains 0.1% formic acid) in water (contains 0.1% formic acid) to afford (E)-3-(3,5-difluoro-4-((1R,3R)-3-methyl-2-((3-methyloxetan-3-yl)methyl)-2,3,4,9-tetrahydro-1H-pyrido[3,4-b]indol-1-yl)phenyl)acrylic acid (0.03 g, 52% yield) after lyophilization. $^1$H NMR (400 MHz, DMSO-d$_6$) δ 10.6 (s, 1H), 7.54 (d, J=16 Hz, 1H), 7.46 (d, J=8 Hz, 1H), 7.40 (d, J=8 Hz, 1H), 7.18 (d, J=8 Hz, 1H), 7.03-6.92 (m, 2H), 6.66 (d, J=16 Hz, 1H), 5.07 (s, 1H), 4.40 (d, J=8 Hz, 1H), 4.16 (t, J=8 Hz, 1H), 4.05-4.00 (m, 1H), 3.08-2.83 (m, 4H), 2.63-2.55 (m, 1H), 2.36-2.30 (m, 1H), 1.21 (s, 3H), 1.03 (d, J=4 Hz, 3H), proton of carboxylic acid not observed; MS (APCI) m/z 453.19 [M+H]$^+$.

Example 19A (E)-3-(4-((3S)-3-(Difluoromethyl)-2-(tetrahydrofuran-3-yl)-2,3,4,9-tetrahydro-1H-pyrido[3,4-b]indol-1-yl)-3,5-difluorophenyl)acrylic acid (19A)

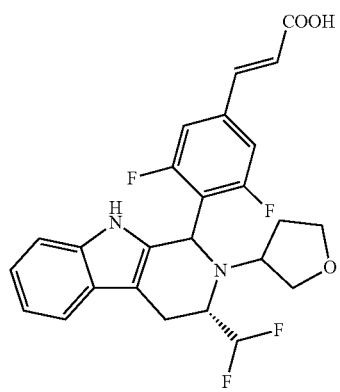 [SMILES: O=C(O)/C=C/c1cc(F)c(C2c3[nH]c4ccccc4c3C[C@@H](C(F)F)N2C2CCOC2)c(F)c1]

Step 1

To a stirred solution of (S)-2-amino-3-(1H-indol-3-yl)propan-1-ol (0.91 g, 4.78 mmol) in DCM (12 ml) were added imidazole (0.977 g, 14.4 mmol) and a solution of t-butylchlorodiphenylsilane (1.578 g, 5.74 mmol) in DCM (6 mL) at 0° C. The mixture was stirred for 18 h at rt. A saturated aqueous NaHCO$_3$ solution was added and the mixture was extracted with DCM. The organic layers were separated, washed with brine, dried (MgSO$_4$), filtered and concentrated. The residue was purified by flash chromatography (SiO$_2$, 0-15% methanol in DCM) to afford (S)-1-((tert-butyldiphenylsilyl)oxy)-3-(1H-indol-3-yl)propan-2-amine (1.69 g, 3.94 mmol, 82% yield) MS (APCI) m/z 429.23 [M+H]$^+$.

Step 2

To a stirred solution of (S)-1-((tert-butyldiphenylsilyl)oxy)-3-(1H-indol-3-yl)propan-2-amine (1.3 g, 3.03 mmol) in ethanol (10 mL) was added dihydrofuran-3(2H)-one (0.313 g, 3.64 mmol) and the mixture was heated at 50° C. for 1 h. The reaction was cooled to 0° C. Sodium borohydride (0.172 g, 4.55 mmol) was added and after stirring for 2 h, the mixture was concentrated. Ethyl acetate and a saturated solution of ammonium chloride were added. The organic layer was separated, dried over sodium sulfate, filtered and concentrated. The residue was purified by flash chromatography (SiO$_2$, 0-10% MeOH in DCM) to obtain N—((S)-1-((tert-butyldiphenylsilyl)oxy)-3-(1H-indol-3-yl)propan-2-yl)tetrahydrofuran-3-amine (1.20 g, 2.41 mmol, 79% yield). MS (APCI) m/z 499.3 [M+H]$^+$.

Step 3

To a stirred solution of N—((S)-1-((tert-butyldiphenylsilyl)oxy)-3-(1H-indol-3-yl)propan-2-yl)tetrahydrofuran-3-amine (0.75 g, 1.50 mmol) in toluene (3 mL) were added (E)-ethyl 3-(3,5-difluoro-4-formylphenyl)acrylate (0.43 g, 1.80 mmol) and acetic acid (0.18 g, 3.01 mmol) The reaction mixture was heated at 85° C. for 4 h and, after cooling to rt, was diluted with EtOAc and washed with water. The organic layer was separated, dried over sodium sulfate, filtered and concentrated. The resulting residue was purified by flash chromatography (SiO$_2$, 0-30% ethyl acetate/hexanes) to afford (E)-ethyl 3-(4-((1R,3S)-3-(((tert-butyldiphenylsilyl)oxy)methyl)-2-(tetrahydrofuran-3-yl)-2,3,4,9-tetrahydro-1H-pyrido[3,4-b]indol-1-yl)-3,5-difluorophenyl)acrylate (0.50 g, 0.694 mmol, 46% yield) as a mixture of isomers. MS (APCI) m/z 721.32 [M+H]$^+$.

Step 4

To a stirred solution of (E)-ethyl 3-(4-((1R,3S)-3-(((tert-butyldiphenylsilyl)oxy)methyl)-2-(tetrahydrofuran-3-yl)-2,3,4,9-tetrahydro-1H-pyrido[3,4-b]indol-1-yl)-3,5-difluorophenyl)acrylate (0.80 g, 1.110 mmol) in THF (3.70 mL) was added dropwise a solution of tetrabutylammonium fluoride (1.33 ml, 1.33 mmol, 1M in THF). The mixture was stirred at rt for 36 h. THF was removed under reduced pressure and DCM was added. The organic layer was washed with water, separated, and concentrated. The resulting residue was purified by flash chromatography (SiO$_2$, 20-60% ethyl acetate/hexanes) to afford (E)-ethyl 3-(3,5-difluoro-4-((1R,3S)-3-(hydroxymethyl)-2-(tetrahydrofuran-3-yl)-2,3,4,9-tetrahydro-1H-pyrido[3,4-b]indol-1-yl)phenyl)acrylate (0.30 g, 0.622 mmol, 56% yield) as a mixture of isomers. MS (APCI) m/z 483.20 [M+H]+.

Step 5

To a solution under nitrogen of (E)-ethyl 3-(3,5-difluoro-4-((1R,3S)-3-(hydroxymethyl)-2-(tetrahydrofuran-3-yl)-2,3,4,9-tetrahydro-1H-pyrido[3,4-b]indol-1-yl)phenyl)acrylate (0.10 g, 0.207 mmol) in dimethyl sulfoxide (0.80 mL) was added IBX (0.073 g, 0.259 mmol) and the mixture was stirred for 16 hours at room temperature. The mixture was diluted with EtOAc and washed successively with an aqueous solution of 5% sodium bicarbonate, water and brine. The organic extracts were dried over sodium sulfate, filtered and concentrated to give crude (E)-ethyl 3-(3,5-difluoro-4-(3S)-(3-formyl-2-(tetrahydrofuran-3-yl)-2,3,4,9-tetrahydro-1H-pyrido[3,4-b]indol-1-yl)phenyl)acrylate (0.06 g, 0.125 mmol, 60% yield) as a mixture of isomers. MS (APCI) m/z 483.20 [M+H]+.

Step 6

To a stirred solution of (E)-ethyl 3-(3,5-difluoro-4-(3S)-((3-formyl-2-(tetrahydrofuran-3-yl)-2,3,4,9-tetrahydro-1H-pyrido[3,4-b]indol-1-yl)phenyl)acrylate (0.055 g, 0.114 mmol) in DCM (0.382 ml) was added Deoxofluor (0.085 ml, 0.229 mmol) dropwise at 0° C. The mixture was stirred at rt for 3 h. A saturated aqueous solution of ammonium chloride was added and the resulting mixture was extracted with DCM (5×10 mL). The organic layer was separated, dried over sodium sulfate and filtered. The solvent was evaporated and crude residue was purified by flash chromatography (SiO$_2$, 20-50% ethyl acetate/hexane) to obtain (E)-ethyl 3-(4-((3S)-3-(difluoromethyl)-2-(tetrahydrofuran-3-yl)-2,3,4,9-tetrahydro-1H-pyrido[3,4-b]indol-1-yl)-3,5-difluorophenyl)acrylate (0.010 g, 17% yield) MS (APCI) m/z 503.19 [M+H]+.

Step 7

To a stirred solution of (E)-ethyl 3-(4-((3S)-3-(difluoromethyl)-2-(tetrahydrofuran-3-yl)-2,3,4,9-tetrahydro-1H-pyrido[3,4-b]indol-1-yl)-3,5-difluorophenyl)acrylate (0.010 g, 0.020 mmol) in a mixture of methanol:THF:water (1:1:1, total of 3 mL) at 0° C. was added sodium hydroxide (3.98 mg, 0.100 mmol). The mixture was stirred at rt for 2 h and then concentrated. The residue was treated with an aqueous solution of citric acid (1M) at 0° C. to adjust pH to 5. The precipitate was extracted with EtOAc and the organic solution was concentrated. The resulting solid was dissolved in DMSO (1 mL) and purified by reversed phase HPLC using 10-50% acetonitrile (containing 0.1% formic acid) in water (containing 0.1% formic acid) to afford (E)-3-((3S)-4-(3-(difluoromethyl)-2-(tetrahydrofuran-3-yl)-2,3,4,9-tetrahydro-1H-pyrido[3,4-b]indol-1-yl)-3,5-difluorophenyl)acrylic acid (0.004 g, 8.43 mol, 42% yield) after lyophilization. MS (APCI) m/z 475.16 [M+H]+.

Example 20

(E)-3-(3,5-Difluoro-4-(2'-(tetrahydrofuran-3-yl)-1',2',4',9'-tetrahydrospiro[cyclopropane-1,3'-pyrido[3,4-b]indol]-1'-yl)phenyl)acrylic acid (20)

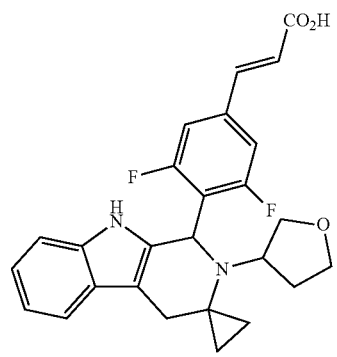 [SMILES: O=C(O)/C=C/c1cc(F)c(C2c3[nH]c4ccccc4c3CC3(CC3)N2C2CCOC2)c(F)c1]

Step 1

To a solution of 2-(1H-indol-3-yl)acetonitrile (2 g, 12.81 mmol) and methyltitanium triisopropoxide (18.57 ml, 18.57 mmol, 1M in THF) in THF (85 ml) was added dropwise ethylmagnesium bromide solution (6.40 ml, 19.1 mmol, 3M in diethyl ether) under argon. After stirring for 2 h, boron trifluoride diethyl ether complex (3.16 ml, 25.6 mmol) was added dropwise and the mixture was stirred for 45 min at rt. An aqueous solution of HCl (120 mL, 1M) was added followed by EtOAc (100 mL) and an aqueous solution of NaOH (120 mL, 3M). The aqueous phase was extracted with EtOAc (3×30 mL). The organic phase was dried over magnesium sulfate, filtered and concentrated. The crude material was purified by flash chromatography [SiO$_2$, 0-50% DCM/(DCM:7M ammonia in MeOH (9:1 v/v))] to obtain 1-((1H-indol-3-yl)methyl)cyclopropane-1-amine (0.90 g, 37% yield). MS (APCI) m/z 187.12 [M+H]+.

Step 2

To a stirred solution of 1-((1H-indol-3-yl)methyl)cyclopropanamine (0.30 g, 1.61 mmol) in DCE (5.37 ml) was added dihydrofuran-3(2H)-one (0.180 g, 2.094 mmol) and sodium triacetoxyborohydride (0.683 g, 3.22 mmol) at 0° C. After being stirred at rt for 2 h, the mixture was concentrated. Ethyl acetate (30 mL) and a saturated aqueous solution of ammonium chloride were added. The organic phase was separated, dried over sodium sulfate and concentrated. The residue was purified by flash chromatography (SiO$_2$, 0-50% DCM/(DCM:7M ammonia in MeOH (9:1 v/v))) to afford N-(1-((1H-indol-3-yl)methyl)cyclopropyl)tetrahydrofuran-3-amine (0.27 g, 1.05 mmol, 65% yield) as a yellowish-white solid. MS (APCI) m/z 257.16 [M+H]+.

Step 3

To a stirred solution of N-(1-((1H-indol-3-yl)methyl)cyclopropyl)tetrahydrofuran-3-amine (0.078 g, 0.304 mmol) in toluene (1 mL) were added (E)-ethyl 3-(3,5-difluoro-4-formylphenyl)acrylate (0.08 g, 0.335 mmol) and acetic acid (0.04 g, 0.61 mmol). The reaction was stirred at 90° C. for 4 h, cooled to rt, diluted with EtOAc and washed with water.

The organic layer was separated, dried over sodium sulfate, filtered and concentrated. The residue was purified by flash chromatography (SiO$_2$, 60-100% EtOAc in hexane) to afford (E)-ethyl 3-(3,5-difluoro-4-(2'-(tetrahydrofuran-3-yl)-1',2',4',9'-tetrahydrospiro[cyclopropane-1,3'-pyrido[3,4-b]indol]-1'-yl)phenyl)acrylate (0.06 g, 41% yield) as a mixture of isomers. MS (APCI) m/z 479.21 [M+H]$^+$.

Step 4

To a stirred solution of (E)-ethyl 3-(3,5-difluoro-4-(2'-(tetrahydrofuran-3-yl)-1',2',4',9'-tetrahydrospiro[cyclopropane-1,3'-pyrido[3,4-b]indol]-1'-yl)phenyl)acrylate (0.07 g, 0.146 mmol) in a mixture of methanol:THF:water (1:1:1, total of 3 mL) at 0° C. was added sodium hydroxide (0.075 g, 1.873 mmol). The mixture was stirred at rt for 2 h and then concentrated. The residue was acidified with an aqueous solution of citric acid (1M) at 0° C. to adjust pH to 5. The resulting mixture was extracted with EtOAc and washed with water. The organic layer was concentrated and dried under reduced pressure to afford (E)-3-(3,5-difluoro-4-(2'-(tetrahydrofuran-3-yl)-1',2',4',9'-tetrahydrospiro[cyclopropane-1,3'-pyrido[3,4-b]indol]-1'-yl)phenyl)acrylic acid (0.025 g, 38% yield) as a mixture of isomers. MS (APCI) m/z 451.18 [M+H]$^+$.

Example 21A (E)-3-(3,5-Difluoro-4-((1R,3R)-6-fluoro-2-(2-fluoro-2-methylpropyl)-3-methyl-2,3,4,9-tetrahydro-1H-pyrido[3,4-b]indol-1-yl)phenyl)acrylic acid (21A)

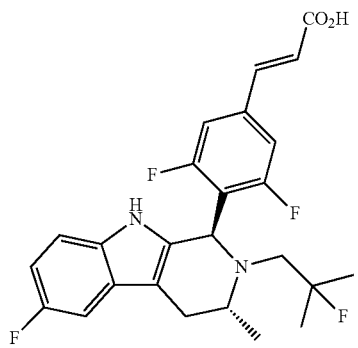 [SMILES: C[C@@H]1Cc2c([nH]c3ccc(F)cc23)[C@@H](c2c(F)cc(/C=C/C(=O)O)cc2F)N1CC(C)(C)F]

Step 1

To a suspension of (R)-2-(((9H-fluoren-9-yl)methoxy)carbonylamino)propanoic acid (10 g, 32.2 mmol) in DCM (100 mL) at 0° C. was added oxalyl chloride (4.3 mL, 48.2 mmol) followed by a catalytic amount of DMF (0.18 mL, 10 mol %). The mixture was stirred at rt for 4 h and concentrated. The resultant residue was treated with toluene and concentrated (2×50 mL) to afford crude compound (9H-fluoren-9-yl)methyl 1-chloro-1-oxopropan-2-ylcarbamate (22 g, crude weight) as a pale yellow solid.

Step 2

Ethylmagnesium bromide (30.5 mL, 91.7 mmol, 3.0M solution in Et$_2$O) was added dropwise to a solution of 5-fluoro-1H-indole (4.13 g, 44.8 mmol) in DCM (100 mL) at 0° C. over a period of 0.5 h under an atmosphere of argon. After being stirred at rt for 1 h, the reaction mixture was cooled to 0° C. and treated with a solution of (9H-fluoren-9-yl)methyl 1-chloro-1-oxopropan-2-ylcarbamate (15 g, 45.59 mmol) in DCM (100 mL) under an atmosphere of argon. After being stirred at rt for another 12 h, the resulting mixture was then cooled to 0° C. and quenched by 2N HCl (100 mL). The organic layer was separated and the aqueous layer was extracted with CH$_2$Cl$_2$ (2×200 mL). The combined organic layers were washed with water and brine, dried over sodium sulfate, filtered and concentrated. The crude product was triturated with 10% Et$_2$O in n-pentane to afford (9H-fluoren-9-yl)methyl (R)-(1-(5-fluoro-1H-indol-3-yl)-1-oxopropan-2-yl)carbamate (3.99 g, 9.32 mmol, 31% yield) as a brown solid. MS (ESI) m/z 429.04 [M+H]$^+$.

Step 3

To a stirred solution of (9H-fluoren-9-yl)methyl (R)-(1-(5-fluoro-1H-indol-3-yl)-1-oxopropan-2-yl)carbamate (950 mg, 2.21 mmol) in a mixture of acetonitrile/IPA (4:1, total of 10 mL) was added sodium borohydride (839 mg, 22.2 mmol) in several portions under an argon atmosphere at 0° C. The mixture was heated at reflux for 15 h. After consumption of starting material as indicated by TLC, the reaction mixture was cooled back to 0° C. Methanol (5 mL) was added to destroy excess reagent and the mixture was stirred at rt for 30 min. Water (100 mL) was added and the aqueous phase was extracted with ethyl acetate (3×100 mL). The combined organic layers were washed with water and brine, dried over sodium sulfate, filtered and concentrated. The residue was triturated with pentane to afford (R)-1-(5-fluoro-1H-indol-3-yl)propan-2-amine (700 mg, 3.64 mmol, crude) as a brown solid. MS (ESI) m/z 193.00 [M+H]$^+$.

Step 4

To a stirred solution of (R)-1-(5-fluoro-1H-indol-3-yl)propan-2-amine (700 mg, 3.64 mmol) in 1,4-dioxane (8 mL) was added 2-fluoro-2-methylpropyl trifluoromethanesulfonate (898 mg, 4.0 mmol) and N—N-diisopropylethylamine (0.95 mL, 5.46 mmol) at 0° C. After being stirred at 90° C. for 5 h, the reaction was cooled to rt and quenched with water (20 mL). The mixture was extracted with ethyl acetate (2×50 mL). The combined organic layers were dried over sodium sulfate, filtered and concentrated. The resultant residue was purified by flash chromatography (SiO$_2$, 50% ethyl acetate in hexanes) to afford (R)-2-fluoro-N-(1-(5-fluoro-1H-indol-3-yl)propan-2-yl)-2-methylpropan-1-amine (340 mg, 1.27 mmol, 35% yield). MS (ESI) m/z 266.90 [M+H]$^+$.

Step 5

To a stirred solution of (R)-2-fluoro-N-(1-(5-fluoro-1H-indol-3-yl)propan-2-yl)-2-methylpropan-1-amine (340 mg, 1.27 mmol) in toluene (5 mL) were added methyl (E)-3-(3,5-difluoro-4-formylphenyl) acrylate (292 mg, 1.29 mmol) and AcOH (0.1 mL, 1.75 mmol) at 0° C. After being stirred at 90° C. for 16 h, the reaction mixture was cooled to rt, diluted with ethyl acetate, and washed with water. The organic layer was separated. The aqueous layer was extracted with ethyl acetate (2×20 mL). The combined organic layers were dried over sodium sulfate, filtered and concentrated. The resultant residue was purified by flash column chromatography (SiO$_2$, 20% ethyl acetate in hexanes) to afford (E)-methyl 3-(3,5-difluoro-4-((1R,3R)-6-fluoro-2-(2-fluoro-2-methylpropyl)-3-methyl-2,3,4,9-tetrahydro-1H-pyrido[3,4-b]indol-1-yl)phenyl)acrylate_(340 mg, 0.71 mmol, 56% yield) as a yellow solid. MS (ESI) m/z 475.57 [M+H]+.

Step 6

To a stirred solution of (E)-methyl 3-(3,5-difluoro-4-((1R, 3R)-6-fluoro-2-(2-fluoro-2-methylpropyl)-3-methyl-2,3,4, 9-tetrahydro-1H-pyrido[3,4-b]indol-1-yl)phenyl)acrylate (240 mg, 0.50 mmol) in THF/water (1:1, total of 15 mL) was added LiOH.H$_2$O (85 mg, 2.02 mmol) at 0° C. After being stirred at rt for 5 h, the solvents were removed under reduced pressure. The residue was acidified with a saturated citric acid solution at 0° C. and extracted with ethyl acetate (3×20 mL). The combined organic layers were dried over sodium sulfate, filtered and concentrated. The resultant residue was triturated with 10% Et$_2$O/n-pentane to give (E)-3-(3,5-difluoro-4-((1R,3R)-6-fluoro-2-(2-fluoro-2-methylpropyl)-3-methyl-2,3,4,9-tetrahydro-1H-pyrido[3,4-b]indol-1-yl)phenyl)acrylic acid (151 mg, 0.32 mmol, 65% yield) as a pale yellow solid. $[\alpha]^{25}_D$ –40.00 (c 0.5, MeOH); Melting point: 128-130° C. $^1$H NMR (300 MHz, DMSO-d$_6$) δ 12.6 (br s, 1H), 10.72 (s, 1H), 7.54 (d, J=15.9 Hz, 1H), 7.46 (d, J=10.2 Hz, 2H), 7.18-7.14 (m, 2H), 6.83 (ddd, J=9.6, 7.2, 2.1 Hz, 1H), 6.67 (d, J=15.9 Hz, 1H), 5.21 (s, 1H), 3.51-3.47 (m, 1H), 2.92-2.81 (m, 2H), 2.58-2.50 (m, 1H), 2.33 (dd, J=23.1, 15.0 Hz, 1H), 1.20 (d, J=21.9 Hz, 3H), 1.12 (d, J=21.6 Hz, 3H), 1.05 (d, J=6.3 Hz, 3H); MS (ESI) m/z 461.53 [M+H]+.

Example 22

(E)-3-(4-(2-(Bicyclo[1.1.1]pentan-1-ylmethyl)-3,3-dimethyl-2,3,4,9-tetrahydro-1H-pyrido[3,4-b]indol-1-yl)-3,5-difluorophenyl)acrylic acid (22)

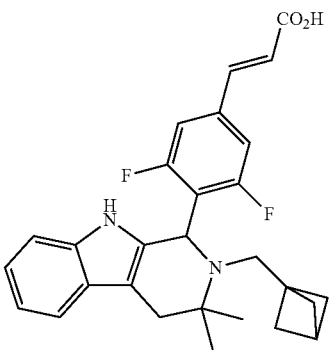 [SMILES: CC1(C)Cc2c([nH]c3ccccc23)C(c2c(F)cc(/C=C/C(=O)O)cc2F)N1CC12CC(C1)C2]

Step 1

To a stirred solution of 1-(1H-indol-3-yl)-2-methylpropan-2-amine (0.31 g, 1.65 mmol) in DCM (6.33 ml) were added HATU (0.504 g, 2.14 mmol) and N,N-diisopropylethylamine (0.574 ml, 3.29 mmol) at rt. The mixture was stirred for 10 min at rt and bicyclo[1.1.1]pentane-1-carboxylic acid (0.203 g, 1.81 mmol) was added. After being stirred at rt for 16 h, the reaction mixture was diluted with EtOAc (15 mL) and washed with saturated aqueous NaHCO$_3$ solution. The organic layer was separated, dried over Na$_2$SO$_4$, filtered and concentrated. The resulting residue was purified by flash chromatography (SiO$_2$, 30-60% EtOAc in hexane) to afford N-(1-(1H-indol-3-yl)-2-methylpropan-2-yl)bicyclo[1.1.1]pentane-1-carboxamide (0.36 g, 77% yield). MS (APCI) m/z 283.17 [M+H]+.

Step 2

To a stirred solution of N-(1-(1H-indol-3-yl)-2-methylpropan-2-yl)bicyclo[1.1.1]pentane-1-carboxamide (0.36 g, 1.28 mmol) in THF (5.10 ml) was added LAH (5.19 ml, 10.38 mmol, 2M LAH in THF) dropwise at 0° C. After being refluxed for 18 h, the reaction mixture was quenched sequentially with cold (0-5° C.) water (0.40 mL) slowly, then an aqueous solution of 15% NaOH (0.80 mL) and water (1.2 mL). The resulting precipitate was extracted with EtOAc (2×20 mL). The separated organic layers were dried over Na$_2$SO$_4$, filtered, and concentrated under reduced pressure. The resulting residue was purified by flash chromatography (SiO$_2$, 0-50% DCM/(DCM:methanolic solution of ammonia (7M) (9:1 v/v))) to afford N-(bicyclo[1.1.1]pentan-1-ylmethyl)-1-(1H-indol-3-yl)-2-methylpropan-2-amine (0.14 g, 0.522 mmol, 41% yield). MS (APCI) m/z 269.19 [M+H]+.

Step 3

To a stirred solution of N-(bicyclo[1.1.1]pentan-1-ylmethyl)-1-(1H-indol-3-yl)-2-methylpropan-2-amine (0.07 g, 0.261 mmol) in toluene (0.65 mL) were added (E)-ethyl 3-(3,5-difluoro-4-formylphenyl)acrylate (0.069 g, 0.287 mmol) and acetic acid (0.031 g, 0.522 mmol) at 0° C. After being stirred at 90° C. for 5 h, the reaction mixture was diluted with EtOAc and washed with water. The separated organic layers were dried over sodium sulfate, filtered and concentrated. The resulting residue was purified by flash chromatography (SiO$_2$, 0-15% ethyl acetate in hexane) to afford (E)-ethyl 3-(4-(2-(bicyclo[1.1.1]pentan-1-ylmethyl)-3,3-dimethyl-2,3,4,9-tetrahydro-1H-pyrido[3,4-b]indol-1-yl)-3,5-difluorophenyl)acrylate (0.025 g, 0.051 mmol, 19% yield) as a pale yellow solid. MS (APCI) m/z 491.24 [M+H]+.

Step 4

To a stirred solution of (E)-ethyl 3-(4-(2-(bicyclo[1.1.1]pentan-1-ylmethyl)-3,3-dimethyl-2,3,4,9-tetrahydro-1H-pyrido[3,4-b]indol-1-yl)-3,5-difluorophenyl)acrylate (0.02 g, 0.041 mmol) in a mixture of methanol (1 mL), THF (1 mL) and water (1 mL) was added sodium hydroxide (4.89 mg, 0.122 mmol) at 0° C. After being stirred at rt for 2 h, the mixture was concentrated under reduced pressure and the obtained residue was acidified with a solution of citric acid (1M) at 0° C. to adjust pH to 5. The precipitate was extracted with EtOAc and the organic phase was concentrated. The resulting residue was dissolved in DMSO (1 mL) and purified by reversed-phase HPLC using 10-60% acetonitrile (contains 0.1% formic acid) in water (contains 0.1% formic acid) to obtain (E)-3-(4-(2-(bicyclo[1.1.1]pentan-1-ylmethyl)-3,3-dimethyl-2,3,4,9-tetrahydro-1H-pyrido[3,4-b]indol-1-yl)-3,5-difluorophenyl)acrylic acid (0.008 g, 41% yield) as a mixture of enantiomers. $^1$H NMR (400 MHz, CDCl$_3$) δ 7.62 (br d, J=16.0 Hz, 1H), 7.53-7.45 (m, 1H), 7.22-7.18 (m, 1H), 7.14-7.08 (m, 2H), 7.03 (d, J=8 Hz, 2H), 6.43 (d, J=16.0 Hz, 1H), 5.14 (br s, 1H), 3.02 (br d, J=16.4 Hz, 1H), 2.91 (br d, J=13.9 Hz, 1H), 2.63 (br d, J=14.9 Hz, 1H), 2.28 (br d, J=16.4 Hz, 1H), 2.19 (s, 1H), 1.33-1.22 (m, 6H), 1.18 (br d, J=8 Hz, 3H), 1.03 (s, 3H) (missing carboxylic acid and NH protons); MS (APCI) m/z 463.21 [M+H]+.

Example 23A and 23B (E)-3-(4-((1R,3R)-3-Ethyl-2-((S)-tetrahydrofuran-3-yl)-2,3,4,9-tetrahydro-1H-pyrido[3,4-b]indol-1-yl)-3,5-difluorophenyl)acrylic acid (23A)

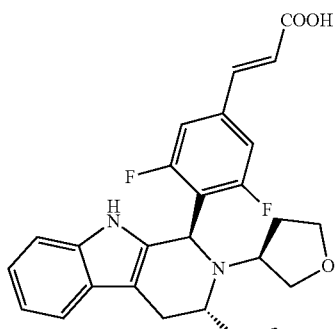

(E)-3-(4-((1R,3R)-3-Ethyl-2-((R)-tetrahydrofuran-3-yl)-2,3,4,9-tetrahydro-1H-pyrido[3,4-b]indol-1-yl)-3,5-difluorophenyl)acrylic acid (23B)

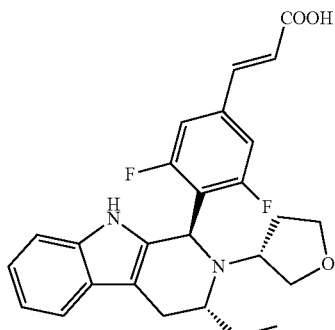

Step 1

To a suspension of (R)-2-((((9H-fluoren-9-yl)methoxy)carbonyl)amino)butanoic acid (4 g, 12.3 mmol) in DCM (40 mL) was added oxalyl dichloride (1.58 ml, 18.4 mmol) followed by a catalytic amount of DMF (0.095 ml, 1.23 mmol) at 0° C. After being stirred at rt for 3 h, the reaction mixture was concentrated. The residue was treated twice with toluene and concentrated (2×25 mL) to afford crude (9H-fluoren-9-yl)methyl (R)-(1-chloro-1-oxobutan-2-yl)carbamate (4.06 g, 96% yield) as a white solid.

Step 2

Under an argon atmosphere, ethylmagnesium bromide (8.54 ml, 25.6 mmol, 3.0M solution in $Et_2O$) was added dropwise into a solution of 1H-indole (1 g, 8.54 mmol) in DCM (50 mL) at 0° C. over a period of 1 h. After being stirred at rt for another 1 h, the mixture was then cooled to 0° C. and treated with a solution of (R)-(9H-fluoren-9-yl)methyl(1-chloro-1-oxobutan-2-yl)carbamate (4.40 g, 12.80 mmol) in DCM (30 mL). After being stirred at rt for 12 h, the reaction was quenched with aqueous HCl (200 mL, 2N) at 0° C. The organic layer was separated and the aqueous layer was extracted with DCM (2×50 mL). The combined organic layers were washed with water and brine, dried over sodium sulfate, filtered, and concentrated to afford (9H-fluoren-9-yl)methyl (R)-(1-(1H-indol-3-yl)-1-oxobutan-2-yl)carbamate (2.17 g, 5.11 mmol, 60% yield) as a brown liquid which was used directly in the next reaction. MS (APCI) m/z 425.18 $[M+H]^+$.

Step 3

To a solution of (R)-(9H-fluoren-9-yl)methyl (1-(1H-indol-3-yl)-1-oxobutan-2-yl)carbamate (2.2 g, 5.18 mmol) in acetonitrile/IPA (7:1, total of 32 mL) was added sodium borohydride (1.961 g, 51.8 mmol) under an argon atmosphere at 0° C. After being refluxed for 16 h, the mixture was cooled to 0° C., quenched with methanol (25 ml), and stirred at rt for 15 min. The resulting mixture was then concentrated under reduced pressure, diluted with EtOAc and washed with water. The organic layer was dried over sodium sulfate, filtered and concentrated. The residue was purified by flash chromatography ($SiO_2$, 0-15% methanol in DCM) to afford (R)-1-(1H-indol-3-yl)butan-2-amine (0.47 g, 2.496 mmol, 48% yield). MS (APCI) m/z 189.13 $[M+H]^+$.

Step 4

To a stirred solution of (R)-1-(1H-indol-3-yl)butan-2-amine (0.47 g, 2.50 mmol) in ethanol (6 mL) were added dihydrofuran-3(2H)-one (0.258 g, 3.00 mmol) and acetic acid (0.150 g, 2.50 mmol) at rt. The mixture was stirred at rt for 3 h and then cooled to 0° C. Sodium borohydride (0.142 g, 3.74 mmol) was added. After being stirred at 0° C.—rt for 16 h, the reaction mixture was concentrated, diluted with ethyl acetate (10 mL), and washed with saturated aqueous $NH_4Cl$ solution (10 mL). The organic layer was separated, dried over sodium sulfate, and concentrated. The residue was purified by flash chromatography ($SiO_2$, 0-10% methanol in DCM) to afford N—((R)-1-(1H-indol-3-yl)butan-2-yl)tetrahydrofuran-3-amine (0.20 g, 31.0% yield) as a yellowish oil. MS (APCI) m/z 259.17 $[M+H]^+$.

Step 5

To a stirred solution of N—((R)-1-(1H-indol-3-yl)butan-2-yl)tetrahydrofuran-3-amine (0.20 g, 0.774 mmol) in toluene (2 mL) were added (E)-ethyl 3-(3,5-difluoro-4-formylphenyl)acrylate (0.223 g, 0.929 mmol) and acetic acid (0.093 g, 1.548 mmol) at 0° C. After being stirred at 90° C. for 5 h, the reaction mixture was diluted with EtOAc and washed with water. The organic layer was separated, dried over sodium sulfate, and concentrated. The resulting residue was purified by flash chromatography ($SiO_2$, 60-100% EtOAc in hexane) to afford (E)-ethyl 3-(4-((1R,3R)-3-ethyl-2-(tetrahydrofuran-3-yl)-2,3,4,9-tetrahydro-1H-pyrido[3,4-b]indol-1-yl)-3,5-difluorophenyl)acrylate (0.22 g, 0.458 mmol, 59% yield) as a mixture of trans isomers. MS (APCI) m/z 481.22 $[M+H]^+$.

Step 6

To a stirred solution of (E)-ethyl 3-(4-((1R,3R)-3-ethyl-2-(tetrahydrofuran-3-yl)-2,3,4,9-tetrahydro-1H-pyrido[3,4- b]indol-1-yl)-3,5-difluorophenyl)acrylate (0.30 g, 0.624 mmol) in a mixture of methanol (1.5 mL), THF (1.5 mL) and water (1.5 mL) was added sodium hydroxide (0.075 g, 1.87 mmol) at 0° C. After being stirred at rt for 2 h, the mixture was concentrated under reduced pressure to remove organic solvents. The residue was acidified with aqueous citric acid (1M) at 0° C. to adjust pH to 5. Ethyl acetate was added to dissolve the formed precipitate. The organic layer was washed with water, separated, and concentrated. The residue was dried under reduced pressure to afford (E)-3-(4-((1R, 3R)-3-ethyl-2-(tetrahydrofuran-3-yl)-2,3,4,9-tetrahydro-1H-pyrido[3,4-b]indol-1-yl)-3,5-difluorophenyl)acrylic acid (0.22 g, 78% yield) as a mixture of trans isomers. MS (APCI) m/z 453.19 [M+H]+.

Step 7

The mixture of isomers, (E)-3-(4-((1R,3R)-3-ethyl-2-(tetrahydrofuran-3-yl)-2,3,4,9-tetrahydro-1H-pyrido[3,4-b]indol-1-yl)-3,5-difluorophenyl)acrylic acid, was purified by reversed phase prep HPLC [Conditions: (A) 0.1% Formic Acid in water; (B) acetonitrile; Flow: 19 mL/min; Column: Xterra (19×150 mm) 5 μm; Gradient-(Time (min)/% B): 0.1/35; 11/35, 11.1/98, 13/98, 13.1/10, 15/10] to afford (E)-3-(4-((1R,3R)-3-ethyl-2-((S)-tetrahydrofuran-3-yl)-2,3,4,9-tetrahydro-1H-pyrido[3,4-b]indol-1-yl)-3,5-difluorophenyl)acrylic acid (Designated as Peak 1) (20 mg, 0.04 mmol, 25% yield) and (E)-3-(4-((1R,3R)-3-ethyl-2-((R)-tetrahydrofuran-3-yl)-2,3,4,9-tetrahydro-1H-pyrido[3,4-b]indol-1-yl)-3,5-difluorophenyl)acrylic acid (Designated as Peak 2) (14 mg, 0.03 mmol, 17% yield) as an off white solid after lyophilization.

(E)-3-(4-((1R,3R)-3-ethyl-2-((S)-tetrahydrofuran-3-yl)-2,3,4,9-tetrahydro-1H-pyrido[3,4-b]indol-1-yl)-3,5-difluorophenyl)acrylic acid: $^1$H NMR (400 MHz, DMSO-$d_6$) δ 10.2 (s, 1H), 7.48 (d, J=15.8 Hz, 1H), 7.46 (d, J=10.4 Hz, 2H), 7.41 (d, J=7.2 Hz, 1H), 7.20 (d, J=7.6 1H), 7.01 (dd, J=7.6, 6.6 Hz, 1H), 6.97 (dd, J=7.2, 6.8 Hz, 1H), 6.64 (d, J=15.6 Hz, 1H), 5.38 (s, 1H), 3.81-3.79 (m, 1H), 3.62-3.58 (m, 1H), 3.50-3.46 (m, 1H), 3.31-3.10 (m, 4H), 2.74 (dd, J=18.4, 15.2 Hz, 1H), 2.10-2.06 (m, 2H), 1.69-1.65 (m, 1H), 1.52-1.49 (m, 1H), 0.83 (t, J=7.2 Hz, 3H), carboxylic acid proton not observed; MS (ESI) m/z 452.99 [M+H]+.

(E)-3-(4-((1R,3R)-3-ethyl-2-((R)-tetrahydrofuran-3-yl)-2,3,4,9-tetrahydro-1H-pyrido[3,4-b]indol-1-yl)-3,5-difluorophenyl)acrylic acid: $^1$H NMR (400 MHz, DMSO-$d_6$) δ 10.2 (s, 1H), 7.43-7.38 (m, 4H), 7.21 (d, J=8.0, 1H), 7.01 (dd, J=7.6, 7.2 Hz, 1H), 6.95 (dd, J=7.2, 6.8 Hz, 1H), 6.61 (d, J=16.4 Hz, 1H), 5.35 (s, 1H), 3.75-3.66 (m, 4H), 3.56-3.10 (m, 1H), 3.08-3.00 (m, 1H), 2.76 (dd, J=17.8, 15.0 Hz, 1H), 2.69-2.58 (m, 1H), 1.65-1.51 (m, 4H), 0.80 (t, J=7.2 Hz, 3H), carboxylic acid proton not observed; MS (ESI) m/z 452.96 [M+H]+.

Compounds 23A and 23B are shown above and in Table 1 with absolute stereochemistry in the tetrahydrofuran ring arbitrarily assigned.

Example 24

(E)-3-(4-(2-(Bicyclo[1.1.1]pentan-1-ylmethyl)-3-ethyl-2,3,4,9-tetrahydro-1H-pyrido[3,4-b]indol-1-yl)-3,5-difluorophenyl)acrylic acid (24)

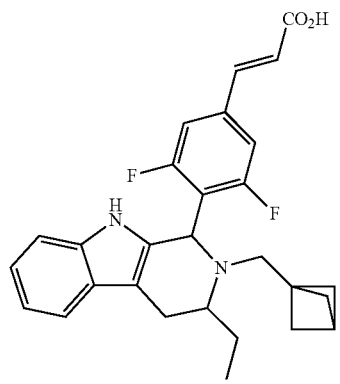 [SMILES: CCC1Cc2c([nH]c3ccccc23)C(c2c(F)cc(/C=C/C(=O)O)cc2F)N1CC12CC(C1)C2]

Step 1

To a stirred solution of 1-((1H-indol-3-yl)methyl)cyclopropanamine (0.19 g, 1.02 mmol) in DCM (3.92 ml) were added HATU (0.312 g, 1.33 mmol) and N,N-diisopropylethylamine (0.355 ml, 2.04 mmol) at rt. The mixture was stirred for 10 min and bicyclo[1.1.1]pentane-1-carboxylic acid (0.126 g, 1.12 mmol) was added. After being stirred at rt for 16 h, the mixture was diluted with ethyl acetate (15 mL) and washed with saturated aqueous NaHCO$_3$ solution. The organic layer was separated, dried over Na$_2$SO$_4$, filtered and concentrated. The resulting residue was purified by flash chromatography (SiO$_2$, 30-60% EtOAc in hexane) to afford N-(1-((1H-indol-3-yl)methyl)cyclopropyl)bicyclo[1.1.1]pentane-1-carboxamide (0.20 g, 0.713 mmol, 70% yield) as an off-white solid. MS (APCI) m/z 281.16 [M+H]+.

Step 2

To a stirred solution of N-(1-((1H-indol-3-yl)methyl)cyclopropyl)bicyclo[1.1.1]pentane-1-carboxamide (0.20 g, 0.713 mmol) in THF (2.85 ml) was added LAH (1.783 ml, 3.57 mmol, 2M LAH in THF) dropwise at 0° C. After being refluxed for 18 h, the reaction mixture was quenched sequentially with cold (0-5° C.) water (0.15 mL), 15% aqueous NaOH (0.30 mL), and water (0.50 mL). The resulting residue was extracted with EtOAc (3×10 mL). The combined organic layers were dried over Na$_2$SO$_4$, filtered, and concentrated. The resulting residue was purified by flash chromatography (SiO$_2$, 0-50% DCM/(DCM:7M ammonia in MeOH (9:1 v/v))) to afford 1-((1H-indol-3-yl)methyl)-N-(bicyclo[1.1.1]pentan-1-ylmethyl)cyclopropanamine (0.13 g, 68% yield) as a white solid. MS (APCI) m/z 267.18 [M+H]+.

Step 3

To a stirred solution of 1-((1H-indol-3-yl)methyl)-N-(bicyclo[1.1.1]pentan-1-ylmethyl)cyclopropanamine (0.11 g, 0.413 mmol) in toluene (1.5 mL) were added (E)-ethyl 3-(3,5-difluoro-4-formylphenyl)acrylate (0.11 g, 0.11 mmol) and acetic acid (0.050 g, 0.826 mmol) at 0° C. After being stirred at 80° C. for 3 h, the reaction mixture was cooled to rt, diluted with EtOAc, and washed with water. During the reaction, LCMS showed the formation of a side product which corresponded to the rearrangement of the cyclopropyl ring. The organic layer was separated, dried over sodium sulfate, and concentrated. The resulting residue was purified by flash chromatography (SiO$_2$, 0-20% EtOAc in hexane) to afford ethyl (E)-3-(4-(2-(bicyclo[1.1.1]pentan-1-ylmethyl)-3-ethyl-2,3,4,9-tetrahydro-1H-pyrido[3,4-b]indol-1-yl)-3,5-difluorophenyl)acrylate (0.10 g, 49% yield) as a mixture of isomers. MS (APCI) m/z 491.24 [M+H]$^+$.

Step 4

To a stirred solution of (E)-ethyl 3-(4-(2-(bicyclo[1.1.1]pentan-1-ylmethyl)-3-ethyl-2,3,4,9-tetrahydro-1H-pyrido[3,4-b]indol-1-yl)-3,5-difluorophenyl)acrylate (0.10 g, 0.204 mmol) in a mixture of methanol (1 mL), THF (1 mL) and water (1 mL) was added sodium hydroxide (0.024 g, 0.612 mmol) at 0° C. After being stirred at rt for 2 h, the organic solvents were removed under reduced pressure and the resulting mixture was acidified with aqueous citric acid (1M) at 0° C. to adjust pH to 5. The formed precipitate was extracted with EtOAc and the organic layer was concentrated. The resulting solid was dissolved in DMSO (1.5 mL) and purified by reversed-phase HPLC using 10-50% acetonitrile (contains 0.1% formic acid) in water (contains 0.1% formic acid) to afford (E)-3-(4-(2-(bicyclo[1.1.1]pentan-1-ylmethyl)-3-ethyl-2,3,4,9-tetrahydro-1H-pyrido[3,4-b]indol-1-yl)-3,5-difluorophenyl)acrylic acid (0.03 g, 31% yield) as a mixture of isomers. MS (APCI) m/z 463.21 [M+H]$^+$.

Example 25A and 25B (E)-3-(4-((1R,3R)-2-(Bicyclo[1.1.1]pentan-1-yl)-3-ethyl-2,3,4,9-tetrahydro-1H-pyrido[3,4-b]indol-1-yl)-3,5-difluorophenyl)acrylic acid (25A)

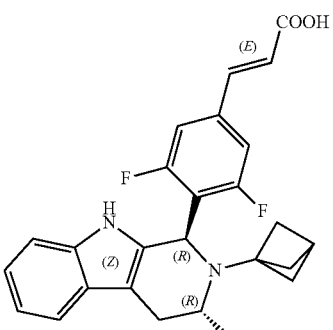

(E)-3-(4-((1S,3S)-2-(Bicyclo[1.1.1]pentan-1-yl)-3-ethyl-2,3,4,9-tetrahydro-1H-pyrido[3,4-b]indol-1-yl)-3,5-difluorophenyl)acrylic acid (25B)

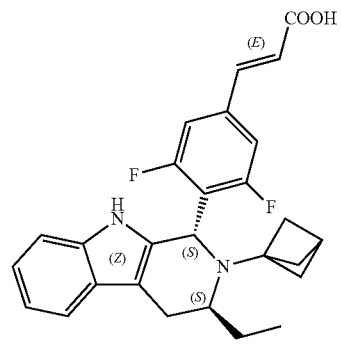

Step 1

To a stirred solution of 2-(1H-indol-3-yl)acetic acid (100 g, 571.4 mmol) in dichloromethane (1L) was added 1,1-carbonyldiimidazole (92 g, 571 mmol) in portions at rt under an argon atmosphere. The mixture was stirred at rt for 2 h and N,O-dimethylhydroxylamine hydrochloride (54 g, 571 mmol) was added. After being stirred at rt for 24 h, the reaction mixture was diluted with cold water and extracted with dichloromethane (2×250 mL). The combined organic layers were dried over sodium sulfate, filtered, and concentrated. The resultant residue was purified by trituration with pentane to afford 2-(1H-indol-3-yl)-N-methoxy-N-methylacetamide (110 g, 504.5 mmol, 80% yield) as an off white solid. MS (ESI) m/z; 218.84 [M+H]$^+$.

Step 2

To a stirred solution of 2-(1H-indol-3-yl)-N-methoxy-N-methylacetamide (5.0 g, 22.9 mmol) in THF (350 mL) was added dropwise ethylmagnesium bromide (22.5 mL, 67.6 mmol, 3M in diethyl ether) at 0° C. After being stirred at 0° C. for another 2 h under an argon atmosphere, the reaction was quenched by aqueous saturated NH$_4$Cl solution (200 mL) at 0° C. The organic layer was separated and the aqueous layer was extracted with EtOAc (2×200 mL). The combined organic layers were washed with water, brine, dried over sodium sulfate, filtered, and concentrated. The crude residue was purified by column chromatography (SiO$_2$, 30% ethyl acetate in hexanes) to afford 1-(1H-indol-3-yl)butan-2-one (2.78 g, 14.8 mmol, yield 60% yield) as an off white semi-solid. MS (ESI) m/z 188.15 [M+H]$^+$.

Step 3

To a stirred solution of bicyclo[1.1.1]pentan-1-amine-HCl (0.9 g, 7.69 mmol) in MeOH (180 mL) was added AcOH to adjust pH to 5-6. To the mixture were added 1-(1H-Indol-3-yl)butan-2-one (1.2 g, 6.41 mmol) and sodium cyanoborohydride (720 mg, 11.5 mmol) at 0° C. After being stirred at rt for 12 h, the reaction mixture was concentrated under reduced pressure to remove organic solvents. The resultant residue was poured into water and extracted with EtOAc (2×100 mL). The combined organic layer was washed with aqueous NaHCO$_3$ solution, water, and brine. The washed organic layer was then dried over sodium sulfate, filtered, and concentrated. The residue was purified by column chromatography ($SiO_2$, 30% ethyl acetate in hexanes) to afford N-(1-(1H-indol-3-yl)butan-2-yl)bicyclo[1.1.1]pentan-1-amine (0.90 g, 3.54 mmol, 56% yield) as a yellow liquid. MS (ESI) m/z 255.0 $[M+H]^+$.

Step 4

N-(1-(1H-indol-3-yl)butan-2-yl)bicyclo[1.1.1]pentan-1-amine (0.90 g) was purified by Chiral SFC [Column: Lux Cellulose-2 (250×30 mm), 5 μm % $CO_2$:85.0: % Co solvent: 15.0% (0.5% DEA in MeOH): Total Flow: 90.0 g/min: Back Pressure: 100.0 bar: UV: 219 nm: Stack time: 4.0 min: Load/Inj: 18.0 mg: Solubility: Methanol: No of injections: 50: Instrument details: Make/Model: Thar SFC-200-005] to afford (R)—N-(1-(1H-indol-3-yl)butan-2-yl)bicyclo[1.1.1]pentan-1-amine (Designated as Peak 1) (160 mg, 0.63 mmol, 32.0% yield) and (S)—N-(1-(1H-indol-3-yl)butan-2-yl)bicyclo[1.1.1]pentan-1-amine (Designated as Peak 2) (160 mg, 0.63 mmol, 33.0% yield) respectively.

(R)—N-(1-(1H-indol-3-yl)butan-2-yl)bicyclo[1.1.1]pentan-1-amine: MS (ESI) m/z 255.0 $[M+H]^+$.

(S)—N-(1-(1H-indol-3-yl)butan-2-yl)bicyclo[1.1.1]pentan-1-amine: MS (ESI) m/z 255.0 $[M+H]^+$.

Step 5-a

To a stirred solution of (R)—N-(1-(1H-indol-3-yl)butan-2-yl)bicyclo[1.1.1]pentan-1-amine (160 mg, 0.63 mmol) in toluene (8.0 mL) were added (E)-methyl-3-(3,5-difluoro-4-formylphenyl) acrylate (142.0 mg, 0.63 mmol) and AcOH (0.75 mL, 1.26 mmol) at 0° C. After being stirred at 90° C. for 6 h, the mixture was allowed to cool to rt, quenched by water, and extracted with ethyl acetate. The combined organic layer was dried over $Na_2SO_4$, filtered and concentrated. The residue was purified by column chromatography ($SiO_2$, 20% ethyl acetate in hexane) to afford (E)-methyl 3-(4-((1R,3R)-2-(bicyclo[1.1.1]pentan-1-yl)-3-ethyl-2,3,4,9-tetrahydro-1H-pyrido[3,4-b]indol-1-yl)-3,5-difluorophenyl)acrylate (120 mg, 0.26 mmol, 41% yield). MS (ESI) m/z 463.7 $[M+H]^+$.

Step 5-b

To a stirred solution of (S)—N-(1-(1H-indol-3-yl)butan-2-yl)bicyclo[1.1.1]pentan-1-amine (160 mg, 0.63 mmol) in toluene (8.0 mL) were added (E)-methyl-3-(3,5-difluoro-4-formylphenyl) acrylate (142.0 mg, 0.63 mmol) and AcOH (0.75 mL, 1.26 mmol) at 0° C. After being stirred at 90° C. for 6 h, the reaction was cooled to rt, quenched by water, and extracted with ethyl acetate. The combined organic layer was dried over $Na_2SO_4$, filtered, and concentrated. The resultant residue was purified by column chromatography ($SiO_2$, 20% ethyl acetate in hexanes) to afford methyl (E)-3-(4-((1S,3S)-2-(bicyclo[1.1.1]pentan-1-yl)-3-ethyl-2,3,4,9-tetrahydro-1H-pyrido[3,4-b]indol-1-yl)-3,5-difluorophenyl)acrylate (80 mg, 0.172 mmol, 27% yield). MS (ESI) m/z 463.7 $[M+H]^+$.

Step 6-a

To a stirred solution of (E)-methyl 3-(4-((1R,3R)-2-(bicyclo[1.1.1]pentan-1-yl)-3-ethyl-2,3,4,9-tetrahydro-1H-pyrido[3,4-b]indol-1-yl)-3,5-difluorophenyl)acrylate (120 mg, 0.26 mmol) in THF/water (5.0 mL, 1:1) was added LiOH (63 mg, 1.56 mmol) at 0° C. After being stirred at rt for 6 h, the reaction mixture was washed with diethyl ether and the separated aqueous layer was acidified to pH 3-4 with aqueous HCl (1.0M) at 0° C. The resulting precipitate was filtered, washed with water, and dried to afford (E)-3-(4-((1R,3R)-2-(bicyclo[1.1.1]pentan-1-yl)-3-ethyl-2,3,4,9-tetrahydro-1H-pyrido[3,4-b]indol-1-yl)-3,5-difluorophenyl) acrylic acid (0.030 g, 0.0668 mmol, 26% yield) as a pale yellow solid. $^1$H NMR (300 MHz, DMSO-$d_6$) δ 10.5 (br s, 1H), 7.57-7.40 (m, 4H), 7.19 (d, J=6.6 Hz, 1H), 7.02-6.94 (m, 2H), 6.67 (d, J=15.6 Hz, 1H), 5.40 (s, 1H), 3.22 (s, 1H), 2.78 (s, 2H), 2.26 (s, 1H), 1.78-1.66 (m, 6H), 1.40 (s, 1H), 1.23 (s, 1H), 0.87-0.85 (m, 3H); mp: 178-180° C.; MS (ESI) m/z 449.11 $[M+H]^+$.

Step 6-b

To a stirred solution of (E)-methyl-3-(4-((1S,3S)-2-(bicyclo[1.1.1]pentan-1-yl)-3-ethyl-2,3,4,9-tetrahydro-1H-pyrido[3,4-b]indol-1-yl)-3,5-difluorophenyl)acrylic acid (80 mg, 0.173 mmol) in THF/water (5.0 mL, 1:1) was added LiOH (42 mg, 1.03 mmol) at 0° C. After being stirred at rt for 6 h, the mixture was washed with diethyl ether and the separated aqueous layer was acidified to pH 3-4 with aqueous HCl (1.0M) at 0° C. The formed precipitated was filtered, washed with water, and dried to afford (E)-3-(4-((1S,3S)-2-(bicyclo[1.1.1]pentan-1-yl)-3-ethyl-2,3,4,9-tetrahydro-1H-pyrido[3,4-b]indol-1-yl)-3,5-difluorophenyl) acrylic acid (0.011 g, 0.024 mmol, 14% yield) as a pale yellow solid. $^1$H NMR (300 MHz, DMSO-$d_6$) δ 12.6 (br s, 1H), 10.6 (br s, 1H), 7.56-7.40 (m, 4H), 7.18 (d, J=5.7 Hz, 1H), 7.00-6.92 (m, 2H), 6.66 (d, J=11.7 Hz, 1H), 5.39 (s, 1H), 3.18 (s, 1H), 2.77 (s, 2H), 2.25 (s, 1H), 1.77-1.63 (m, 6H), 1.43 (s, 1H), 1.23 (s, 1H), 0.85 (m, 3H); mp: 180-182° C.; MS (ESI) m/z 449.11 $[M+H]^+$.

Compounds 25A and 25B are shown above and in Table 1 with absolute stereochemistry arbitrarily assigned.

Example 26A (E)-3-(4-((1R,3R)-2-(bicyclo[1.1.1]pentan-1-yl)-3,9-dimethyl-2,3,4,9-tetrahydro-1H-pyrido[3,4-b]indol-1-yl)-3,5-difluorophenyl)acrylic acid (26A)

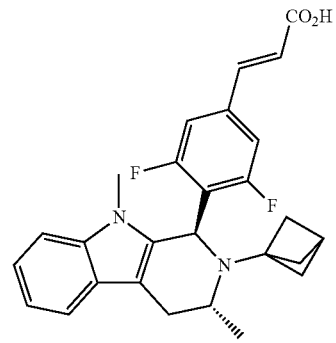 [SMILES: C[C@@H]1Cc2c(n(C)c3ccccc23)[C@@H](c2c(F)cc(/C=C/C(=O)O)cc2F)N1C12CC(C1)C2]

Step 1

To a stirred solution of methyl (E)-3-(4-((1R,3R)-2-(bicyclo[1.1.1]pentan-1-yl)-3-methyl-2,3,4,9-tetrahydro-1H-pyrido[3,4-b]indol-1-yl)-3,5-difluorophenyl)acrylate (200 mg, 0.44 mmol) in dimethylcarbonate (2 mL) was added DABCO (5 mg, 0.04 mmol) followed by DMF (0.2 mL, catalytic) at rt. After being stirred at 95° C. for 40 h, the reaction mixture was quenched by cold water and extracted with EtOAc (3×100 mL). The combined organic layer was washed with water and brine. The washed organic layer was dried over sodium sulfate, filtered, and concentrated. The crude compound was purified by flash chromatography (SiO$_2$ 25% ethyl acetate/hexanes) to afford methyl (E)-3-(4-((1R,3R)-2-(bicyclo[1.1.1]pentan-1-yl)-3,9-dimethyl-2,3,4,9-tetrahydro-1H-pyrido[3,4-b]indol-1-yl)-3,5-difluorophenyl)acrylate (80 mg, 0.17 mmol, 39% yield) as an off-white solid. MS (ESI) m/z 463.11 [M+H]$^+$.

Step 2

To a stirred solution of methyl (E)-3-(4-((1R,3R)-2-(bicyclo[1.1.1]pentan-1-yl)-3,9-dimethyl-2,3,4,9-tetrahydro-1H-pyrido[3,4-b]indol-1-yl)-3,5-difluorophenyl)acrylate (80 mg, 0.17 mmol) in THF/H$_2$O (1:1, total of 4 mL) was added LiOH.H$_2$O (130 mg, 0.51 mmol) at 0° C. After being stirred at rt for 5 h, the reaction mixture was concentrated under reduced pressure to remove the organic solvent. The residue was acidified with 1N aqueous HCl at 0° C. and extracted with EtOAc (3×100 mL). The combined organic layer was washed with water and brine, dried over sodium sulfate, filtered, and concentrated. The crude compound was purified by flash chromatography (SiO$_2$, 2% MeOH/DCM) to afford (E)-3-(4-((1R,3R)-2-(bicyclo[1.1.1]pentan-1-yl)-3,9-dimethyl-2,3,4,9-tetrahydro-1H-pyrido[3,4-b]indol-1-yl)-3,5-difluorophenyl)acrylic acid (30 mg, 0.06 mmol, 38% yield). $^1$H NMR (400 MHz, DMSO-d$_6$) δ 12.5 (br s, 1H), 7.52 (d, J=16.4 Hz, 2H), 7.44 (d, J=7.6 Hz, 2H), 7.31 (d, J=8.4 Hz, 1H), 7.08 (t, J=7.2 Hz, 1H), 6.99 (t, J=7.2 Hz, 1H), 6.64 (d, J=16.0 Hz, 1H), 5.44 (s, 1H), 3.50 (m, 1H), 3.33 (s, 3H), 2.91 (dd, J=14.4, 3.2 Hz, 1H), 2.63 (m, 1H), 2.26 (s, 1H), 1.73 (d, J=9.6 Hz, 3H), 1.71 (d, J=8.8 Hz, 3H), 1.11 (d, J=6.4 Hz, 3H); MS (ESI) m/z 449.50 [M+1]+.

Example A

Breast Cancer Cell Proliferation Assay (MCF-7)

MCF7 was expanded and maintained in the medium (Phenol red free DMEM/F12 (Hyclone SH30272.01) NEAA (Gibco11140-050) Na-pyruvate (Gibco 11360-070) and Re-stripped Charcoal stripped FBS (Gemini 100-119)). The cells were adjusted to a concentration of 3,000 cells per mL in the above media, and the cells were incubated (37° C., 5% CO$_2$). The following day a 10 point, serial dilution of compounds was added to the cells at a final concentration ranging from 10-0.000005 µM for test compounds (17β-estradiol was used as a control). Additional cells were plated in 30 wells to serve as the day 1 (pretreatment) comparison. After 5 days of compound exposure, Cell Titer-Glo reagent was added to the cells and the relative luminescence units (RLUs) of each well was determined. Cell Titer-Glo was also added to 32 µL of medium without cells to obtain a background value. The plates were allowed to incubate at room temperature for 10 minutes to stabilize luminescent signal and the luminescence signal was recorded with EnSpire. The relative increase in cell number of each sample is determined as follows: (RLU sample-RLU background/RLU estrogen only treated cells-RLU background)×100=% inhibition.

Example B

ER Degradation Determination by Western Blot

MCF-7 cells are plated at 0.3 million cells/mL (3 mL/well) in 6-well plates in experiment media and incubated at 37° C., 5% CO2 for 48 hours. Next day, 10× solution of compounds are made in DMSO and added the solution to the cells to achieve a final concentration of 10 µM. A DMSO control is included to enable a determination of the relative efficacy of test compounds. Fulvestrant is used as a positive control for ER-alpha degradation, and 4-OH tamoxifen as a control for receptor stabilization. After incubating cells with compounds for 18-24 hours, cell lysates are prepared (2× Cell lysis buffer:100 mM Tris, pH 8, 300 mM NaCl, 2% NP40, 1% Na deoxycholate, 0.04% SDS, 2 mM EDTA) and mixed thoroughly and incubated on ice. The protein concentration is quantified using BCA kit. Protein was separated on 4%-20% NuPAGE Novex 4-12% Bis-Tris Protein Gels using 1×MES running buffer. The gel was then transferred onto a nitrocellulose membrane. The blots were probed with antibodies against ESR1 protein (Santa Cruz, sc-8005). GAPDH protein was used as an internal control.

Example C

ERα EC50 Determination

MCF-7 cells are plated at 0.3 million cells/mL (3 mL/well) in 6-well plates in experiment media and incubated at 37° C., 5% CO2 for 48 hours. Next day, 10 mM solution of compounds are made in DMSO and added the solution to the cells to achieve a final concentration of 10 µM. For EC$_{50}$ determination, MCF-7 cells were incubated with 3× or 5× serial dilutions of 10 mM compounds, final concentration of the compounds was from 10 µM to designed concentrations based on the potency of the compounds. A DMSO control is included to enable a determination of the relative efficacy of test compounds. Fulvestrant is used as a positive control for ER-alpha degradation, and 4-OH tamoxifen as a control for receptor stabilization. After incubating cells with compounds for 18-24 hours, cell lysates are prepared (2× Cell lysis buffer:100 mM Tris, pH 8, 300 mM NaCl, 2% NP40, 1% Na deoxycholate, 0.04% SDS, 2 mM EDTA) and mixed thoroughly and incubated on ice. The protein concentration is quantified using BCA kit. Protein was separated on 4%-20% NuPAGE Novex 4-12% Bis-Tris Protein Gels using 1×MES running buffer. The gel was then transferred onto a nitrocellulose membrane. The blots were probed with antibodies against ESR1 protein (Santa Cruz, sc-8005). GAPDH protein was used as an internal control. The blots were imaged on Azure C600 Imager and Band density of the western blots was quantified with Azurespot software. EC$_{50}$ is calculated with Graphpad-Prism.

TABLE 3

| Example | MCF7 IC$_{50}$ (nM) | ERα % degradation |
|---|---|---|
| fulvestrant | A | A |
| AZD9496 | A | A |
| ARN810 | A | A |
| 4A | B | A |
| 5A | A | A |
| 6A | ND | B |
| 8A | B | A |
| 8B | B | B |
| 9A | B | A |
| 11A | A | A |
| 11C | C | ND |
| 11D | A | ND |
| 13A | B | ND |

TABLE 3-continued

| Example | MCF7 IC$_{50}$ (nM) | ERα % degradation |
|---|---|---|
| 13B | A | B |
| 14A | B | B |
| 15A | A | ND |
| 16A | A | ND |
| 17A | B | ND |
| 18A | A | ND |
| 19A | A | ND |
| 21A | A | ND |
| 22 | B | ND |
| 23A | A | ND |
| 23B | B | ND |
| 24 | B | ND |
| 25A | C | ND |
| 25B | A | ND |
| 26A | C | ND |

For MCF7 IC$_{50}$: A = a single IC$_{50}$ ≤25 nM; B = a single IC$_{50}$ ≥25 nM and ≤250 nM; C = a single IC$_{50}$ ≥250 nM. For ERα % degradation: A = ERα % degradation ≥80%; B = ERα % degradation <80%; ND = Not Determined.

Example D

Pharmacokinetic Determination

Grouping female SD rats weighing 200-300 g randomly to two groups; one group was administered with test compound at a dose of 3.0 mg/kg by intravenous injection, the other group was administered with test compound at a dose of 10.0 mg/kg by oral. The formulation for IV groups is DMSO/PEG400/150 mM glycine (pH 9) (5/10/85) and the formulation for PO groups is PEG400/PVP/Tween 80/0.5% CMC in water (9/0.5/0.5/90). After administering, blood samples of intravenous injection group were collected at time points of predose, 0.0833, 0.25, 0.5, 1, 2, 4, 8, 12 and 24 h; blood samples of oral group were collected at time points of predose, 0.25, 0.5, 1, 2, 4, 8, 12, and 24 h. Standard curve was plotted based on concentrations of the samples in a suitable range, the concentrations of test compounds in plasma samples were determined by using LC-MS/MS. Pharmacokinetic parameters were calculated according to drug concentration-time curve using a noncompartmental method by WinNonLin (Phoenix™, version 6.1) or other similar software.

TABLE 4

| | | Rat PK | | | | | | |
|---|---|---|---|---|---|---|---|---|
| Example | Dose method | AUC$_{inf}$ (μM*h) | Cl (ml · min$^{-1}$ · kg$^{-1}$) | V$_{dss}$ (L/Kg) | C$_{max}$ (μM) | T$_{max}$ (h) | T$_{1/2}$ (h) | F (%) |
| AZD9496 | IV | 72 | 1.6 | 0.8 | | | 7.8 | |
| | PO | 179 | | | 16.1 | 4 | 6.4 | 74 |
| ARN810 | IV | 5.9 | 19 | 1.2 | | | 4.7 | |
| | PO | 23 | | | 6.7 | 1 | 6.9 | 117 |
| 5A | IV | 67 | 1.7 | 1.0 | | | 7.7 | |
| | PO | 185 | | | 10.8 | 2 | 8.5 | 82 |
| 8A | IV | 22 | 5.2 | 0.6 | | | 3.2 | |
| | PO | 80 | | | 24.5 | 0.5 | 2.1 | 109 |
| 11A | IV | 96 | 1.2 | 0.48 | | | 4.2 | |
| | PO | 283 | | | 33 | 1 | 3.5 | 88 |

What is claimed is:

1. A compound selected from the group consisting of

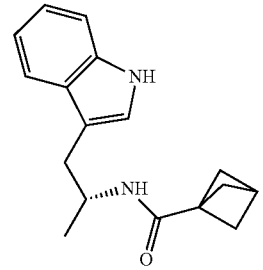

and

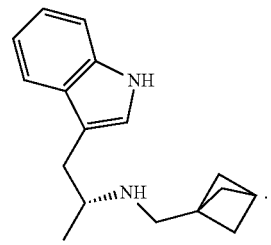

2. A compound of the following Formula 11-4:
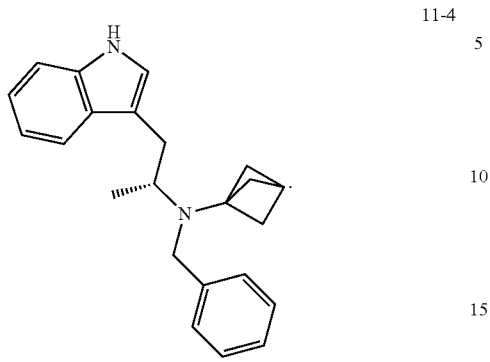
11-4
3. A compound of the following Formula 11-5:
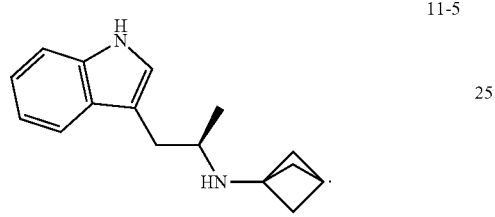
11-5
\* \* \* \* \*